US006537241B1

United States Patent
Odland

(12) United States Patent
(10) Patent No.: US 6,537,241 B1
(45) Date of Patent: Mar. 25, 2003

(54) SYSTEM AND METHOD FOR SITE SPECIFIC THERAPY

(75) Inventor: Rick Mathew Odland, Roseville, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 0 days.

(21) Appl. No.: 09/313,341

(22) Filed: May 17, 1999

Related U.S. Application Data

(63) Continuation of application No. PCT/US98/16416, filed on Aug. 10, 1998, which is a continuation-in-part of application No. 08/908,555, filed on Aug. 8, 1997, now Pat. No. 6,030,358.

(51) Int. Cl.[7] .......................... A61M 5/00; A61M 1/00; A61M 25/00; A61M 31/00

(52) U.S. Cl. ............................. 604/9; 604/504; 604/28; 604/264

(58) Field of Search ................................ 604/4.01, 6.1, 604/6.11, 6.16, 8–10, 27, 28, 30–6, 38, 48, 500, 503–4, 65–67, 93, 118, 131, 149, 151, 163, 164.01–164.02, 164.13, 264, 523, 286, 540–41; 128/898; 138/111, 114–16, 118, 178; 600/562–63; 606/76, 77

(56) References Cited

U.S. PATENT DOCUMENTS

| 4,378,797 A | 4/1983 | Osterholm et al. |
| 4,445,500 A | 5/1984 | Osterholm |
| 4,445,886 A | 5/1984 | Osterholm |

(List continued on next page.)

FOREIGN PATENT DOCUMENTS

| WO | WO 98/05369 | 2/1998 |

OTHER PUBLICATIONS

Odland, Umeda, Stevens, Heinrich, & Rowe, Arch Otolaryngol Head Neck Surgery, 1995 May; "Reduction of Tissue Edema by Microdialysis".*

La Nou, Kelly, "Hemodialysis Membranes: Characteristics of Ideal Membranes, Characteristics of Available Membranes, and the Future of Hemodialysis Membranes" *Biomaterials:* BME 430, Pharmacy 601 (May, 2000).

Odland R, Rheuark, D., Kizziar, R., Ispirescu, S., Davamony, D., Simental, A., "The Effect of Capillary Ultrafiltration Probes on Skin Flap Edema and Survival" Pettis VA Medical Center, Loma Linda University. (Poster Session, 1995).

Odland RM, Kizziar R, Rheuark D, Simental A "The Effect of Capillary Ultrafiltration Probes on Skin Flap Edema" Accepted with revisions, Otolaryngology–Head and Neck Surgery.

(List continued on next page.)

*Primary Examiner*—Angela D. Sykes
*Assistant Examiner*—Patricia M Bianco
(74) *Attorney, Agent, or Firm*—Fredrikson & Byron, P.A.

(57) ABSTRACT

A system, including catheter apparatus, and related method for performing site specific therapy. The catheter apparatus can include one or more semipermeable microcatheters (preferably in the form of hollow fibers) for use in performing site specific microdialysis. The system and method are particularly suited for use in addressing cerebral edema by affecting the osmolar relationship between fluids making up the brain tissue. Also disclosed is an apparatus having a delivery/recovery mechanism in the form of a pump reservoir and one or more catheters in the form of semipermeable microcatheters, for use in delivering and/or recovering fluid to and/or from a tissue site or for performing tissue engineering outside of the body. The apparatus can be used in a method to perform site specific microtherapy, including for the treatment of compartment syndrome or cerebral edema.

51 Claims, 34 Drawing Sheets

U.S. PATENT DOCUMENTS

| | | | |
|---|---|---|---|
| 4,758,431 A | | 7/1988 | Osterholm |
| 4,777,953 A | | 10/1988 | Ash |
| 4,840,617 A | | 6/1989 | Osterholm |
| 4,892,538 A | | 1/1990 | Aebischer et al. ....... 604/891.1 |
| 4,904,237 A | | 2/1990 | Janese |
| 5,002,054 A | | 3/1991 | Ash et al. |
| 5,106,365 A | | 4/1992 | Hernandez |
| 5,106,627 A | | 4/1992 | Aebischer et al. .......... 424/424 |
| 5,191,900 A | | 3/1993 | Mishra |
| 5,200,194 A | | 4/1993 | Edgren et al. |
| 5,334,315 A | | 8/1994 | Matkovich et al. |
| 5,397,354 A | | 3/1995 | Wilk et al. |
| 5,441,481 A | * | 8/1995 | Mishra et al. ............... 600/309 |
| 5,487,739 A | | 1/1996 | Aebischer et al. ....... 604/890.1 |
| 5,607,418 A | | 3/1997 | Aebischer et al. ....... 604/891.1 |
| 5,706,806 A | | 1/1998 | Kissinger |
| 5,735,832 A | | 4/1998 | Karlsson |
| 5,741,284 A | | 4/1998 | Karlsson |
| 5,798,119 A | | 8/1998 | Herbig et al. |
| 5,810,760 A | | 9/1998 | Andrews |
| 5,980,480 A | * | 11/1999 | Rubenstein et al. ............ 604/9 |
| 6,026,316 A | * | 2/2000 | Kucharczyk et al. ....... 324/309 |
| 6,061,587 A | | 5/2000 | Kucharczyk et al. ....... 600/411 |

OTHER PUBLICATIONS

Odland RM, Umeda A "Therapeutic Tissue Microdialysis: Results of an In Vivo Study" Abstracts of the 16th Midwinter Meeting, Association for Research in Otolaryngology, Feb. 1993.

Odland, et al., "Reduction of Tissue Edema by Microdialysis", Otolaryngology Head and Neck Surgery, vol. 121, 1995.

Lonnroth, et al., J. Intern. Med., May 1990; 227(5):295–300, "Microdialysis—A Novel Technique for Clinical Investigations".

Odland RM, Juhn SK, Hunter B "Cochlear microdialysis: A Novel Perilymph Assay Technique" Abstracts of the Midwinter Meeting, Association for Research in Otolaryngology, Feb. 1997.

Kim JY, Odland RM, Javel E, Hunter B, Juhn SK "Development of Perilymph Assay and Delivery Techniques Utilizing Microdialysis" Abstracts of the Midwinter Meeting, Association for Research in Otolaryngology, Feb. 1998.

* cited by examiner

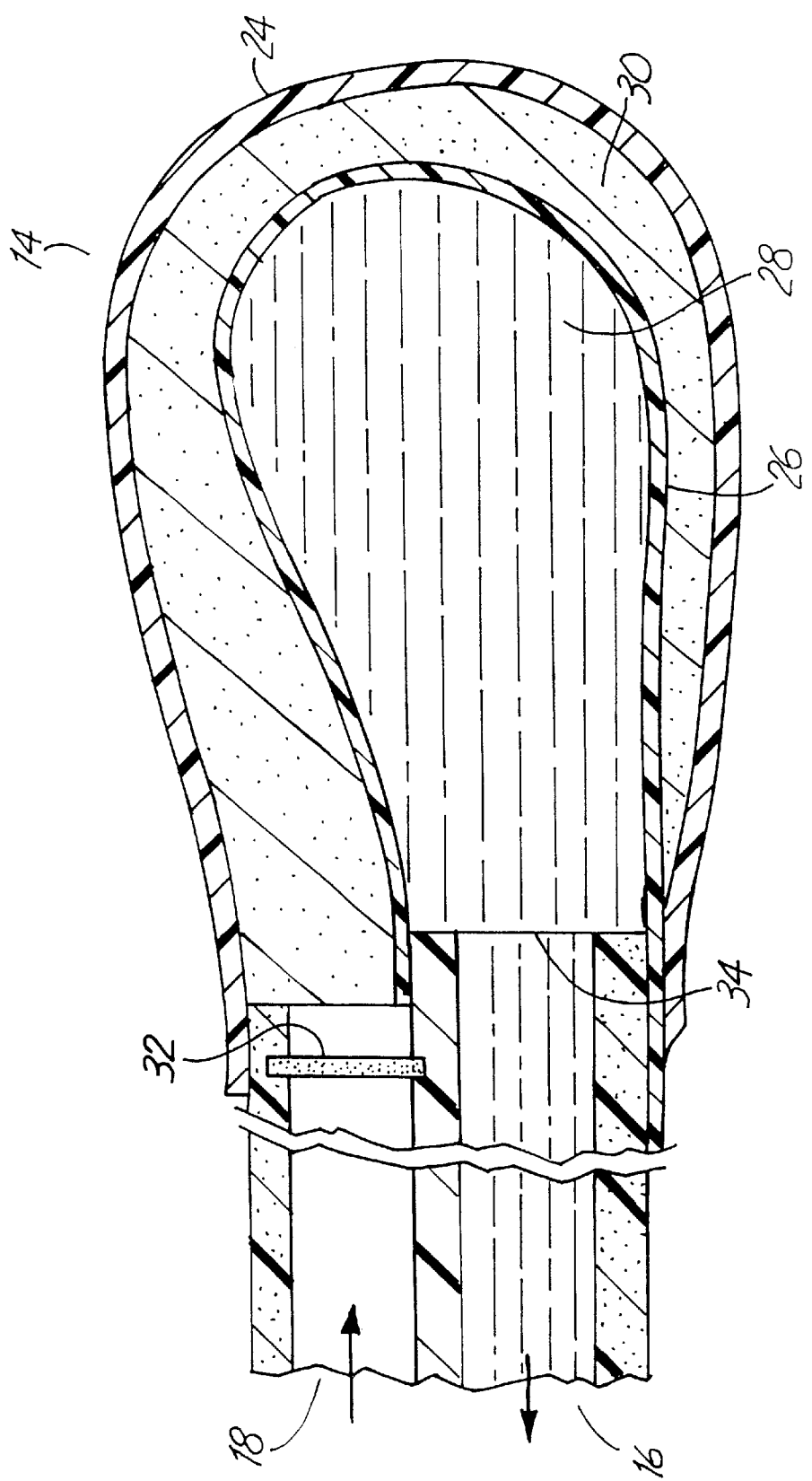

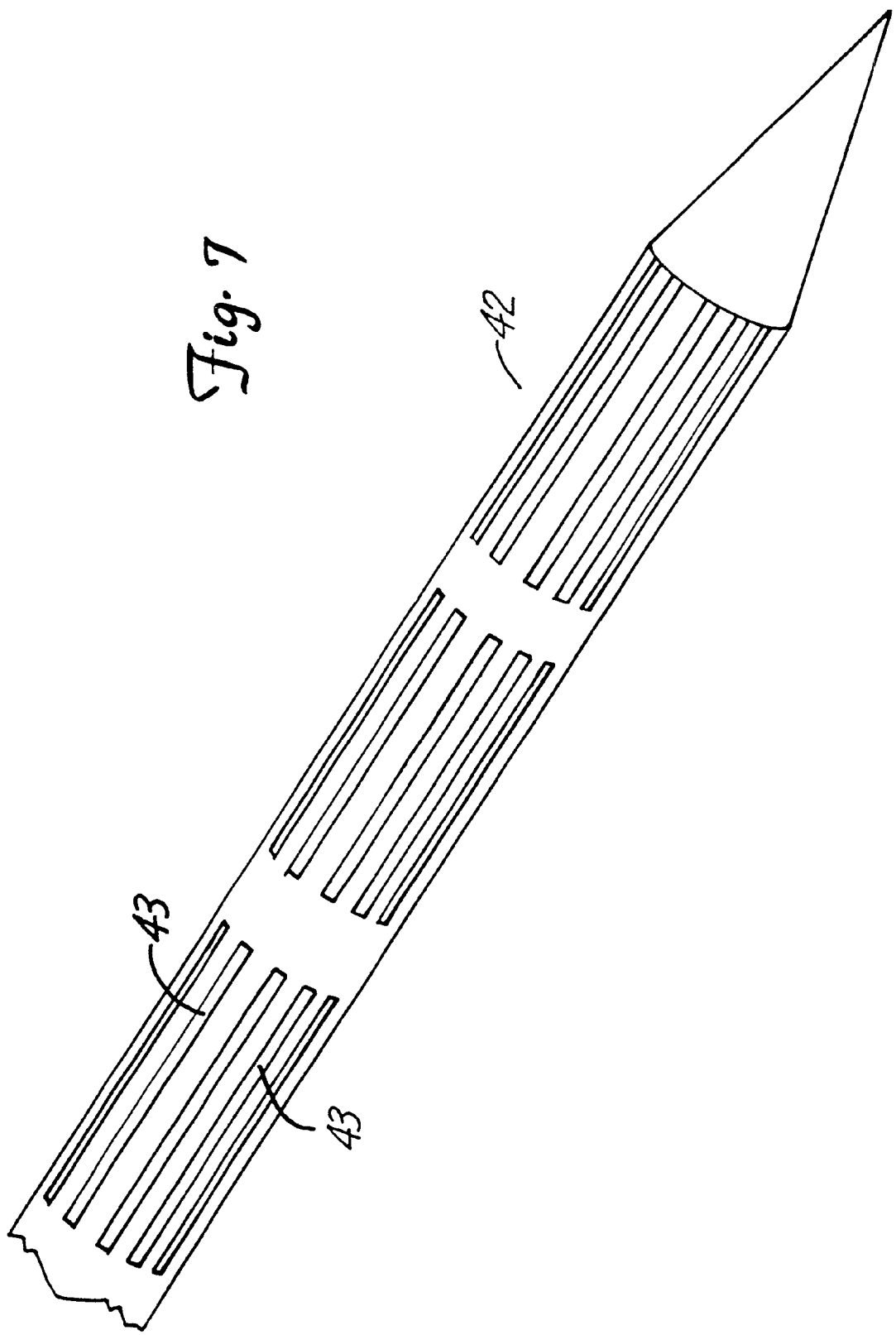

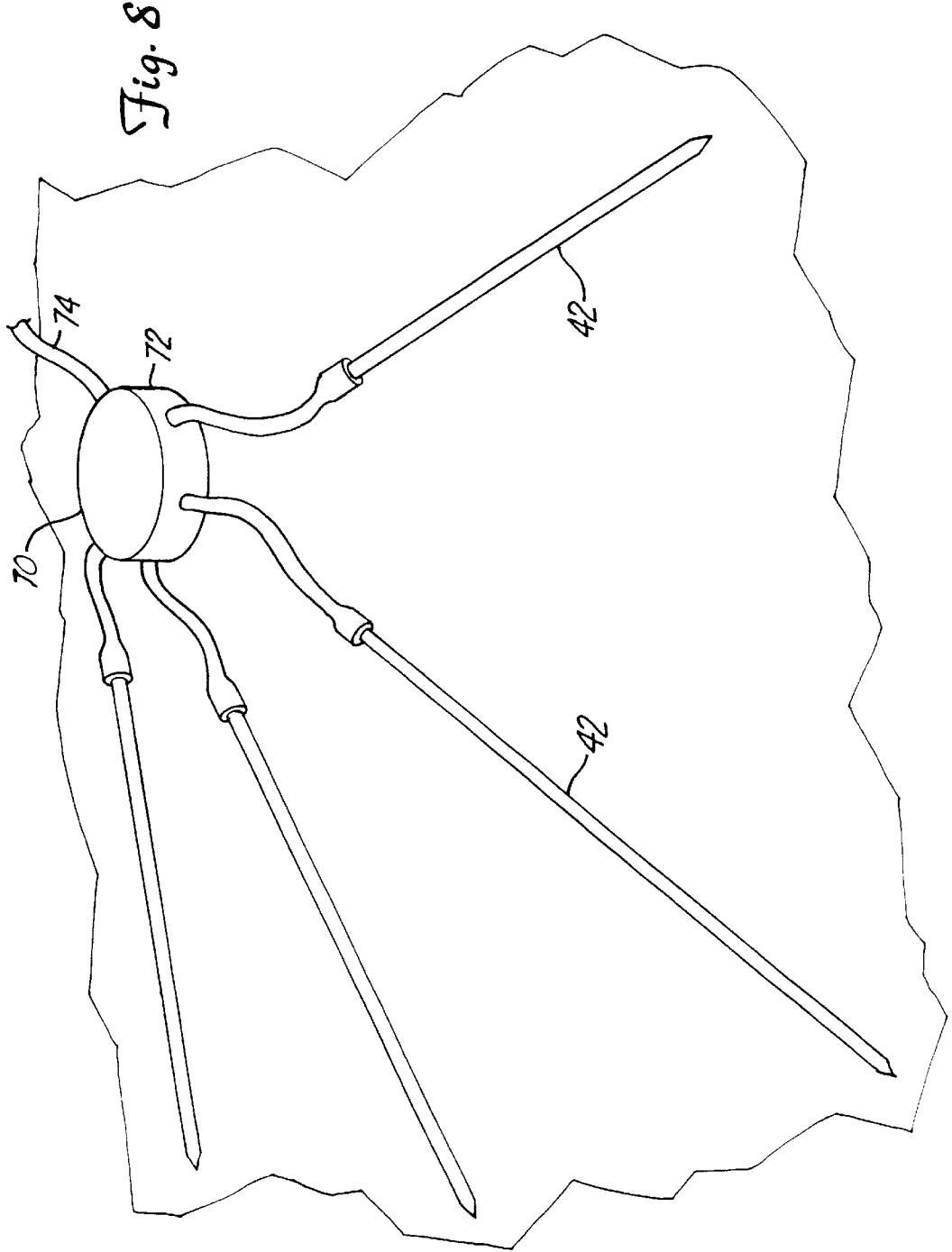

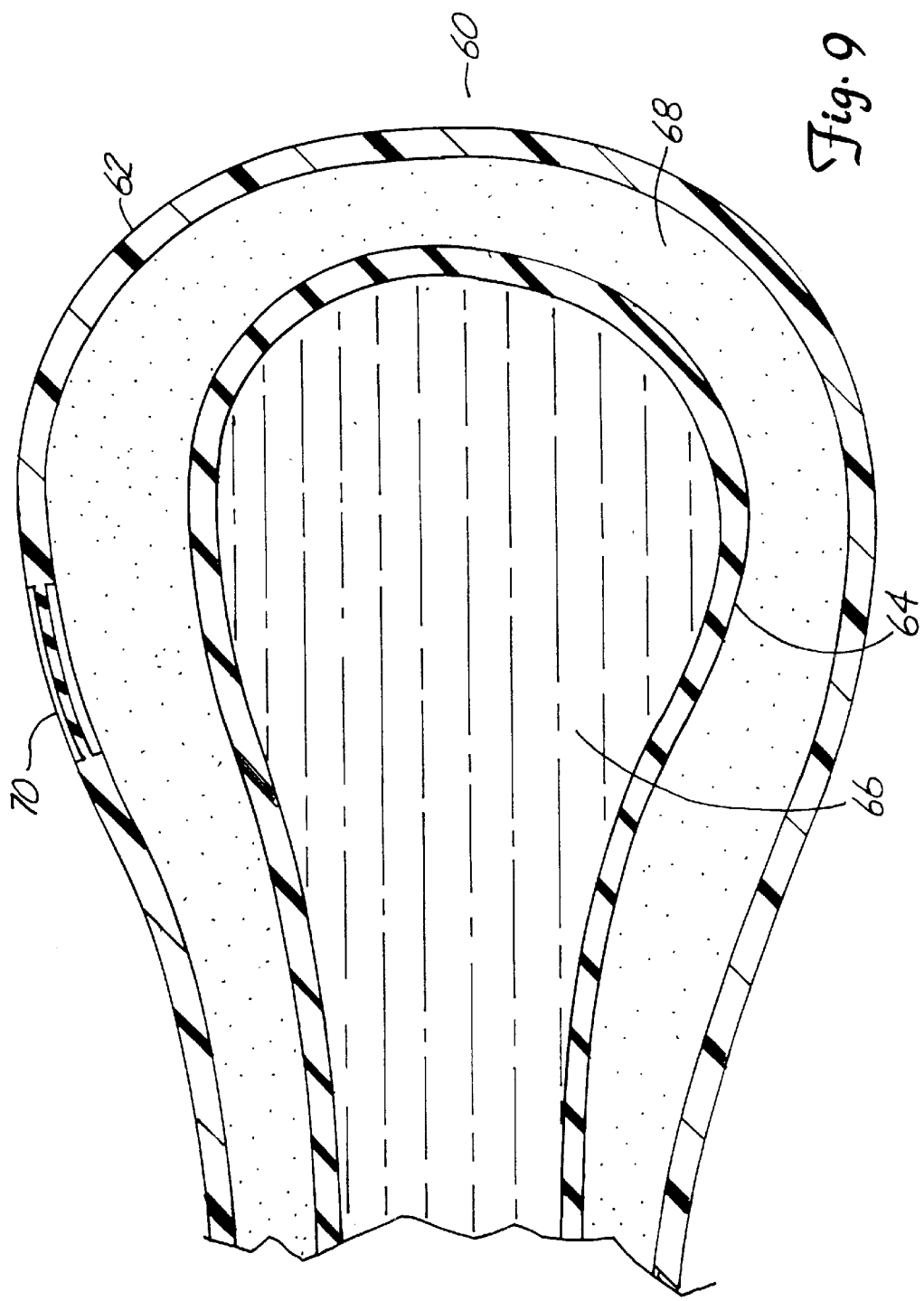

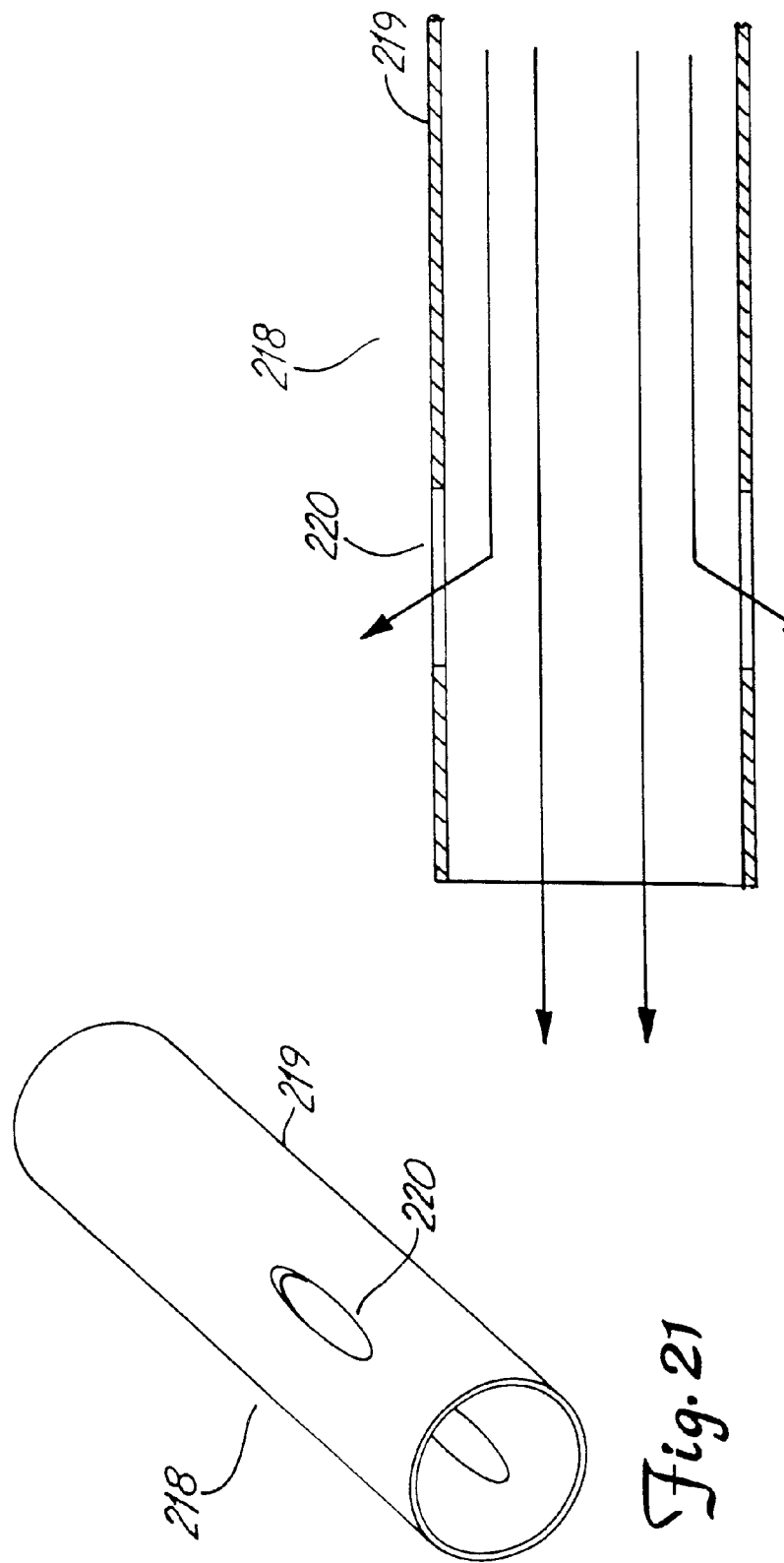

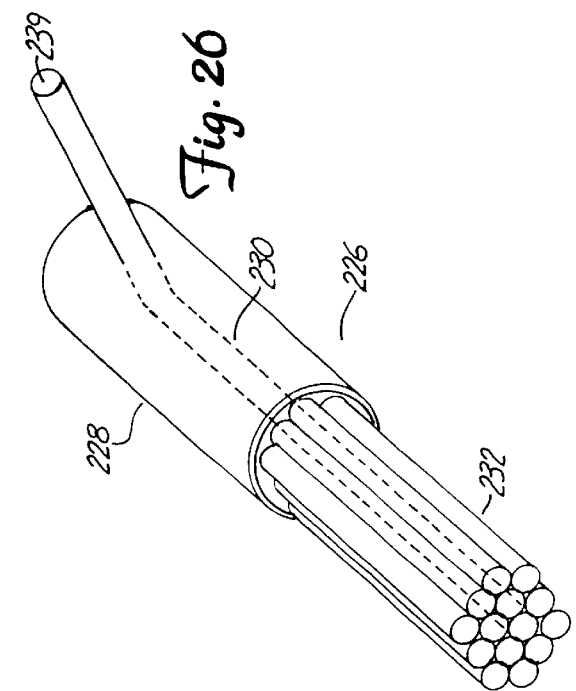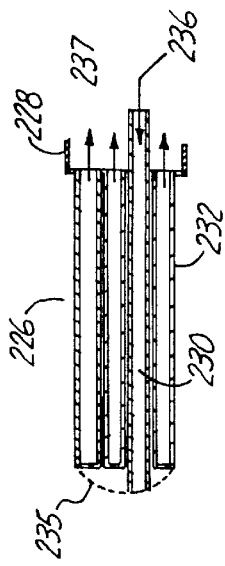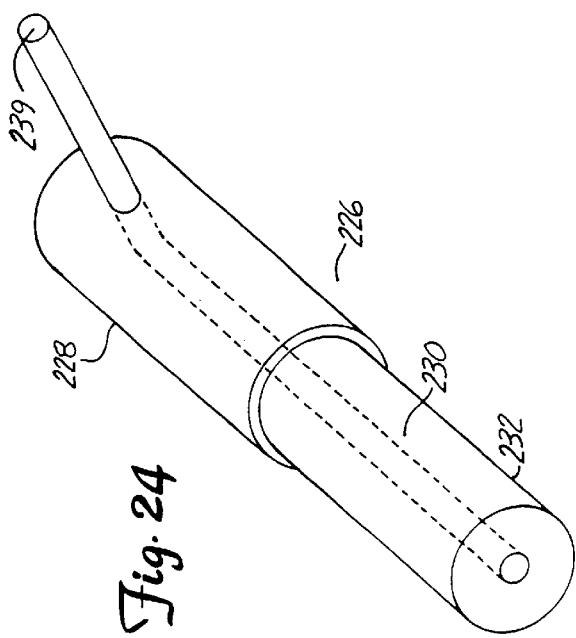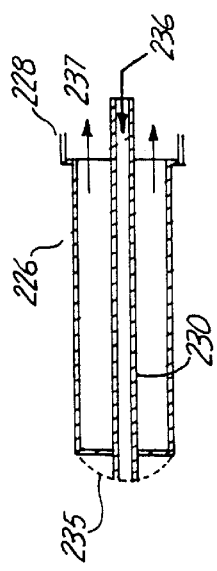

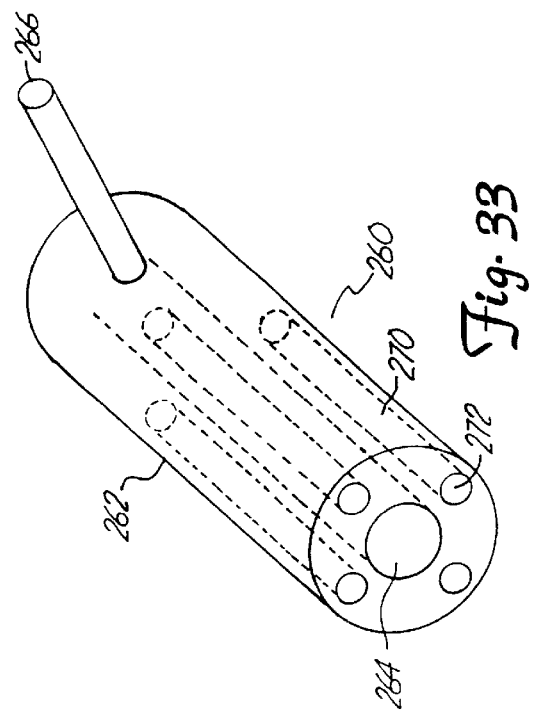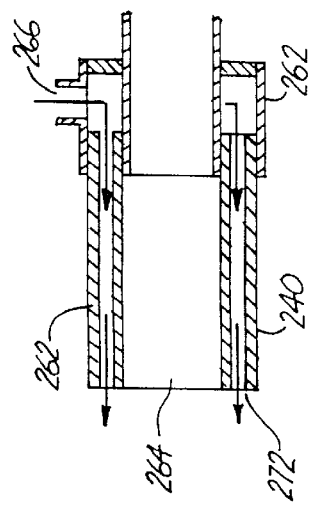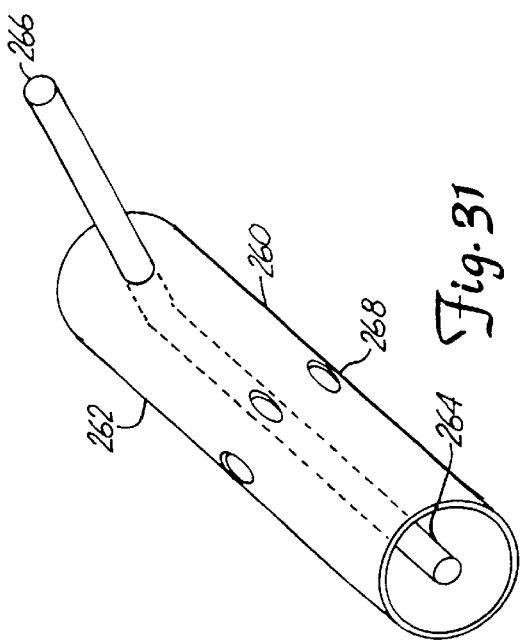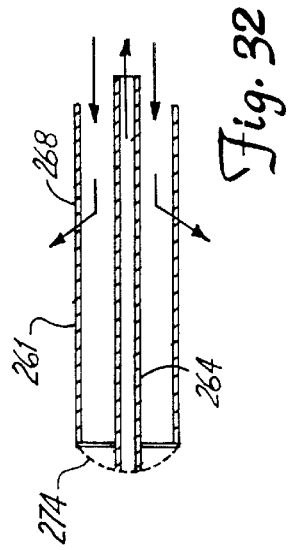

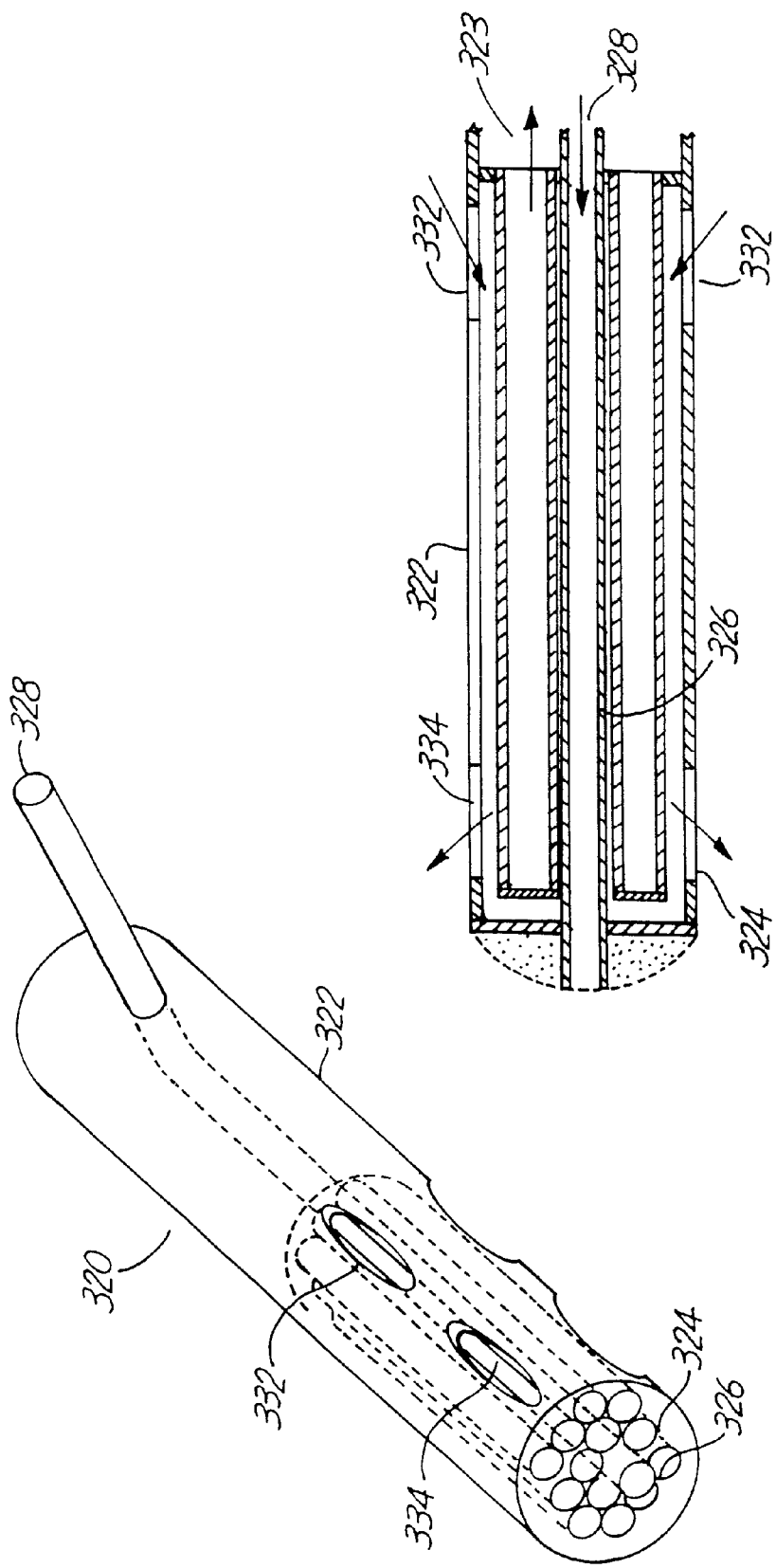

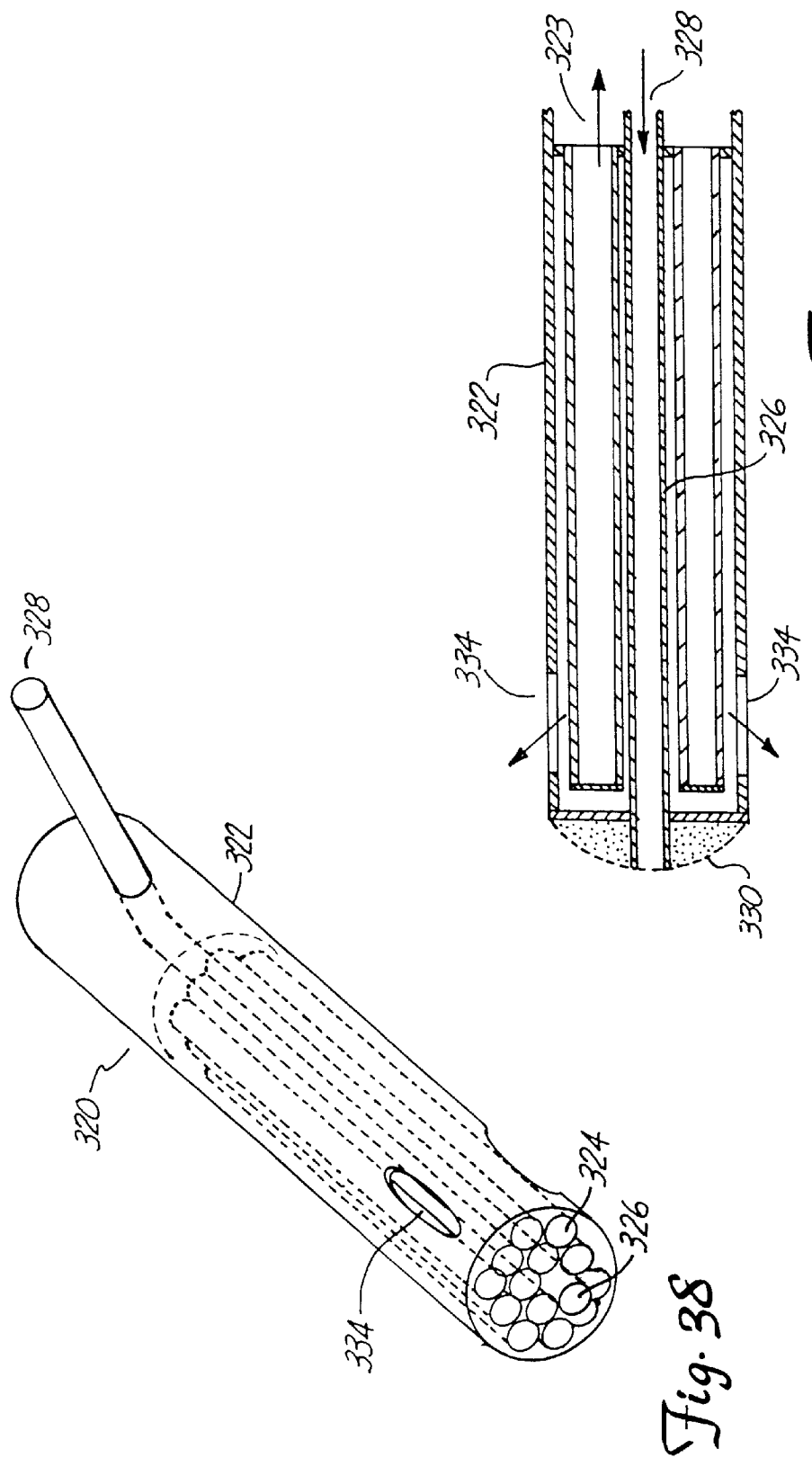

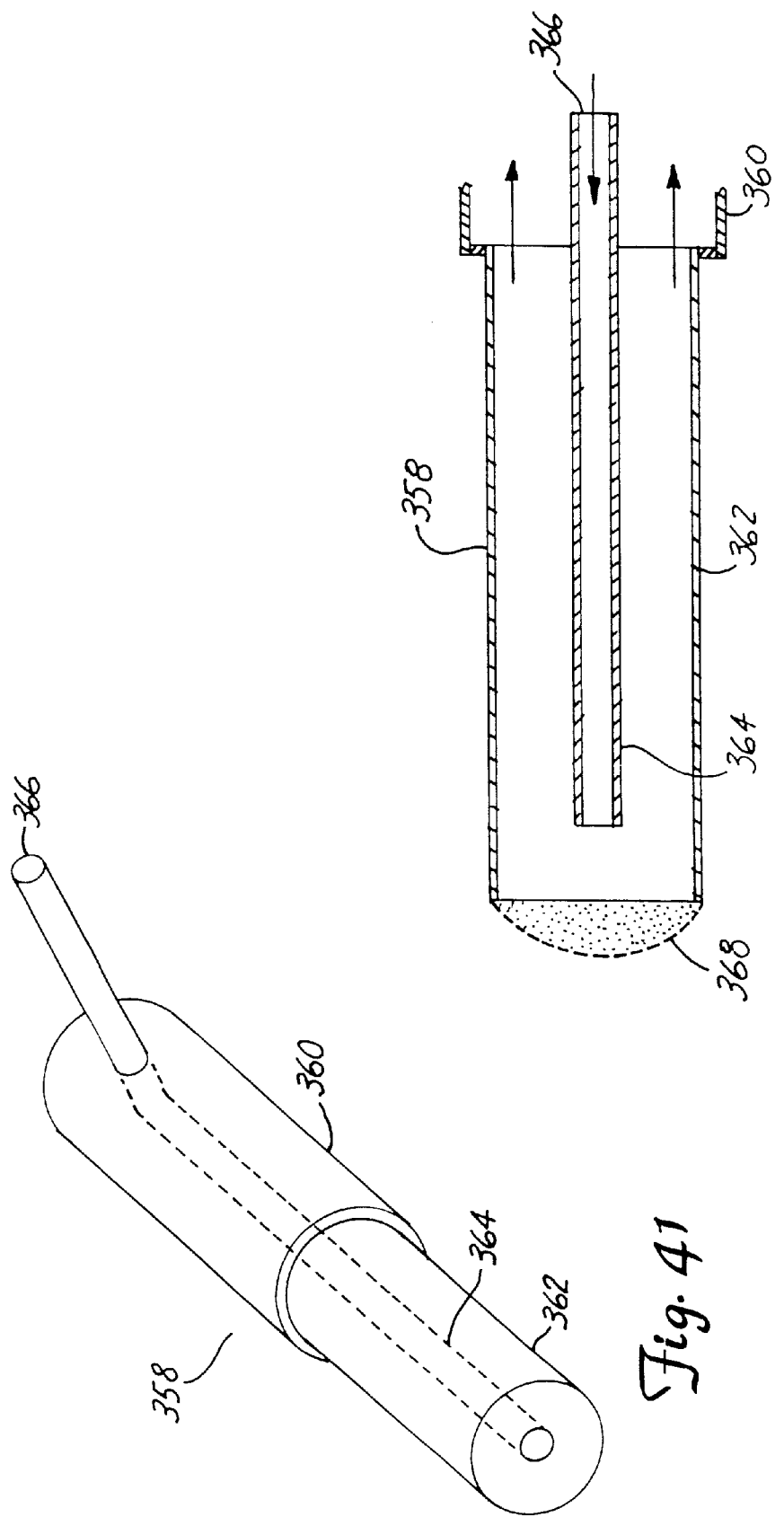

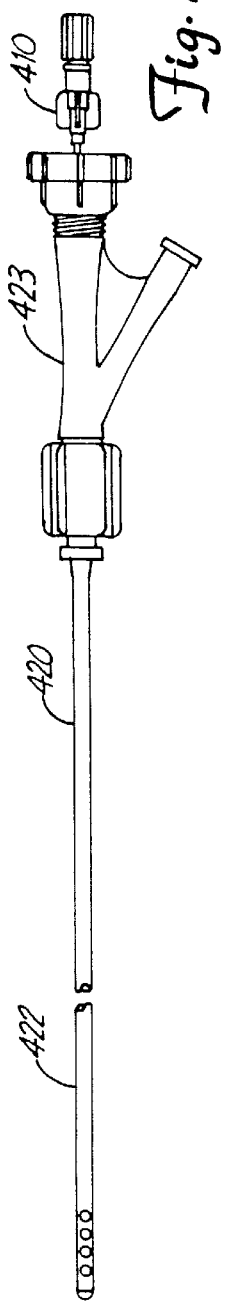
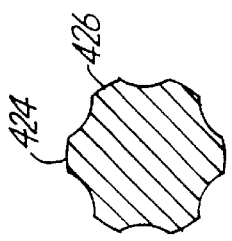
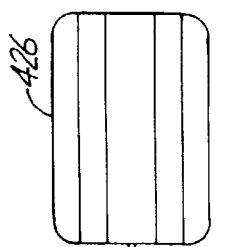
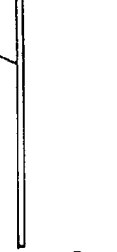
Fig. 46A
Fig. 46B
Fig. 46C
Fig. 46D
Fig. 46E

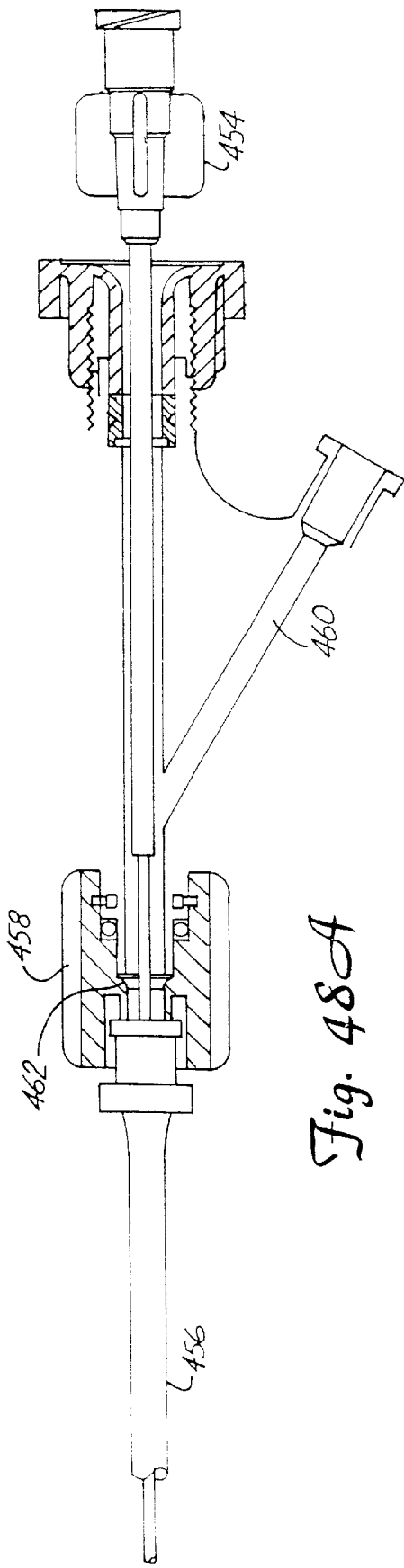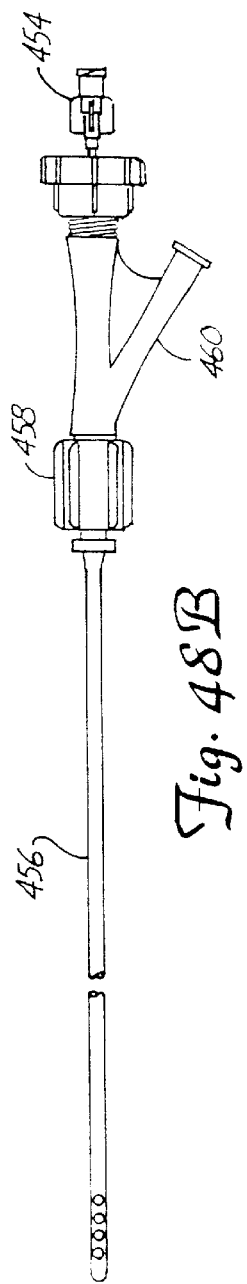
Fig. 48A
Fig. 48B

SYSTEM AND METHOD FOR SITE SPECIFIC THERAPY

CROSS REFERENCE TO RELATED APPLICATIONS

The present application is a continuation of an international patent application filed Aug. 7, 1998 and assigned Ser. No. PCT/US98/16416 which is a continuation-in-part of U.S. patent application filed Aug. 8, 1997 and assigned Ser. No. 08/908,555, now U.S. Pat. No. 6,030,358, the entire disclosure of which is incorporated herein by reference.

TECHNICAL FIELD

In one aspect, the present invention relates to methods and apparatuses for treating microcirculatory problems, including transient and reversible conditions that do no involve structural injury, as well as permanent or chronic conditions that do involve structural injury to the microcirculation. In another aspect, the invention relates to methods and apparatuses for augmenting normal microcirculation. In a related aspect, the invention relates to methods and apparatuses for treating conditions that involve osteonecrosis, compartment syndrome, edema, and skin flap survival.

In yet another aspect, the present invention relates to methods and devices for addressing cerebral edema, and to materials, such as catheters (including vetnriculosotomy catheters) and semipermeable membranes, for use in site specific treatment of tissues and tissue disorders.

BACKGROUND OF THE INVENTION

A number of clinical conditions involve (e.g., are caused by and/or themselves cause) impaired circulation, and particularly circulation within interstitial spaces and within discrete, localized tissues. Among the more vexing examples of such circulatory afflictions are osteonecrosis (e.g., avascular necrosis), compartment syndrome, and edema (and in particular, cerebral edema).

A number of conditions involve poor blood supply to the bone, leading to bone necrosis. Avascular necrosis of the proximal femur, for instance, is the disabling end result of a variety of disease processes that can affect patients of all ages. There is no treatment presently available that can predictably alter the natural history of the disorder. Clinical and radiographic progression to femoral head collapse occurs in approximately 80 percent of cases, and 50 percent undergo total hip replacement within three years. Numerous techniques have been attempted aimed at promoting the early revascularization of the femoral head, with the goal of reversing the usual process of joint deterioration. These approaches include muscle pedicle transfer and vascularized bone grafts.

Other methods, including bone remodeling and fracture repair are. similar at the cellular level, and involve the coordinated delivery of a variety of cellular elements such as growth factors, such as transforming growth factor beta (TGF-beta), fibroblast growth factor (FGF) and bone morphogenetic protein. Several technical barriers to the treatment of AVN of the femoral head and neck include the limited blood supply of the site, difficult surgical access, and the accelerated progression of the disease due to biomechanical demands of walking on the hip joint.

Acute compartment; syndrome generally involves impaired circulation within an enclosed fascial space, leading to increased tissue pressure and necrosis of muscle and nerves. The soft tissue of the lower leg is contained within four compartments, each bounded by heavy fascia—the anterior, lateral, superficial posterior, and deep posterior compartments. The anterior compartment holds the major structures for ankle dorsiflexion and foot and extension. Direct trauma, ischemia, or excessive, unaccustomed exercise can result in hemorrhage and swelling inside the anterior compartment. This swelling will increase pressure on the nerves, veins and arteries inside the compartment. Without arterial circulation, muscle cells will die. In addition, the prolonged compression of nerves can destroy their ability to function.

The neurovascular compression continues to worsen in the following symptoms: weakness or inability to dorsiflex the foot or extend the great toe, decreased ability of the peroneal tendon to evert the foot, and marked itching or prickling sensations in the web between the first and second toe or over the entire dorsal area of the foot. These symptoms must be identified quickly, since misdiagnosis can lead to permanent neuromuscular damage and physical disability.

Diagnosis involves clinical symptoms such as pain and swelling, and signs such as tense compartment pain on passive stretching, parathesia and decreased pulse, and increases in intracompartmental pressure. Once diagnosed, the injury requires immediate decompression through surgical release of the fascia covering the area. Others suggest treatment means include the use of a sympathetic blockade, hyperbaric oxygen therapy, and treatment with mannitol and/or alloperinol.

The characteristics of acute tissue edema are well known, and the condition continues to be a clinical problem, particularly since edema can be detrimental to the tissue as a result of disruption of the microcirculation. Tissue swelling results in increased diffusion distances, which in turn decreases interstitial nutrient delivery. Irreversible disruption of the microcirculatory system can occur as a result of unresolved acute injury. Resolution of tissue edema is problematic since natural mechanisms by which edema resolves are also affected by the edema. Edema compresses venules and lymphatic vessels, and inflammation makes lymphatic vessels hyperpermeable. Pharmacologic treatment is often not effective since blood borne agents have difficulty reaching their target tissue.

Cerebral edema (also known as brain swelling), includes vasogenic cerebral edema (most common form of edema) which manifests itself in the form of increased permeability of small vessels (breakdown of blood-brain barrier) and the escape of proteins and fluids into extracellular space, especially of white matter. Other forms of cerebral edema include cytotoxic cerebral edema (cellular brain edema) and interstitial edema.

Cerebral edema can be caused by ischemia, loss of oxygen, or focal disruption or loss of blood supply such as stroke. In the case of stroke, the specific area must be treated early to prevent further damage. The diagnosis of cerebral edema is based on changes in mental status, imaging, and measurement of intracranial pressure. Conventional treatment of cerebral edema is controversial. Some practicioners insist on keeping the blood pressure high to overcome high intracranial pressure, while others keep the blood pressure low in the hopes of limiting intracranial pressure. Opening the skull generally cannot be done to relieve pressure, because the brain tissue would herniate out the opening causing significant tissue damage. Giving intravenous treatments is also not effective because the bra in microcirculation is disrupted so deilivery to the brain is impaired.

Neurologic damage initiated by traumatic brain injury (TBI) continues to evolve over a period of hours to days following injury, due to deleterious delayed or secondary insults. The formation of cerebral edema, which, in turn, can lead to elevated intracranial pressure (ICP), is one of the most prevalent secondary insults serving to increase patient morbidity and mortality after TBI. ICP rises rapidly with the addition of a small intracranial fluid volume, due to the rigid and relatively inflexible nature of the skull. Complicating factors include relative noncompressability and constant volumes of brain tissue, blood, and cerebrospinal fluid (CSF) within the craniospinal intradural space. Brain swelling leading to dangerously elevated ICP develops in 40–50% of TBI patients with a Glasgow Coma Scale (GCS) of 8 or less, and higher ICP levels have been repeatedly shown to lead to poor prognosis or outcome.

Monitoring of ICP is considered appropriate for all patients with severe TBI. While the placement of an ICP monitor is invasive, the benefits of ICP monitoring are felt to offset this factor, carry a relatively small risk of complications (e.g., infection, hemorrhage, malfunction, obstruction or malposition), and rarely result in increased patient morbidity. Percutaneous devices (e.g., ventriculostomy catheters) for use in monitoring ICP monitoring are commercially available in a variety of styles and from a number of sources. Such devices are commonly placed within the cerebral ventricles, where they enable accurate and reliable monitoring of ventricular pressure and can be used for the therapeutic convective drainage of CSF.

CSF drainage is described as a potentially effective method of lowering ICP, particularly when ventricular size has not been compromised. CSF drainage typically requires penetration of the brain parenchyma with a ventricular catheter. A variety of ventricular catheters are available for such purposes, e.g., the "MoniTorr" product available from CNS, Inc. As fluid is removed, however, brain swelling often progresses to the point where the ventricular system is compressed and the ability to drain CSF can be compromised. This may be exacerbated by overdrainage, leading to the ventricular walls or the choroid plexus actually collapsing in a manner that occludes the orifices of the catheter.

The therapeutic efficacy of convective CSF drainage by conventional ventriculostomy catheters, therefore, is limited. It has been shown that CSF can be removed from the ventricles in a manner that reduces the overall intracranial volume, and thus pressure. The fluid, however, is removed from the ventricle, not from the edematous brain tissue. Once the ventricular fluid has been removed, there is typically no further reduction in ICP. Also, ventriculostomy catheters can become occluded with tissue debris and clots during convective fluid removal.

In addition to the occasional therapeutic drainage of CSF via ventricular catheters there are three primary medical treatment strategies used in attempts to control cerebral edema elevated ICP in patients with severe TBI. As briefly outlined below, it can be seen that each of these therapeutic strategies is a "double-edged sword" since each treatment is typically associated with potential adverse consequences and each has limited efficacy.

Hyperventilation: Prophylactic hyperventilation of TBI patients is currently questioned since it has been reported to worsen outcomes, does not consistently reduce ICP, and may cause loss of autoregulation and potentiate secondary ischemia due to its actions on reducing cerebral blood flow.

Mannitol: This osmotic diuretic is currently the most widely used, and probably the safest, treatment for short-term control of elevated ICP in patients with TBI. Although it has become the cornerstone for control of elevated ICP after severe TBI, mannitol administration is not without risks. Careful monitoring and maintenance of serum osmolarity below 320 mOsm is needed to reduce the risk of acute renal failure, and the latter risk is potentiated in patients with sepsis or preexisting renal disease. Although the use of mannitol affects osmolarity within the site, this approach is not site-specific, rather, it is systemically administered. Since this approach is also chemically based, rather than device based, it does not employ a device that is itself provides an osmotic barrier.

Barbiturates: Prophylactic barbiturate therapy is currently discouraged, due to variable and unpredictable positive effects on ICP. Barbiturate therapy is now typically used only in hemodynamically stable patients with intracranial hypertension/elevated ICP that is refractory to all other therapeutic interventions.

To date, osmotic fluid shifts in the course of TBI has received relatively little attention in the literature. Recent animal studies include one regarding CSF osmolality and the other regarding brain tissue osmolality (See C. Onal, et al., Acta Neurochir (Wien) 139:661–669 (1997). CSF osmolality was found to increase after a focal freeze injury in rats. CSF osmolality was found to increase from 277 mmol/kg to 348 mmol/kg at six hours after injury. CSF osmolality returned to 270 mmol/kg by 24 hours after injury. Interestingly, cerebral water content also increase at six hours, but remained elevated at 24 hours. Blood-brain barrier permeability also increased markedly at six hours and improved but remained elevated at 24 hours. Investigators in this study then went on to give intraventricular albumin to reduce the edema.

In the brain tissue study by Mori et al. J. Neurotrama 15:30 (1998), the osmolality was found to increase after cerebral contusion in a rat model. They found normal brain tissue osmolality to be 310 mmol/kg. Thirty minutes after injury, the tissue osmolality increased to 367 mmol/kg, and further increased to 402 mmol/kg at six hours. The investigators also compared ion concentration to total osmolality. On a separate topic, Janese (U.S. Pat. No. 4,904,237) describe the manner in which cerebral edema (i.e. water accumulation in brain tissue) constitutes one of the most severe and life threatening situations that occurs after traumatic brain injury (TBI) in humans. While edema can be controlled in many patients by the use of drug treatments, there are many patients for whom such treatment is not effective.

On a separate subject, Kanthan et al., J. Neuroscience Meth. 60:151–155 (1995), describe a method of in vivo microdialysis of the human brain, which method involves a "closed" technique in which a microdialysis probe and sheath are passed through a Codman bolt. Dialysate is withdrawn for periodic analysis. Similarly, Lehman et al., Acta Neurochir.[Suppl.], 67:66–69 (1996), describe a microdialysis probe for minimally invasive measurements of various products and metabolites in the brain. A number of other references describe various aspects and observations regarding the osmolar nature of brain fluids. See, for instance, Hossman, pp. 219–227 in "Dynamics of Brain Edema", Pappius, et al., eds. (1976); Hatashita, et al., pp. 969–974 in "Intracranial Pressure VII", Hoff et al; eds.; and Hoff et al., pp 295–301 in "Outflow of Cerebrospinal Fluid" (1989).

Yet other medical devices have been described which employ semipermeable membranes adapted to be implanted on a transitory basis, such as those presently used for "intracerebral microdialysis" in order to monitor rapid, ongoing chemical changes in the interstitial fluid (ISF). Such devices have been described as being potentially useful for examining neurochemical changes in the brains of patients with neurological disorders. Although analysis of brain ISF in this manner is still considered an invasive procedure, investigators have now demonstrated efficacy and safety of the technique in clinical situations. It would appear that several clinical research centers have begun using intracerebral microdialysis for monitoring the ISF within the past several years, and such monitoring has been employed in patients with TBI. To date, however, Applicant is unaware of any description of the use of such dialysis techniques or apparatuses in the treatment of cerebral edema or ICP.

In the course of inserting microdialysis probes into brain parenchyma, in order to monitor neurochemical alterations in patients, it has been found that there is minimal trauma to brain tissue and that complications are extremely rare. However, most, if not all, current microdialysis procedures rely on the slow, pump-driven infusion of dialysis fluid which travels through inlet lines past the dialysis fiber and then through outlet lines to enable collection of the dialysate. The dialysis probes used in such procedures are generally of rigid construction, to enable passage into brain tissue. The procedures themselves typically result in only a small percent "recovery" of neurochemicals or other molecular entities, for assay, since the procedures rely on the diffusion of chemicals from ISF to the dialysis fluid.

Investigators also commonly insert apparatuses into the brain ventricles, for a variety of reasons. Osterholm, for instance (U.S. Pat. Nos. 4,378,797, 4,445,500, 4,445,886, 4,758,431, and 4,840,617) describes a cerebral catheterization apparatus for delivering oxygenated nutrient to of from the CSF of a patient suspected of suffering from ischemia (stroke). The apparatus includes a catheter for providing an oxygenated nutrient, in the form of a synthetic CSF, to the ventricle. In view of the need to deliver (e.g., perfuse) such a nutrient to the brain quickly after stroke, this particular patent is directed toward a catheterization apparatus intended to be used by paramedics and emergency room personnel to insert a cerebral perfusion catheter into the left and right lateral brain ventricles of the patient.

The use of skin flaps has gained increased acceptance and use in the course of reconstructive and other forms of surgery. These techniques, however, continue to be plagued by problems having to do with survival of the skin flaps, which in turn, is believed to rely, at least in part, on efficient revascularization of the site. A number of approaches have been considered or evaluated for improving skin flap survival. See, for instance, Waters, et al., which provides a comparative analysis of the ability of five classes of pharmacological agents to augment skin flap survival in various models and species, in an attempt to standardize skin flap research. (Annals of Plastic Surgery. 23(2):117–22, 1989 August).

On a separate subject, the development of methods and apparatuses for tissue microdialysis began at least as early as the early 1960's with the work of Gaddum and others. To date, microdialysis has been used primarily, and with increasing frequency, in the neurosciences, as a means of assaying the interstitial space. In such applications the delivered solution is typically isotonic in order to avoid producing an osmotic gradient and resulting fluid shift. See, generally, Lonroth, et al., *J. Intern. Med.,* 1990 May;227 (5):295–300, "Microdialysis—A Novel Technique for Clinical Investigations"; Johansen, et al. *Pharmacotherapy* 1997 May;17(3):464–481, "The Use of Microdialysis in Pharmacokinetics and Pharmacodynamics"; and Cimmino et al., *Diabetes Metab.* 1997 April; 23(2):164–170, "Tissue Microdialysis: Practical and Theoretical Aspects".

A limited number of references describe the use of microdialysis to deliver substances such at therapeutic agents. Lehmann et al., *Acta Neurochir. Suppl.,* 67:66–69 (1996), describe a microdialysis probe adapted for entry into the parenchyma in order to measure various analytes, the probe being described as useful for possible "therapeutic applications". Similarly, Yadid, et al., *Am. J. Physiol.* 265:R1205–R1211 (1993), describe a modified microdialysis probe for sampling extracelluar fluid and delivering drugs for use in studying the local release and metabolism of neurotransmitters in vivo.

A limited number of other references describe the use of microdialysis to remove interstitial fluid for diagnostic purposes, as described, for instance in Linhares et al., Anal. Chem. 64:2831–2835 (1992). Recent articles have described the use of a hollow fiber catheter to perfuse the catheter with a hypertonic solution in order to intentionally produce a fluid shift and reduce tissue edema. See, for instance, Odland, et al. "Reduction of Tissue Edema by Microdialysis" Arch. Otolaryngol. Head Neck Surg, Vol. 121, pp. 662–666 (1995), which describes the use of a test device having catheters connected by afferent segments of tubing to an infusion pump providing a hypertonic solution of inulin in saline.

To Applicant's knowledge, however, there is no present teaching, let alone clinically acceptable approach for the application of tissue microdialysis in site specific therapy, or in particular, a microdialysis apparatus useful for prolonged periods, difficult sites, and in clinical settings.

In turn, current therapies for treating elevated ICP and cerebral edema, in humans with severe traumatic brain injury, have limited efficacy and continue to be associated with serious risks (particularly with prolonged use). In some patients, cerebral edema simply remains untreatable or nonresponsive to treatment. What is clearly needed are methods and related devices and systems for use in relieving ICP, particularly in a manner that optimizes the ability to employ conventional techniques and apparatuses, in new and different combinations, in order to improve overall patient outcome.

SUMMARY OF THE INVENTION

The present invention provides a method and related system for use in site specific therapy of a tissue site. In a preferred embodiment, the invention provides a system comprises one or more catheters adapted to be positioned within the tissue site and a delivery/recovery mechanism for employing the catheter(s) to control the movement of bulk fluids and/or active fluid components within or between tissue portions or adjacent tissues in a manner that achieves a therapeutic effect. More preferably, the tissue site comprises an anatomic site within the body containing one or more fluids in latent or actual fluid communication, the fluids, in turn, each containing one or more active fluid components selected from the group consisting of biologically active molecules and osmotically active molecules.

In a corresponding method, the fluid movement can be used to affect the osmolar nature of a remote first fluid by altering the osmolar nature of a second fluid in osmotic ommunication with the first fluid, and/or it can be used to effect the movement of biologically active molecules between adjacent healthy and diseased portions of the same tissue. In a particularly preferred embodiment, the catheter (s) comprise one or more semipermeable microcatheters, adapted to effect the movement of fluid or fluid components within the tissue site by microdialysis within the tissue site.

The term "tissue site", as used in this respect, will refer to an anatomic location or organ within the body containing one or more fluids in latent or actual fluid communication, the fluids, in turn, each containing one or more components such as biologically. or osmotically active molecules. The method and system involve the deliberate and controlled, and optionally selective, movement of fluids and/or the active fluid components, in a direct or indirect fashion, within or between tissue portions or adjacent tissues. Such fluid movement can be used, for instance, to affect the osmolar nature of a remote first fluid by altering the osmolar nature of a second fluid in osmotic communication with the first. Such fluid movement can also be used, for instance, to effect the movement of agents between adjacent healthy and diseased portions of the same tissue.

The catheter assemblies, in turn, can be provided in any suitable form, including the use of one or more individual catheters. In certain applications one or more of the catheters within an assembly are preferably provided in the form of semipermeable microcatheters, which in turn are adapted to permit dialysis to be performed within the tissue site.

In one embodiment, therefore, the present application provides an apparatus and method for performing site specific microtherapy, a preferred embodiment of the apparatus comprising one or more catheters (optionally including semipermeable microcatheters) dimensioned to be positioned within a tissue site, the catheters comprising one or more surfaces for delivering fluid to the tissue site and one or more surfaces for removing fluid from the tissue site, the catheters being adapted for fluid communication with a pump reservoir or other mechanism for the delivery and/or recovery of fluid or fluid components. Optionally, and preferably, the apparatus includes such a pump reservoir as a component part.

In a further preferred embodiment, the apparatus provides an outflow circuit for delivering fluid (and/or solutes) to the tissue site and an inflow circuit for removing fluid (and/or solutes) from the tissue site, in combination with a manifold and associated pump system for controlling and directing the flow of fluid within the catheter(s). In one such embodiment, the outflow and inflow circuits each employ one or more catheters to recover and deliver fluid (optionally containing solutes such as biological agents) between sites of healthy and diseased or injured tissue. In another preferred embodiment, the outflow and inflow circuits are provided in the form of separate and substantially parallel recovery and delivery catheters, where they cooperate to provide convective interstitial flow within the tissue site.

Applicant has found that the distribution of fluids within or between portions of a tissue, including the delivery of fluids and any solutes contained therein, can be significantly enhanced by the present apparatus, which can serve to artificially replicate the hydrostatic forces and/or solute delivery characteristics of the microcirculatory system. In such a preferred embodiment the present invention employs microfibril technology to deliver and/or remove fluid, solutes, or specific agents to and/or from a tissue space. In particular, the apparatus permits the infusion of fluids and/or therapeutic agents, and the corresponding removal of tissue fluids and/or biological factors, with the optional ability to simultaneously monitor physiologic parameters. In turn, the invention further provides a commercially viable in vitro tissue engineering technique based on the principle of microdialysis.

The apparatus and method of the present invention can be used for a variety of purposes in the course of providing artificial microcirculation, including for instance, for replicating, repairing, or augmenting circulation inside or outside of the body. In turn, the present invention can be used for a variety of applications, including to treat reperfusion injury or deliver toxic agents directly to a tissue site (inter alia, to avoid systemic toxicity), and for the delivery of poorly diffusible molecules to the interstitum. In particularly preferred embodiments, the apparatus and method of this invention are used to treat clinical conditions that include cerebral edema, stroke, osteoporosis, ischemic osteonecrosis (e.g.; avascular necrosis ("AVN") of the femoral head), compartment syndrome, skin flap failure, reperfusion injury, and inflammation in fixed spaces. The apparatus and method of the invention can also be used for the preparation of bone and soft tissue grafts.

A preferred apparatus employs a hydrostatic or osmotic gradient, established by the use of one or more suitably placed and configured catheters, to affect tissue metabolism or fluid flow in large or small sites. The microdialysis system solves the problem of treating focal tissue sites when a) there is inadequate local tissue microcirculatory system to perfuse the tissues, b) systemic toxicity of the agent is a factor, c) the agents to be delivered or removed are large, and d) any combination of the above. The apparatus can be provided as a single catheter, employing either diffusional, osmolar, or hydrostatic forces, or a plurality of catheters having one or more dedicated delivery and recovery catheters, or portions thereof, that employ similar forces.

In another preferred embodiment, the present invention provides a system, including a catheter apparatus, and related method for performing site-specific therapy at a tissue site having first and second fluids separated by an osmotic barrier, wherein the tissue site exhibits edema brought about by accumulation of the first fluid. The system comprises an apparatus that comprises:

a) one or more catheters adapted to be positioned in fluid communication with the second fluid of the tissue site, and b) a fluid delivery/recovery mechanism for delivering and/or recovering fluid components (e.g., a component containing water and permeant solutes or the impermeant solute component), to and/or from the tissue site in a manner that affects the osmolarity of the first and/or second fluids in order to reduce edema.

In a particularly preferred embodiment, the system and related method are adapted for treating ICP associated with cerebral edema, and the system comprises an apparatus that comprises:

a) one or more catheters adapted to be positioned in fluid communication with the cerebrospinal fluid within a ventricle in the brain, and b) a fluid delivery/recovery mechanism for delivering and/or recovering fluid components to and/or from the tissue site in a manner that affects the osmolarity of either or both fluids in a manner that reduces edema.

A further preferred embodiment is adapted for situations in which the edema involves an increase in pressure brought about by the accumulation of a first fluid (interstitial and/or intracellular fluid within the brain), and the system comprises an apparatus that comprises:

a) one or more semipermeable microcatheters adapted to be positioned in fluid communication with cerebrospinal fluid within a ventricle in the brain, and b) a fluid delivery/recovery mechanism for delivering and/or recovering fluid components to and/or from the CSF in a manner that affects the osmolarity of either the CSF or corresponding brain fluids in a manner that reduces edema. In a particularly preferred embodiment, the system can be used in a method that involves either delivering impermeant (i.e., osmotically active) solutes to, or removing solute from, the CSF, in order to begin a cascade of events leading, eventually, to a reduction in edema.

A corresponding method of the present invention includes the steps of:
a) providing a system comprising an apparatus as described above,
b) positioning the apparatus within the second fluid of a tissue site exhibiting edema, and
c) employing the fluid delivery/recovery system to deliver and/or recover fluid components to and/or from the second fluid in a manner that subtstantially alters the osmolarity of the first fluid in order to reduce edema.

While not intending to be bound by theory, the present system is based, at least in part, on the Applicant's premise that certain tissue sites exhibiting edema can be viewed as two distinct fluids, having the potential for osmotic disparity between them. That disparity provides an opportunity for therapeutic intervention. The first and second fluids may, individually, be hyper- , hypo-, or isoosmolar, either with regard to each other and/or to their original, non-edema state. In edema, for instance, the first and second fluids can establish an osmotic equilibrium with respect to each other, e.g., in which there is no net flux of solvent between them, even while the volume of the first fluid remains increased, causing edema at the tissue site.

The invention, therefore, provides means for affecting that osmotic disparity in such a manner that the volume of the first fluid is decreased in order to alleviate edema. The word "affects", as used in this context, refers to any influence or control over the absolute or relative osmolar status of the first or second fluids, e.g., by affirmatively altering the osmolar nature of one or both fluids, or by maintaining both fluids static under conditions where they would have tended to change. From one perspective, the invention provides a method for altering the osmotic relationship of the two fluids in a manner that permits a desired result in the first fluid to be achieved indirectly, by altering the osmotic nature of the second fluid. The osmolar relationship between the two fluids can also be altered, or maintained static, by altering characteristics of the barrier itself (i.e., the membranes separating first fluid from the second fluid), to provide the same or similar effect. For instance, the barrier can be treated in a minimally invasive fashion (as with the delivery of surfactants, or mechanically) to change its effective molecular weight cutoff, and in turn, the definition (and therefore number) of impermeant solutes in each affected fluid.

Such a system can be used to recover the solvent component of the second fluid, that is, water and solutes that freely pass the semipermeable barrier (alternatively referred to herein as "permeant solutes" or "inactive osmoles"). This solvent component can be removed in an amount sufficient to effectively raise the concentration of remaining impermeant solutes in the second fluid. The increased impermeant solute concentration in the second fluid (e.g., ventricular CSF), in turn, causes solvent from the first fluid to cross the osmotic barrier into the second fluid. The loss of solvent from the first fluid, in turn, effectively increases the osmolarity of the remaining interstitial fluid, which in turn causes compensatory water/electrolytes to be drawn from surrounding cells in an amount sufficient to lessen the swelling (edema) in those surrounding tissues, and/or to reduce the pressure exerted by the tissue upon other tissues. The permeant component of CSF can be removed and/or permitted to drain from the ventricle by natural means, through arachnoid granulations, finally becoming absorbed in the blood.

Using rat models and similar systems Applicant has found, for instance, that there is a increase in CSF osmolarity after head trauma, which is consistent with the idea that osmotic relationships differ between the fluids following injury. Applicant has further found that microdialysis fibers, when tested in various fluid solutions (ranging from saline to artificial CSF), were indeed able to extract the solvent component in a manner that alters osmolarity. Applicant has also evaluated the use of various types of microdialysis fibers with preserved CSF from TBI patients.

In a preferred embodiment the method and system are site specific, in that they can be used to alter the osmolar relationship between fluids within a particular tissue site. The method and system are also optionally highly selective (e.g., by the selection and use of osmoles of specific sizes or concentrations).

In turn, the preferred method and system have an indirect effect, in that they can be used to achieve a result in a remote (first) fluid, for instance, by lessening its volume, and in turn, its pressure. This indirect effect can be achieved by direct contact with (and the affirmative manipulation of) a second fluid, which is directly or indirectly separated from the first fluid by an osmotic barrier. The method and system can achieve such results in any suitable manner, e.g., by altering the absolute and/or relative volumes or osmolarities of one or more fluids, and/or by simply controlling or maintaining the volumes and/or osmolarities in order to prevent further edema.

By way of example, the delivery/recovery step can involve the delivery of fluids and/or osmotic agents, to or from the first and/or second fluids. Generally, in situations where either or both fluids can be accessed within a tissue site, and where edema is due to increased volume of the first fluid, site-specific treatment options include: 1) recovering fluid from the second fluid; 2) delivering osmoles to the second fluid; 3) recovering osmoles from the first fluid; and/or 4) delivering solvent to the first fluid.

In the case of cerebral edema, however, the present invention provides apparatuses that can be used to access either of the two compartments (and in either of the two fluids) making up the tissue site, namely, parenchymal probes for accessing the first fluid and ventricular apparatuses for accessing ventricular CSF. In the latter embodiments, the method and system of the present invention, in turn, will typically involve either the removal of solvent from the second fluid or the delivery of osmoles to the second fluid. In either case, the net effect is an increase in the osmolarity of the second fluid, followed by the cascade of events described herein, including the diffusion of solvent from the first to second fluids.

BRIEF DESCRIPTION OF THE DRAWING

In the Drawing:

FIG. 3 shows an enlarged cross section of the pump reservoir of the apparatus of FIG. 1.

FIG. 5 shows a perspective view of the pump reservoir of the apparatus of FIG. 4, for use in sampling the interstitial space, while

FIG. 7 shows the delivery sheath depicted in FIG. 4, for use in placing the apparatus.

FIG. 8 shows a manifold for the recovery of interstitial fluids by the use of a plurality of delivery sheaths.

FIG. 9 shows an enlarged view of the pump reservoir for an apparatus of FIG. 4, for therapeutic applications.

FIGS. 18 and 19 show perspective and cross-sectional views, respectively, of a preferred apparatus of the present invention, while

FIGS. 21 and 22 show perspective and cross-sectional views, respectively, of an alternative preferred apparatus, while

FIGS. 24 and 25, 26 and 27, and 28 and 29 show paired perspective and cross-sectional views, respectively, of another preferred apparatus, while

FIGS. 31 through 34 show paired perspective and cross-sectional views, respectively, of another preferred apparatus, while

FIGS. 36 and 37, and 38 and 39 show paired perspective and cross-sectional views, respectively, of an alternative preferred apparatuses, while

FIGS. 41 and 42 show perspective and cross-sectional views, respectively, of another preferred apparatus, while

FIGS. 46(a–e) shows various views of a system that includes a conventional ventriculostomy catheter in combination with the microcatheter of FIG. 45.

FIGS. 48(a and b) shows various views of the system of FIG. 46 including a Y-adapter.

DETAILED DESCRIPTION

Figure 1:
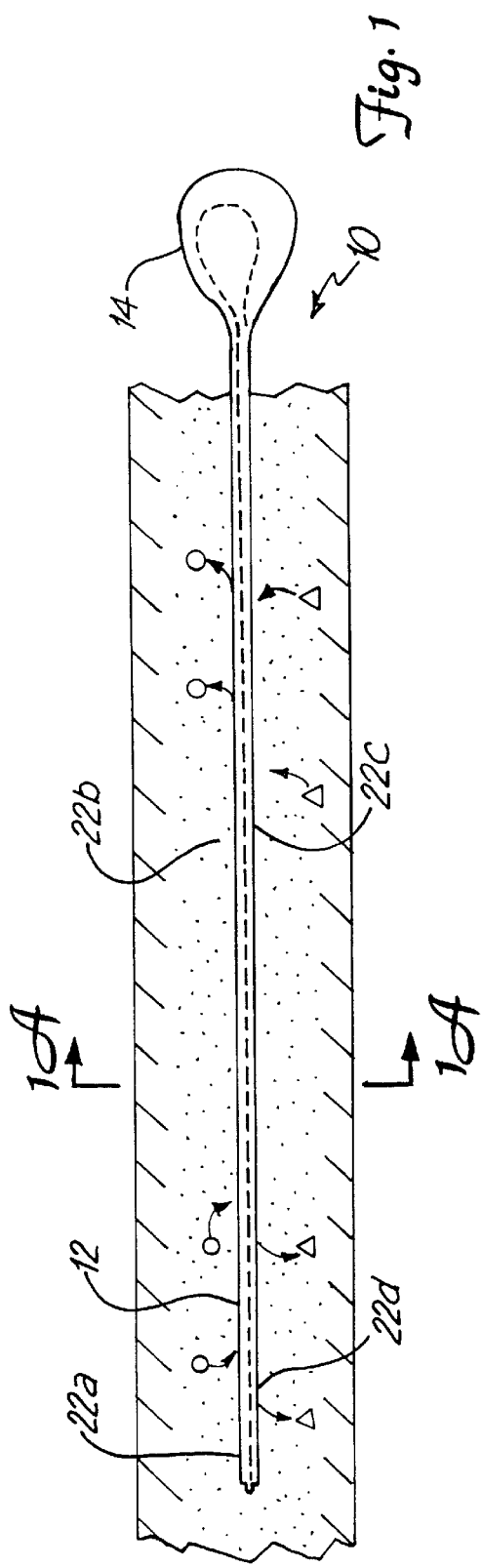
FIG. 1 shows a preferred apparatus for the treatment by transdialysis of avascular necrosis, while Figure IA shows a cross section of the apparatus.

As used herein, the following terms shall have the meanings ascribed to them below:

The word "apparatus", when applied to the present invention, will refer to a functional combination of a a fluid delivery/recovery mechanism, such as a pump reservoir and one or more catheters (e.g., microcatheters) adapted to be positioned within a tissue site and controlled by the fluid delivery recovery mechanism. The word "microcatheter", in turn, will be used to describe a capillary tube having one or more lumen and semipermeable walls or wall portions, while the term "pump reservoir" will refer to the portion(s) of an apparatus that serves to deliver and recover fluid to and from the microcatheter, and in turn to deliver fluid and/or solutes from the tissue site, whether by means of osmolar gradient, hydrostatic pressure, or diffusion, or an appropriate combination thereof. A pump reservoir will preferably have one or more reservoir compartments for holding fluids to be delivered to the catheter (including microcatheter) and one or more reservoir compartments for holding fluids recovered therefrom, in combination with a mechanism for effecting the flow of fluid therebetween.

The word "delivery" will refer to the flow of fluid and/or solutes (e.g., biomolecules) from a pump reservoir and into a lumen of a catheter (and optionally, in turn, into surrounding tissue), while "recovery" will refer to the flow of fluid and/or solutes from a lumen of a catheter (on optionally, in turn, from surrounding tissue) and back to the pump reservoir. A catheter can be used within an apparatus of this invention for a variety of purposes, including as a microexchange catheter for either delivery or removal. A microcatheter is preferably microporous, e.g., semipermeable or microperforated.

Insofar as the driving forces are concerned, the word "hydrostatic" will refer to fluid dynamics brought about by imposing a positive or negative pressure on a liquid within a catheter, as by the application of a microdialysis pump or vacuum, while "hyperosmolar" will refer to fluid dynamics brought about by the use of a solute of sufficient size and concentration within a catheter to cause osmotic flow of fluid from surrounding tissue and into, or out of, the catheter. In contrast, the word "diffusion" will refer to the spreading or intermixing of materials (fluids and/or solutes), due to molecular movement.

Those skilled in the relevant art, given the present description, will understand the manner in which any suitable combination of hydrostatic, hyperosmolar and diffusional forces can be employed to deliver and recover fluids and/or solutes using catheters in the manner provided herein. In general, the method and apparatus of this invention can be used in a site specific manner to achieve any of a number of goals, including to remove excess fluid (and thereby reduce interstitial pressure and improve microcirculation), and to deliver and/or recover agents to or from various parts of the body.

An example of an osmolar (e.g., hyperosmolar) microcatheter apparatus of this invention includes a coaxial microcatheter in which a hyperosmolar perfusate is delivered by hydrostatic (i.e., pressure) means to the distal end of a coaxial microcatheter assembly, whereupon it returns to the pump reservoir together with tissue fluid that is recovered through the semipermeable outer membrane of the assembly by osmosis. Optionally, and preferably, the hyperosmolar perfusate itself contains a sufficiently high concentration of one or more agents to allow the agent to be delivered through the semipermeable membrane and into the tissue by diffusion or other forces. Examples of the use of hydrostatic and diffusion microcatheters include, respectively, the dual catheter and transdialysis embodiments described below.

Osteonecrosis refers to the in situ death of cells within a bone segment, e.g., due to or resulting in a lack of blood flow. The circulation of the femoral head, for instance, is supplied by vessels that pass in a retrograde fashion within the femoral neck. This makes the femoral head particularly vulnerable to AVN from a variety of process that interrupt this blood supply. In infants and children AVN is seen as a consequence of trauma or the treatment of developmental hip dysplasia or slipped capital femoral epiphysis. Spontaneous AVN of the femoral head in children is known as Legg-Calve-Perthes disease. In adults, AVN occurs as the result of trauma or is associated with a variety of disorders including hematologic or autoimmune diseases, corticosteroid therapy, coagulation disorder, alcoholism, barotrauma, and disorders of lipid metabolism.

Figure 2:
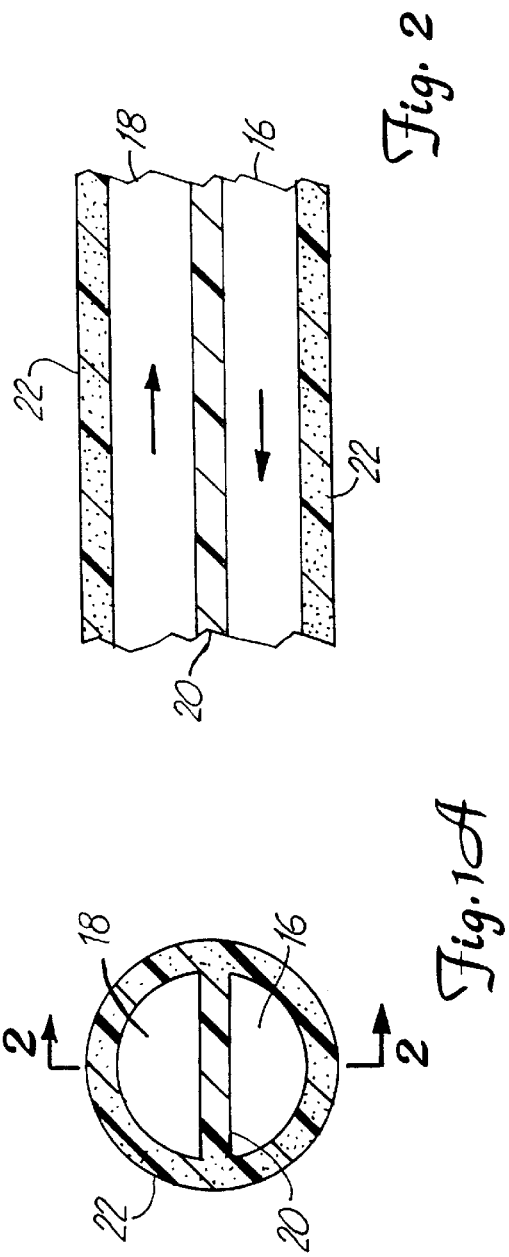
FIG. 2 shows longitudinal cross section taken along lines 2—2 of the apparatus of FIG. 1.

The invention will be further described with reference to the Drawing, wherein FIGS. 1 through 3 provide an apparatus for treating osteonecrosis that employs different portions of a single catheter to perform transdialysis, in which a patient's own endogenous factors and/or mediators (autologous agents) and other soluble factors are used to promote healing or growth in an affected area. Applicant has discovered, for instance, that early stage AVN can be managed by augmenting current initial treatments (e.g., core decompression) with an apparatus of this invention in order to both reduce interstitial edema and to continuously deliver growth factors. Biological agents can be either endogenous (transdialysis) or exogenous (egg., delivered by diffusion from within the perfusate).

The method and system of this invention can also be used for "transdialysis" between portions of the same tissue site. Coaxial transdialysis will effectively increase the surface area of the interface. It is known that at low flow rates, fluids on either side of a semipermeable membrane will come into equilibrium, while at high flow rates, there is less relative exchange. Coaxial transdialysis will allow two-way transport of autologous factors, which can be diagramed as follows:

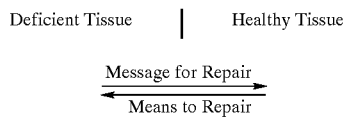

An apparatus of the present invention, for performing coaxial transdialysis, will typically involve the use of two or more hollow tubes in a coaxial arrangement. The outer tube is preferably formed of a semipermeable microcatheter (with the nature of the permeability being determined by the disease state), and is sealed on both ends. The inner tube is preferably open on both ends, and has a means of pumping fluid through the tubing. The inner tube has a larger diameter in the middle than on either end. This results in a lower cross-sectional area for fluid movement and consequently higher flow. High flow in semipermeable systems results in less exchange across the membrane. At either end of the transdialysis catheter is a large cross-sectional area, which allows low flow, and near equilibrium with the external environment.

By measuring viable cell distribution in the impaired portion of the bioreactor, it is expected that the apparatus will provide at least a significant increase in cell counts in the impaired area. Yet, to the best of Applicant's understanding, neither autologous transdialysis or the microdialysis bioreactor, as described herein, have been previously described or used as an ex vivo model. Autologous transdialysis is of particular value under conditions where it can be used to absorb sufficient factors and transport them to the impaired site in an in vivo model of avascular necrosis.

Figure 1A:
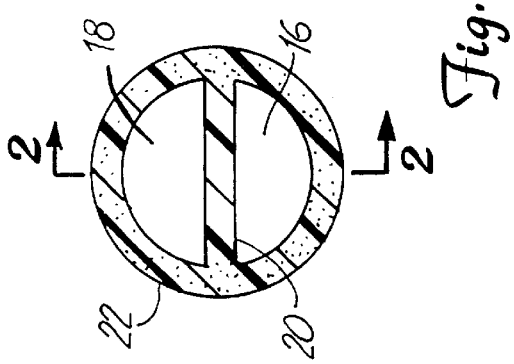

In particular, the apparatus is designed to employ microcirculation to perform "transdialysis", by the recovery and delivery of factors such as biological mediators and stimulating factors between different portions (e.g., healthy and injured) of the tissue. FIG. 1 shows an apparatus (10) having both a microcatheter component (12) and a delivery pump reservoir (14). The cross sectional and magnified views shown in FIGS. 1A and 2, respectively, show that delivery lumen (16) and recovery lumen (18) are separated by impermeable barrier (20) and surrounded by semipermeable membrane (22). Optionally, the delivery and recovery lumen (in the form of conduits or passageways) can be provided in any suitable form, e.g. in the form of discrete microporous catheters, separated by a barrier to separate and prevent direct contact between the two.

Such an embodiment can be used for a variety of applications, e.g., the repair of necrotic bone brought about by avascular necrosis. As shown in FIG. 1, for instance, the proximal region of bone is healthy bone, while the distal portion is diseased. The microcatheter is positioned within the bone with its distal surfaces in the injured region and its proximal surfaces in healthy bone. Once in place, the surfaces of microcatheter (12) serve a variety of roles, as determined by their location within the tissue (e.g., bone) and along the flow path of delivered fluid. In order, these roles include: a surface (22a) that serves to accumulate and remove biological stimulating factors (identified by o's) from the region of injured bone and transport them to surface 22(b), whereupon the factors are released into healthy bone, where they serve to stimulate the natural production of healing factors (identified by Δ's). The healing factors, in turn, are then accumulated and removed by portion (22c) and carried back into the region of injured bone, where they are themselves able to diffuse out from portion (22d) of the microcatheter surface.

In such an embodiment the delivery and removal functions can be accomplished by any suitable means. Preferably, the delivery function is accomplished by diffusion brought about in the course of hydrostatic flow, while the removal function is accomplished by either hydrostatic or hyperosmolar forces. Optionally, and particularly where both functions (delivery and recovery) are accomplished by hydrostatic forces, the pumps used to produce those forces are separately controllable such that the flow can be balanced or otherwise adjusted between the two, to the point where one or the other pump can be turned off altogether to permit single catheter delivery or removal alone.

FIG. 3 shows a preferred pump configuration for use with the microcatheter of FIG. 1. It can be seen that pump (14) includes both a substantially rigid external bulb (24) and an elastomeric internal bulb (26) containing the fluid (28) to be delivered to the tissue. The fluid can be of any suitable type, e.g., normal saline, Ringer's Lactate, or the like, optionally including medicaments or other therapeutic agents.

A hypertonic solution (30) is positioned in the cavity between external bulb (24) and internal bulb (26), which is retained in position, in part, by a semipermeable barrier (32) positioned between the hypertonic solution (30) and the recovery lumen (18). Optionally, and preferably, a fluid resistor (34) can be positioned between the fluid reservoir and the delivery lumen (16) in order to control flow. In use, fluid (28) is delivered to the microcatheter through lumen (16) by hydrostatic pressure, which initially is caused by osmotic pressure of fluid flowing from recovery lumen (18) and into the chamber containing hypertonic solution (30). More preferably, the apparatus is provided with an activation mechanism to control the onset of flow. In the course of use, the fluid that returns from the microcatheter via lumen (18) enters the space occupied by the hypertonic solution, causing it to swell. This swelling, in turn, further compresses elasomeric bulb (26), resulting in the delivery of additional fluid. The contents of either or both chambers can be provided with external access means (e.g., needle ports) in order replenish or remove their contents, and recharge the apparatus in situ.

An apparatus for the treatment and monitoring of compartment syndrome will be described with reference to the Drawing, wherein FIGS. 4 through 9 show a preferred apparatus (40) for such purposes. Apparatus (40) can itself be provided in a number of optional embodiments, depending for instance on the type of reservoir used, including an embodiment for use in monitoring the site and another embodiment for use in treating the site.

Figure 4:
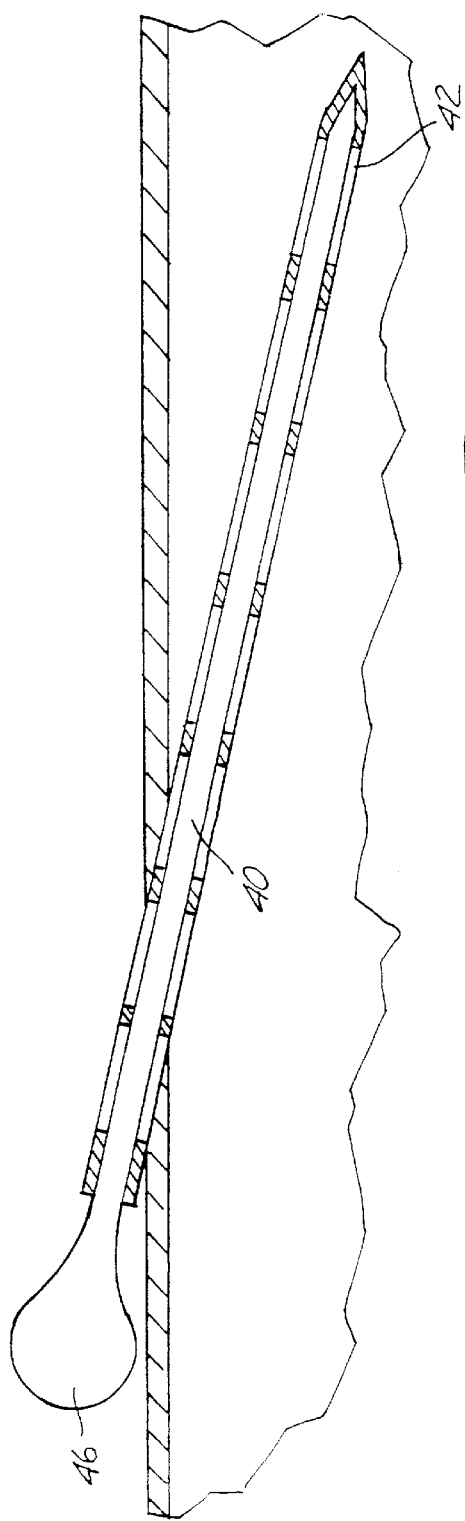
FIG. 4 shows a preferred apparatus for use in monitoring or treating compartment syndrome, including a sheath for its placement.
Figure 6:
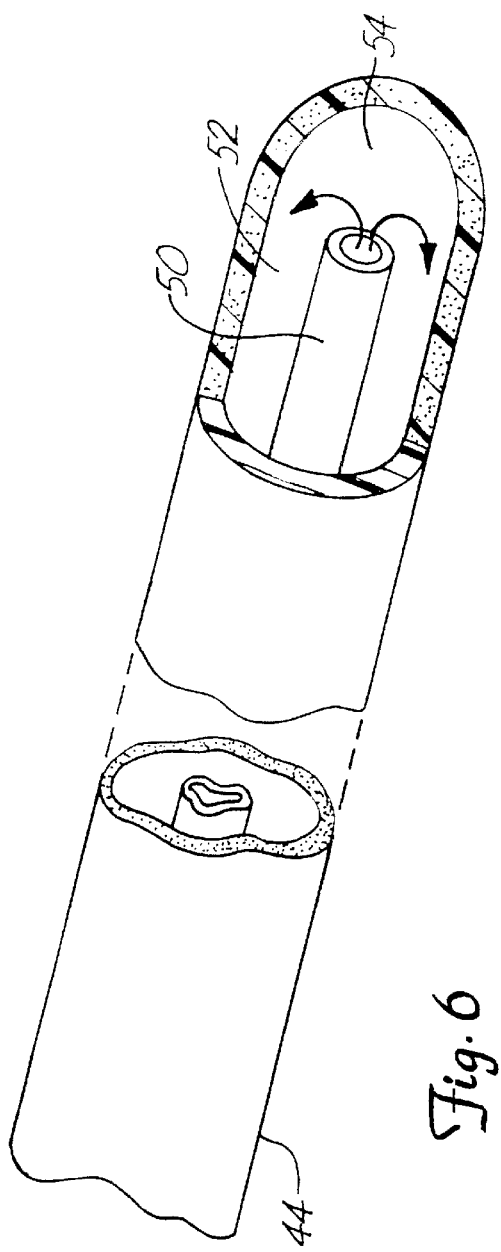
FIG. 6 shows an enlarged view, with portions cut away, of the coaxial microcatheter portion of the apparatus of FIG. 4.
Figure 5:
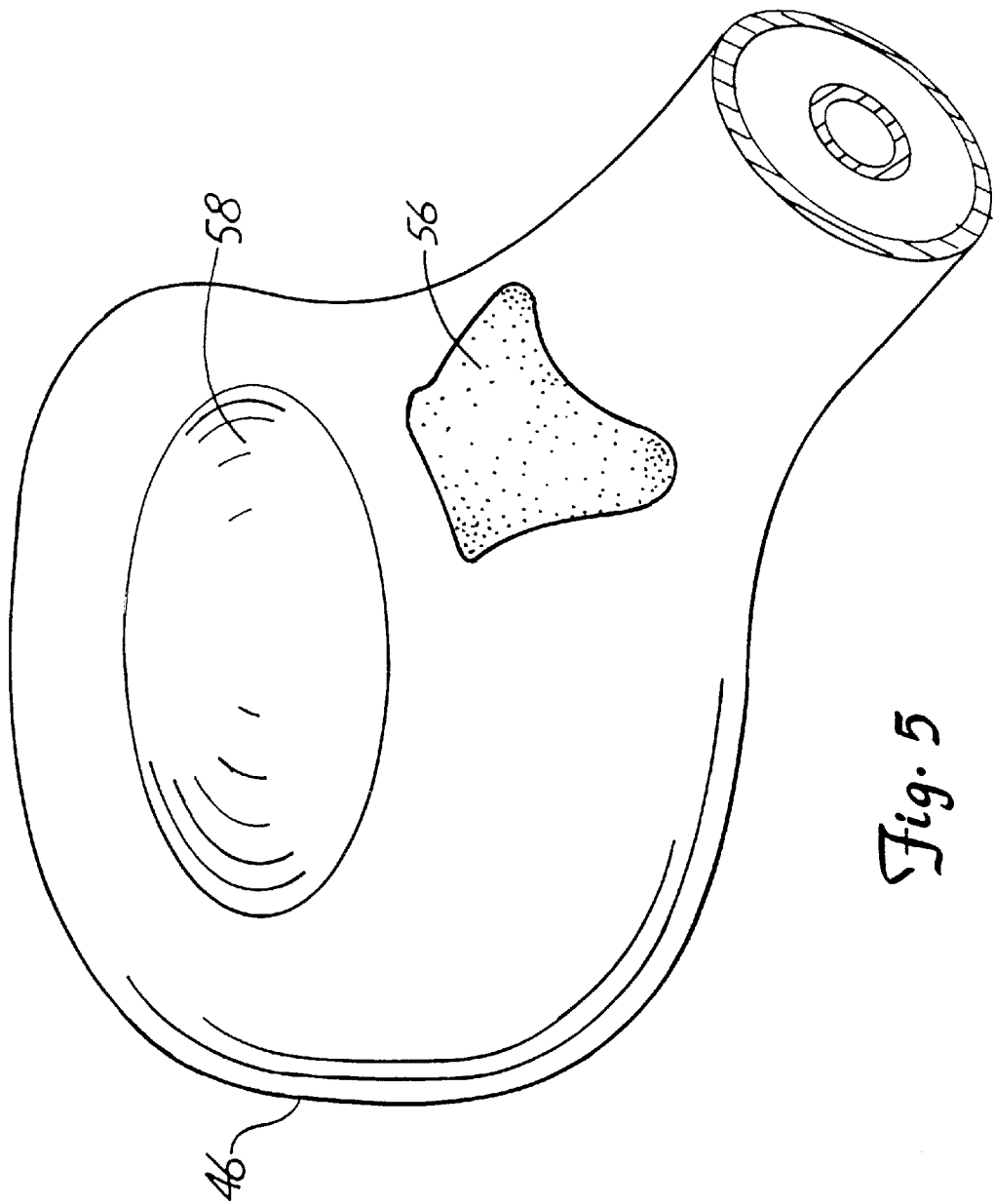
Figure 5A:
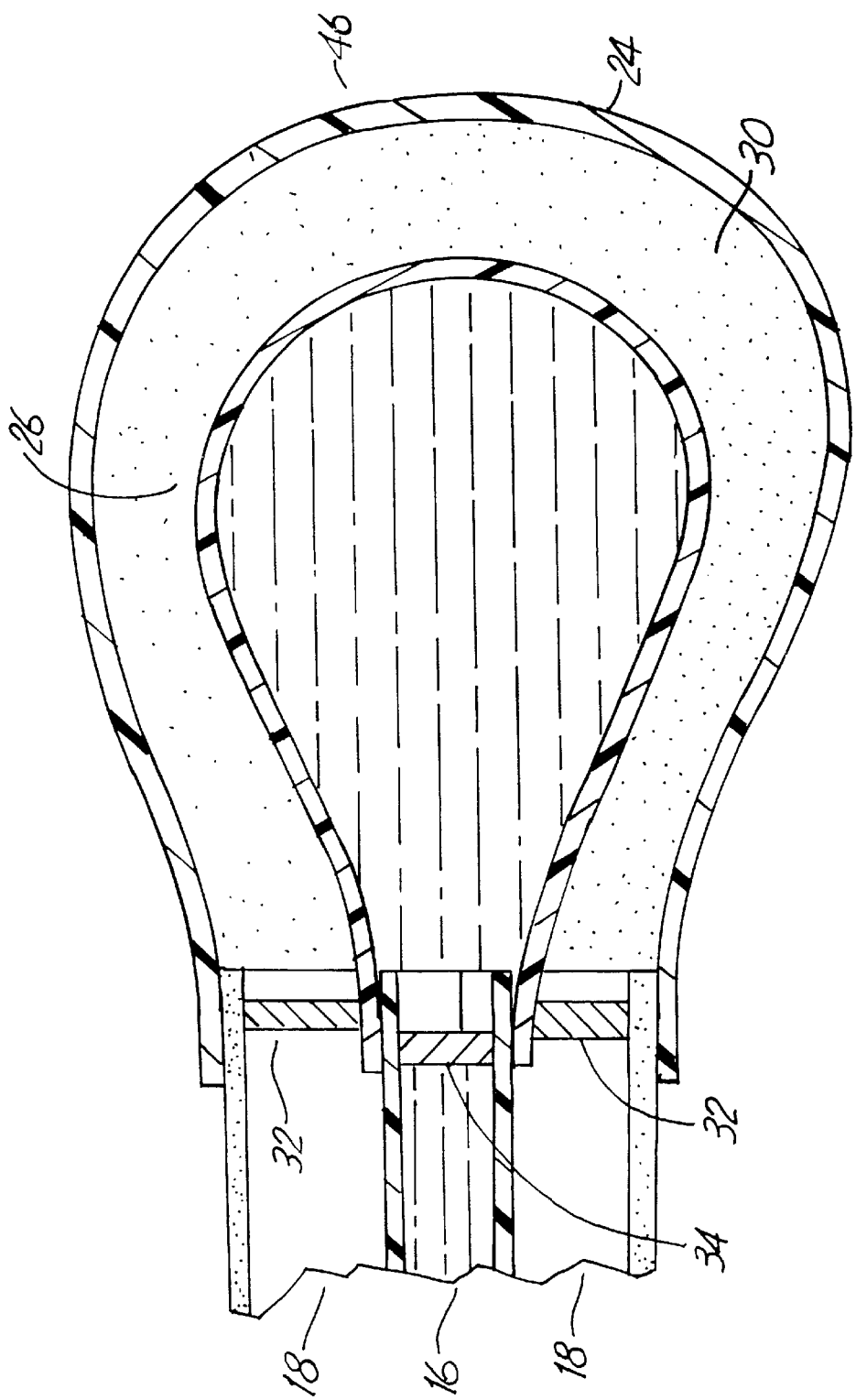
FIG. 5a shows a cross sectional view of the pump reservoir.
Figure 10:
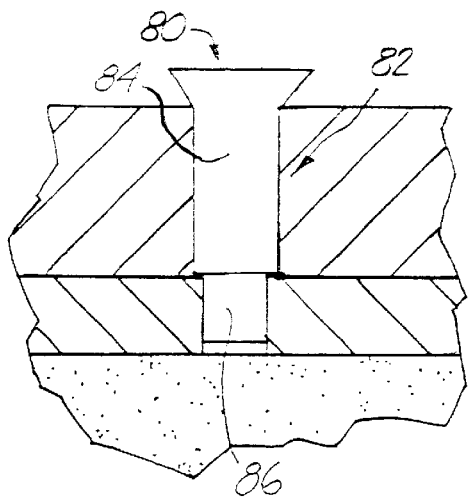
FIG. 10 shows a preferred apparatus for treating cerebral edema.

FIG. 4, in particular, shows an apparatus (40) positioned in place within delivery sheath (42), which in turn is positioned subcutaneously in a site suspected to exhibit compartment syndrome. FIG. 6 shows an exploded view of the microcatheter portion (44) of apparatus (40), while FIGS. 5 and 5A show perspective and cross sectional views, respectively,,of a preferred reservoir (46) for monitoring the site. FIG. 7 shows an isolated view of the delivery sheath (42) itself, and FIG. 9 shows a preferred reservoir (60) for treating the site by delivering a hyperosmolar solution to the site. FIG. 8 shows an optional apparatus (70) for use in reducing pressure within the site, that includes a plurality of sheaths as shown in FIG. 7, connected to a manifold and source of negative pressure.

In use, delivery sheath (42) is inserted into a desired position subcutaneously, whereupon the apparatus (40) assembly is inserted into the sheath. As seen in FIG. 7, the sheath is preferably of a size and configuration that will permit it to be inserted into the body, and having walls sufficiently permeable (e g., as shown having longitudinal grooves (43)) to permit the desired (e.g., uninhibited) flow of fluids within the tissue and between the tissue and microcatheter. With the sheath in position it can be used for a variety of sequential steps, including to first monitor the site in order to diagnose compartment syndrome, and thereafter to treat the site by the reduction of pressure, and optionally, the delivery of medicaments or other agents.

As seen in FIG. 6, a preferred microcatheter (44) for such use is provided in the form of coaxial lumen, including an inner lumen (50) surrounded by an outer lumen (52). Inner lumen (50) is sufficiently shorter than the outer lumen (52) in order to provide for fluid communication between the two lumen at the distal end chamber (54). Inner lumen (50) is preferably formed of an impermeable material, in order to assure that the delivered fluid (and any solutes therein) traverse the entire length of the lumen. Outer lumen (52), in contrast, is formed of a semipermeable material to provide a microcatheter of the type described herein.

Optionally, and preferably, a microcatheter of this (or other suitable) type can be used to both monitor and treat the site, by the use of reservoir portions adapted for such use. For instance, apparatus (40) can be used to first monitor the site by sampling the interstitial fluid, since ischemia is generally associated with either increased pressure or a lowering of pH within the affected tissue. As seen in FIG. 5, a preferred monitoring reservoir can include a number of optional features, such as a chemical or metabolic (e.g., pH) indicator portion (56) and a pressure indicator (58).

In the event compartment syndrome is indicated, a new microcatheter/reservoir assembly can be positioned in the sheath in order to deliver a hyperosmolar solution and reduce pressure in the site. As seen in FIG. 9, therapeutic reservoir (60) is fabricated having an elastomeric outer balloon (62) and an impermeable elastomeric inner balloon (64) containing a hyperosmolar solution (66), which in turn optionally contains therapeutic agents. Positioned between balloons (62) and (64) is a fluid reservoir (68). Upon flow of solution (66) from the inner balloon, through the coaxial microcatheter, and back to fluid reservoir (68), the inner balloon is able to contract by virtue of its natural elasticity (and further deliver fluid via hydrostatic means) as the outer balloon expands to accommodate the increasing volume of recovered fluid. Optionally, and as shown in FIG. 9, the outer balloon also includes one or more needle ports (70) that permit the user to sample or remove the contents of the outer balloon (68).

Returning briefly to FIG. 8, there is shown an apparatus for use in connection with a source of negative pressure. The apparatus (70) includes a manifold and fluid collecting reservoir (72) that is operably connected via conduit (74) to a source of negative pressure (not shown) and to a plurality of microcatheter or other recovery conduits. Preferably, the microcatheters are provided in the form of porous or open sheaths, such as the sheath shown in FIG. 7 with respect to the placement of microcatheter assemblies.

Turning next to FIGS. 10 through 13 there is shown alternative preferred embodiments of an apparatus (80) for use in treating cerebral edema by placing one or more catheter probes directly into brain parenchyma. The probes can be used for any suitable purpose, e.g., the recovery bulk fluid from the parenchyma. Apparatus (80) includes a generally hollow and cylindrical rigid portion (82), which in turn is comprised of stepped down portions (84) and (86), for traversing the soft tissue and skull, respectively. Positioned within portion (82) is a telescoping portion (88), which in turn is dimensioned to retain a plurality of microcatheters (90). In use, rigid portion (82) is positioned through the surrounding tissue and within the skull, whereupon telescoping portion (88) is positioned into the brain to the desired point.

Figure 12:
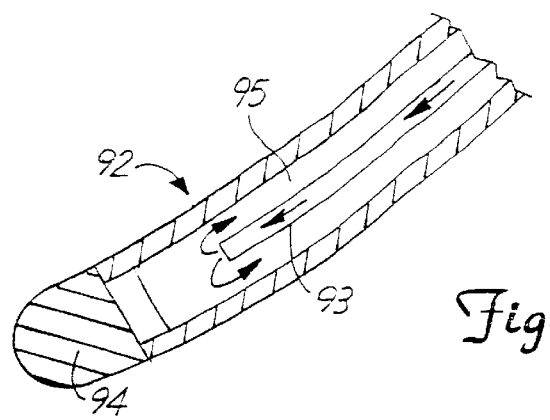
FIGS. 12 and 13 show alternative preferred embodiments of the microcatheter portion of the apparatus of FIG. 10.
Figure 13:
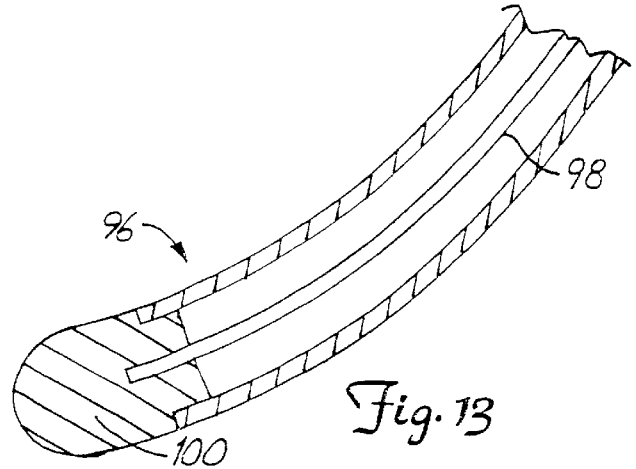

Once in place, microcatheter portions (90) are themselves positioned (e.g., splayed) from the distal end of telescoping portion (88) to their final position within the brain. The microcatheters, in turn, can be of any suitable type as described herein. FIG. 12, for instance, shows a preferred embodiment in which a coaxial recover microcatheter (92)

is provided, having inner lumen (93) and outer microporous lumen (95), together with a solid polymeric tip (94), which is optionally fluted or otherwise shaped to facilitate placement. Such a microcathter can be used to deliver (e.g., perfuse or circulate) hyperosmolar solutions in the manner described above. FIG. 13 shows an alternative embodiment (96) in which one or more recovery microcatheters are used, having central guidewires (98) and solid polymeric tips (100) to facilitate placement and use.

Figure 14:
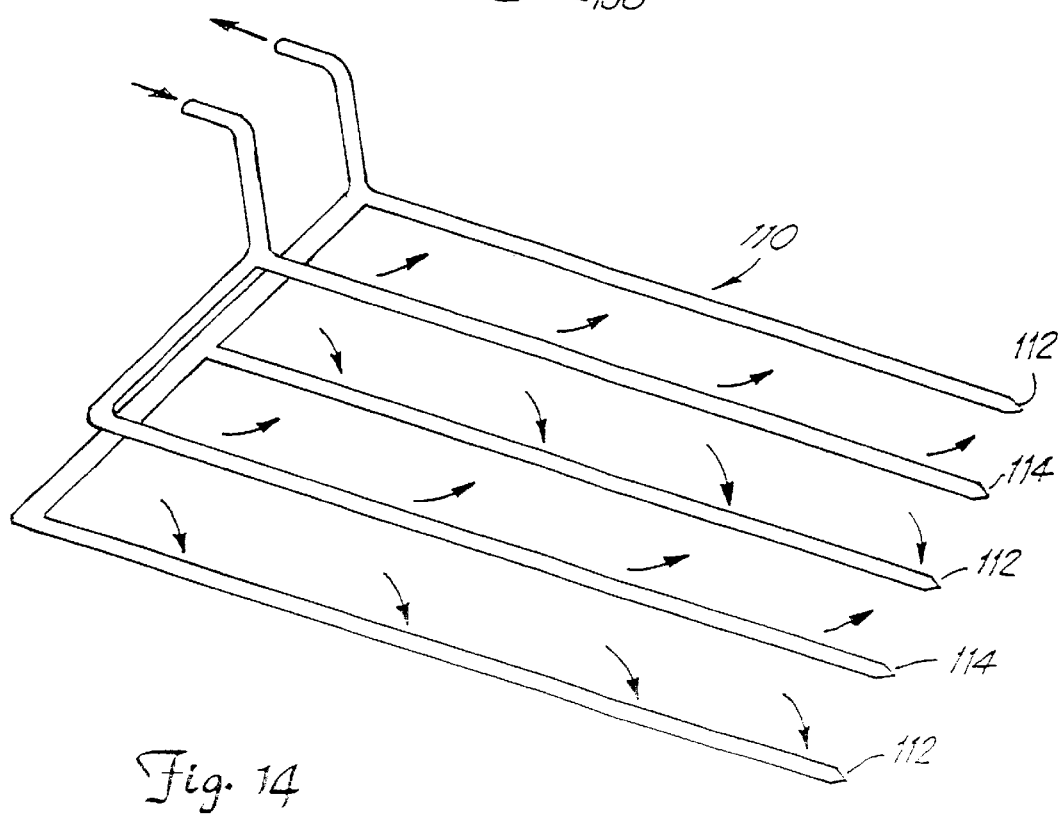
FIG. 14 shows a preferred two dimensional, dual catheter (delivery and recovery) apparatus for use in skin flap survival or subcutaneous augmentation.

FIGS. 14 through 17 show a variety of preferred embodiments of dual- and higher-catheter arrangements for both in vivo use, e.g., in the treatment of skin flaps and solid tumors, and for in vitro use, e.g., for tissue culture and regeneration. FIG. 14, for instance, shows a preferred embodiment of a dual catheter assembly (110) having a plurality of recovery catheters (112), connected to a recovery pump reservoir (not shown) laying in parallel to a plurality of delivery fibers (114), similarly connected to a delivery pump reservoir. The catheters themselves can take any suitable form, e.g., in the form of hollow (and optionally open ended) microporous catheters (of the type shown in FIG. 13, optionally having a central guide wire). Preferably, one or more of the delivery catheters is provided in the form of a coaxial catheter, of the type shown in FIG. 12, in order to facilitate the establishment of convective flow between delivery and recovery fibers by providing the flow of fluid in each in a single desired direction.

Figure 11:
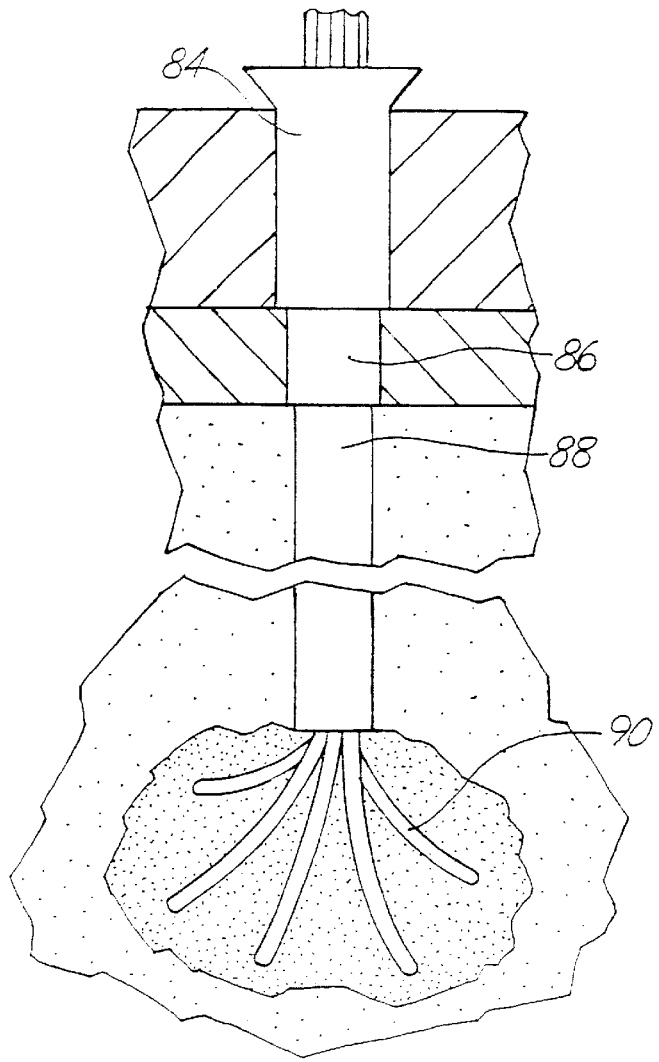
FIG. 11 shows the apparatus of FIG. 10 in position within the skull and brain.
Figure 15:
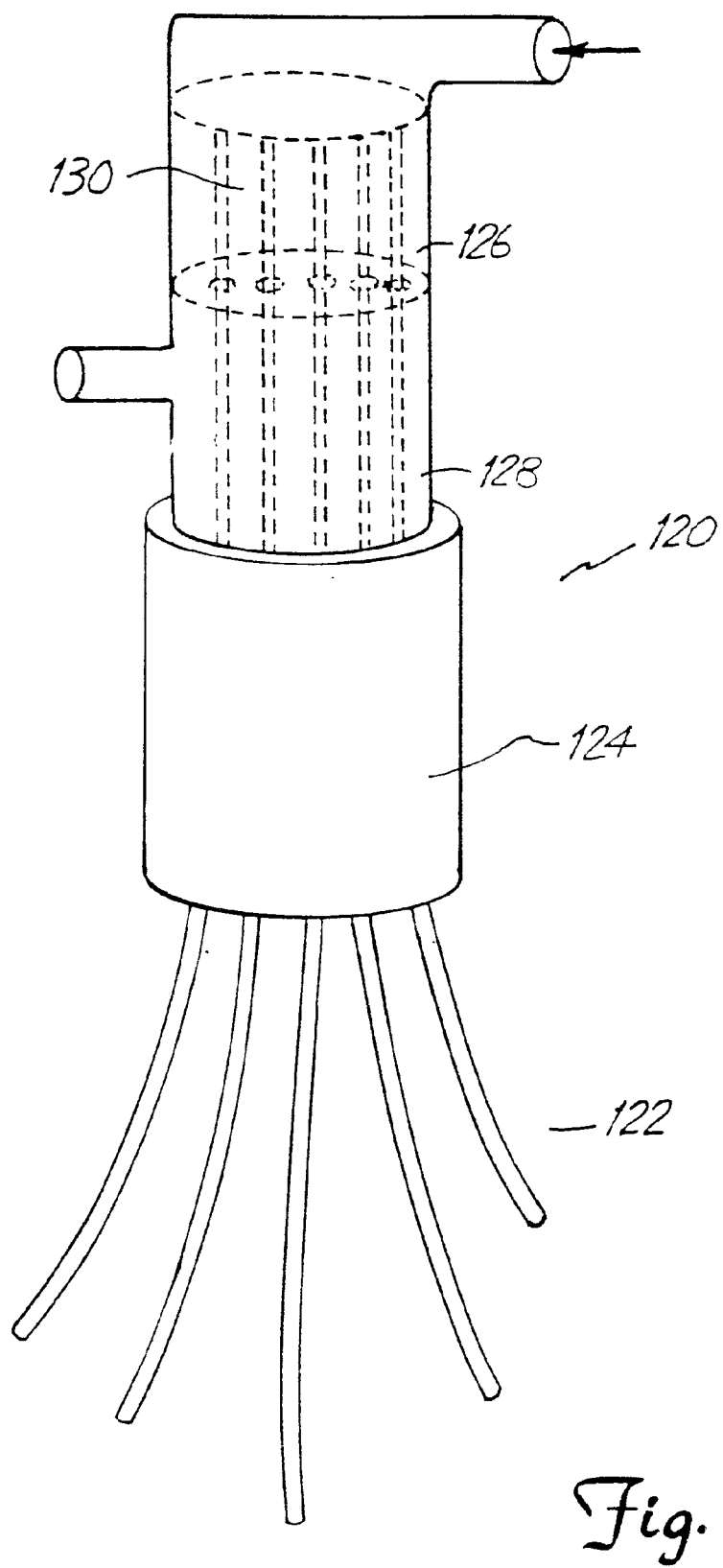
FIG. 15 shows a preferred fluid chamber configuration for embodiments such as that in FIG. 11, having a plurality of coaxial microcatheters.

FIG. 15, in turn, shows a representative apparatus (120) showing the relationship of delivered and recovered fluid chambers, e.g., for use in combination with a coaxial microcatheter assembly as shown in FIG. 11. Such an apparatus can be used for other applications as well, such as placement into tissue by use of A plurality of porous microcatheters (122), preferably of the coaxial type described herein, are positioned to splay out from the body (124). Body (124), in turn, supports fluid chambers (126) and (128) for containing, respectively, fluid for delivery and recovered fluid. The fluid delivery chamber (126) is itself shown as attachable to a pump reservoir (not shown) containing the fluid to be delivered. Fluid recovery chamber (128), in turn, is shown attachable to a reservoir (not shown) for containing or removing the recovered fluid. The interior passageways (130) of each catheter can be attached to a manifold positioned within fluid delivery chamber (126), while the exterior passagewayss are positioned within the fluid recovery chamber (128).

In use, the splayed coaxial microcatheters can be positioned with a suitable tissue or material and there used to both deliver fluid via the interior passageway, and recover fluid from the surrounding medium by means of the outer passageway, and semipermeable nature of the outer wall. Optionally, and preferably, microcatheters used in this invention can have regions of varying characteristics, including varying porosity, rigidity, and the like, for instance those, that vary between sequential and adjacent, or suitably spaced, longitudinal sections, or in or any other suitable pattern. Such variations can be used, for instance, in a size exclusion fashion to improve or provide the ability to retain or permit the passage of solutes of varying sizes in a predetermined manner. Such variations can also be used to provide regions of greater rigidity or varying structure (e.g., fluted), in order facilitate their placement in tissue. Such variations can also include the incorporation of means (e.g., radioopaque materials) to facilitate the visualization of implanted catheters.

Figure 16:
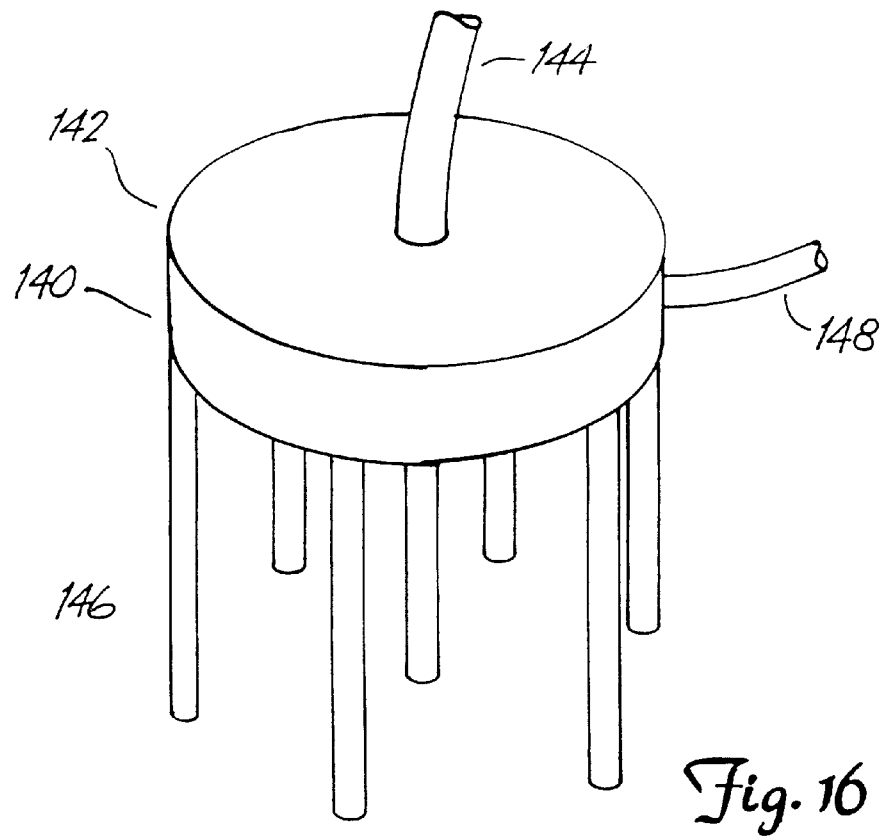
FIGS. 16 and 16A show side and top views of a preferred three dimensional dual catheter apparatus for use in treating intact tissues.
Figure 16A:
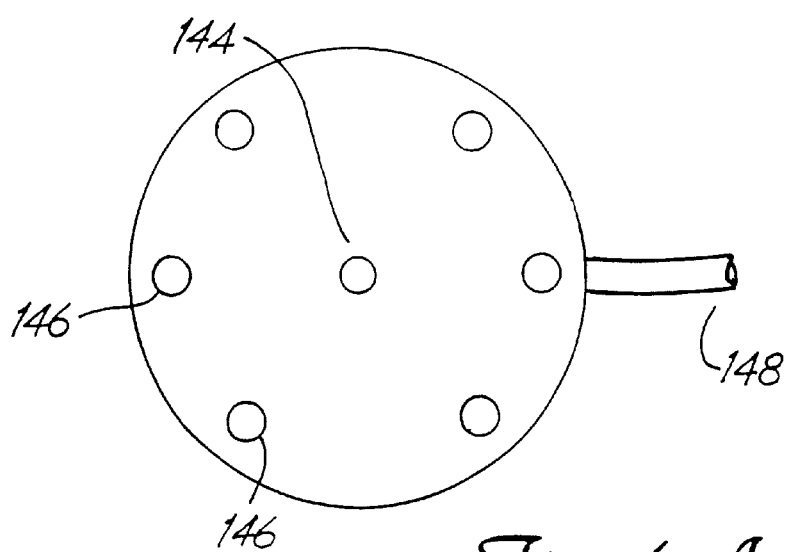

FIGS. 16 and 16A show a representative embodiment of an apparatus (140) of this invention for use in treating tissue. Disc portion (142) is used to retain one or more delivery conduits (144) as well as one or more (and preferably a plurality of) recovery conduits (146) in the form of microcatheters. The recovery microcatheters, in turn, can be connected to manifold arrangement (not shown, but preferably positioned within disc (142)), and can be finally removed via recovery conduit (148). FIG. 16A shows a top view of the apparatus of FIG. 16, showing a preferred arrangement in which a plurality recovery conduits (e.g., six, in order to provide a desired hexagonal configuration) are positioned in and equidistant fashion from a single delivery conduit.

In use, the apparatus of FIG. 16 is preferably positioned with its recovery microcatheters positioned within a desired site. such as tissue, and the disc portion and/or delivery conduit positioned either within or outside the body. Such an embodiment is particularly well suited to treating three dimensional areas such as tumors, in order to both deliver fluid containing therapeutic agents and recover fluid from the site as well.

Figure 17:
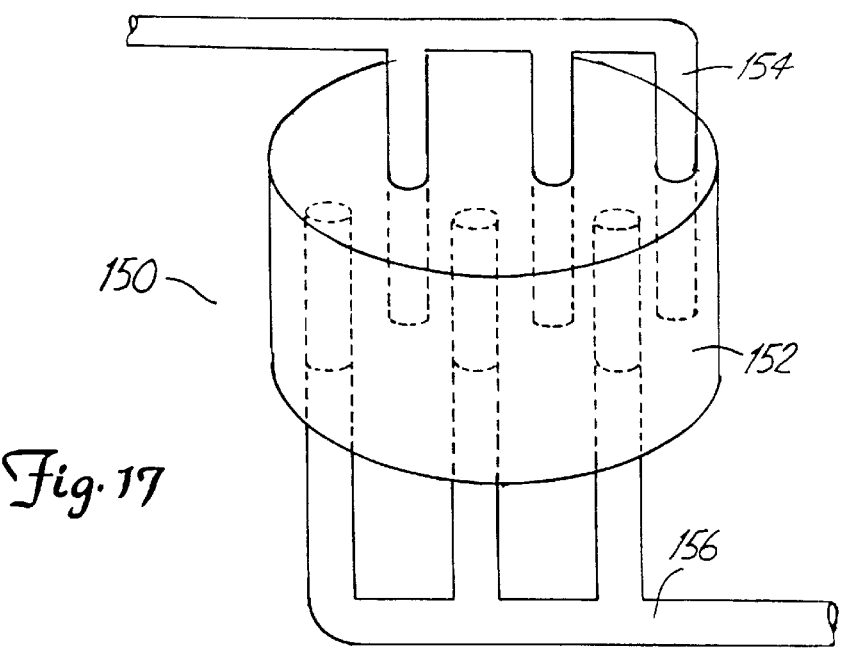
FIG. 17 shows a preferred three dimensional dual catheter apparatus for use in tissue culture and tissue engineering.

Finally, FIG. 17 shows a representative dual catheter embodiment for the use in tissue culture and tissue engineering. The apparatus (150) includes a block of material (152) suitable for providing a framework (e.g., cell scaffold) for the growth of cells or tissue. Examples of such materials include, for instance, hydroxyapatite, polymeric matrices, and biologically acceptable ceramics. Positioned within the block are one or more delivery microcatheters (154) and one or more recovery microcatheters (156). In use, the block can be seeded with cells and incubated under conditions suitable to facilitate the growth of such cells or tissue. In the course of incubation, the delivery and recovery systems can be employed to provide the cells with required nutrients and remove waste and other products. The cells can be incubated in vitro, or the apparatus can be implanted into the tissue with the catheters attached, and incubation can proceed in vivo. Once the cells or tissue have grown to a desired degree (e.g., confluence), a block that has been incubated in vitro can be implanted in the body as a tissue substitute. Optionally, and preferably the block is shaped (either prior to or after cell growth) for its intended purpose.

The method of the present invention can be accomplished using a variety of catheters, as described in considerable detail below. In a preferred embodiment, the catheter includes one or more semipermeable microcatheters for use in performing tissue microdialysis. Semipermeable microcatheters (also known, and occasionally referred to herein as microdialysis catheters, microdialysis fibers, hollow fibers, microfibrils, microtubules, or microfibers) are implanted into tissue or fluid spaces for the purposes of selective exchange between the tissue and the semipermeable membrane forming the walls of the microcatheters. Therapeutic tissue microdialysis, as described by Applicant, can be used to provide site-specific therapy, in which direct interstitial therapy is achieved by replicating the diffusional and convective forces of the microcirculatory system.

Whereas previously microdialysis has been performed within the brain for diagnostic purposes, therapeutic microdialysis, by comparison, will generally be employed for treatment of the interstitial space, including indirect treatment by means of access to the ventricle. The affected microcirculation typically includes the body's system of arterioles, capillaries, venules, and lymphatics, and represents the final step in the process of cellular nutrition and maintenance of cell viability and the final roadblock to treatment of disease on the cellular level. Therapeutic microdialysis is of particular value when applied to one or more of four broad classes of clinical conditions, namely microcirculatory disruption, systemic toxicity, the removal of large, poorly diffusible molecules, and the removal of excess tissue fluid, solute, or toxin Therapeutic microdialysis, as described herein, provides a number of advantages, including the ability to treat tissue sites without relying on the blood circulation system. Particularly, probes can be adapted to be positioned directly into the tissue or fluid space. The semipermeable microcatheters can be provided in very small sizes, and having semipermeable walls. As such, the apparatus provides a unique combination of features, including the ability to employ a magnitude of force gradients, multiple-fiber arrays, and controllable transportation ability (transdialysis). The use of small semipermeable microcatheters provides increased surface area for exchange, the ability to target microscopic tissue areas.

Therapeutic microdialysis by the use of semipermeable microcatheters provides a unique combination of features and opportunities. These include (1) the ability to control the magnitude of force gradients (e.g., hydrostatic and diffusional forces magnitudes), (2) the ability to control the direction of flow (e.g., into or out of the semipermeable microcatheter), (3) the optional use of multiple fiber arrays (for removal, delivery, and/or monitoring), and (4) the ability to transport autologous factors (e.g., as in transdialysis).

As used herein with respect to edema, the following words and terms will have the meanings ascribed below:

the term "tissue site" will refer to a site within the body comprising first and second fluids separated by an osmotic barrier (i.e., barrier that substantially permits the unrestricted flow/interchange of the water (solvent) and permeant solutes between the fluids while preventing the unrestricted flow of impermeant solutes, thereby permitting the fluids to maintain different osmolarities), with either or both fluids optionally containing cells that provide further osmotic considerations with respect to their surrounding fluids;

"cerebrum" will refer to a tissue site wherein the first fluid includes the interstitial and intracellular fluids of the brain, the second fluid is CSF, and the osmotic barrier is the ependyma;

the word "edema" will be used to mean excessive volume and/or pressure brought about at the tissue site by the accumulation of the first fluid, while the term "cerebral edema" will refer to swelling within the brain compartment brought about by an accumulation of interstitial and/or intracellular fluids;

"fluid" will refer to a bodily substance maintained in contact with an osmotic barrier, and including two components: 1) a permeant component that includes both water, together with electrolytes or other solutes that can collectively be described as "permeant solutes", since they are able to freely pass the particular osmotic barrier) and 2) an "impermeant solute" component (typically larger molecular weight solutes that are unable to pass through the particular osmotic barrier under the conditions employed);

"hyperosmolality" will refer to an increased concentration of a solution (in terms of the absolute number of impermeant solutes per unit weight fluid), whereas "hyperosmolarity" will refer to an increased osmotic concentration of a solution (in terms of the number of impermeant solutes per unit volume of fluid) as compared to either the normal fluid or other fluid in a tissue site; and finally, "hyperosmotic" will refer to a fluid having an osmolarity greater than another fluid.

See, for instance, Chapter 5 "Transport Through Membranes" in R. K. Hobbie, Intermediate Physics for Chemistry and Biology, John Wiley & Sons (1978), the disclosure of which is incorporated herein by reference.

In a particularly preferred embodiment, Applicant has developed a method and system for the treatment of cerebral edema by the use of site-specific treatment, including the use of site-specific microdialysis to sample directly from the CSF within the intraventricular spaces. The method can be used to prevent the development of life-threatening cerebral edema, and/or to ameliorate cerebral edema that is already present.

Applicant has further found that interstitial microdialyisis can be performed, having therapeutic value, in the course of clinical diagnostic monitoring of TBI patients and using components of conventional devices, such as those presently used for monitoring rapid, ongoing chemical changes in the interstitial fluid (ISF). In one such embodiment, one or more semipermeable microcatheters are adapted to permit their passage into the lumen of a conventional ventriculostomy catheter, of the type commonly placed in patients with severe TBI to enable CSF drainage and to monitor ICP. Such microdialysis fiber systems can be adapted for therapeutic (and optionally. also diagnostic) use in treating cerebral edema.

The fibers can be used to recover chemicals smaller than the molecular cut-off of the particular dialysis fibers, e.g., by the use of negative hydrostatic pressure (NHP), or suction, as the driving force behind dialysate collection. In one such embodiment, the fibers are adapted to pass into a standard ventriculostomy catheter in a manner that permits concomitant use of the ventriculostomy catheter for its conventional purpose (e.g., by means of a Y tube adapter). Therapeutic microdialysis can be used in combination with the regulated and monitored removal of CSF from the ventricular compartment in order to achieve one or more of the following functions 1) clinical diagnostic monitoring, 2) therapeutic intervention, and optionally, 3) the removal of interstitial fluid in order to reduce ICP and/or cerebral edema. The effectiveness of the method and system of the present invention can be determined by any suitable means, e.g., by reduced edema (as determined, for instance, by the use of magnetic resonance imaging (MRI) scanning techniques) and/or by lowering of ICP.

Since a key concern will typically be the permanent reduction of edema, as opposed, for instance, to a temporary reduction in ICP, preferred techniques will typically provide an assessment of tissue water content. While ICP reduction will typically be important as well, it is preferable to monitor tissue water content, since a clinically beneficial effect can be achieved in this regard without a detectable ICP drop. In turn, an ICP drop is not itself conclusive proof of a clinically therapeutic effect on edema. With injury, the cells within the brain tissue tend to swell by the accumulation of fluid. The present method and system are designed to lessen or even decrease such swelling, by causing water to flow from the cells to the interstitial fluid, and eventually from the first fluid site entirely.

A semipermeable microcatheter assembly can be provided, for instance, in the form of one or more individual microdialysis fibers, e.g., each on the order of about 10 cm to about 30 cm (and preferably between about 15 cm and about 25 cm) in length, with multiple fibers optionally being bundled together, for instance, with a thin flexible wire. Bundling fibers in this manner enables the bundle to be inserted through the lumen of the ventricular catheter, e.g., by means of a Y-connector inserted between the ventriculostomy and CSF drainage tubing. The number of fibers in any particular catheter design can be varied, dependent for instance upon the molecular cut-off desired. Preferably, however, the semipermeable microcatheter assembly is designed to be placed within the internal lumen of a conventional ventriculostomy catheter in a manner that permits the catheter to be used for its intended purpose, i.e., in a manner that does not occlude the flow of solvent or impermeant solutes to a point that precludes its use. In use, microdialysis catheters can be positioned intraluminally within the VC catheter, with the proximal tubing portions of the combined catheters being controllably and separately attached to suction to enable fluid extraction and collection. The rate of fluid-removal can be easily altered by making adjustments to the negative pressure applied to the combined system.

A system that includes ventriculostomy catheters and intraluminal microcatheters can be used to:

1) Perform clinical diagnostic monitoring, by the continuous or sequential sampling of the CSF, without the need to repeatedly pull CSF from the ports of the ventriculostomy drainage tubing or to obtain samples from the CSF drainage collection vial. This function is particularly useful where molecular/chemical entities of interest may be degraded due to exposure to light and/or heat.

2) Provide regulated and monitored removal of CSF from the ventricular compartment while enabling continuous monitoring of ICP by the ventriculostomy catheter, thus supplanting or replacing passive convective CSF drainage in the management of elevated ICP (wherein CSF drainage and monitoring of ICP cannot occur concomitantly). This function of the system enables improved clinical diagnostic monitoring as well as provide a therapeutic intervention. In the event that catheters cannot remove adequate volume of CSF to completely supplant convective drainage, the objectives outlined in use #1 above can still be achieved.

3) Provide a therapeutic effect by removing interstitial fluid and thus reducing ICP and/or cerebral edema. This effect, particularly when accomplished using a minimally invasive microdialysis system, would be highly desirable since such therapy may reduce secondary injury (e.g. pressure necrosis, incidence/severity of ischemia), patient morbidity and mortality. Effective reduction of cerebral edema may shorten the length of hospital stay in TBI patients and ultimately translate into reduced time and costs for rehabilitation therapy.

The present method and system for the treatment of edema addresses the osmotic fluid shifts caused by ischemia, and serves to manipulate those osmotic shifts in a therapeutic manner. The existence of osmotic fluid shifts, as the disease progresses, is likely in view of the consistent reports that the cells in many types of tissues begin to swell within minutes of ischemia. Applicant believes that this "cytotoxic edema", which is the earliest and perhaps most important type of edema, can be explained by osmotic fluid shifts. Cellular swelling is most likely related to the loss of ATP necessary to drive the Na—K ATPase pump. Because intracellular osmolarity is approximately 400 mosmols/L, and extracellular osmolarity is approximately 300 mosmols/L, there is an osmotic gradient induced that will cause fluid to pass into the cell after the loss of ATP. Because only cell-membrane-permeable agents will pass into the cell, large osmoles are left behind in the extracellular space. This will increase the osmolarity of the extracellular space, which in turn will pull cerebrospinal fluid from the ventricles (as well as the vascular space depending upon degree of ischemia) into the extracellular space.

Although, as described herein, there are several alternative approaches (and combinations thereof) for treating edema in a tissue site characterized by a increased volume of the first fluid, the present approach is particularly preferred since it both establishes an osmotic shift, and, at the same time, can include the removal of a fluid (e.g., the "second" fluid) from the site. In a tissue such as the brain, it can be shown that the removal of a seemingly small amount of fluid can have a profound and beneficial therapeutic effect on the pressure of the remaining fluid.

Semipermeable microcatheters and other components useful in the present method and system of this invention have been individually described previously, e.g., with respect to the bulk flow of fluids and its components. Applicant recognizes that the movement of fluid components within a particular fluid can involve other aspects as well, including for instance, the flow of solvent into and out of cells within that fluid. In the case of the brain, for instance, it is believed that the flow of solvent between the first and second fluids is actually an after effect of the flow of solvent from within cells (which had been swollen due to their initially hyperosmolar nature) contained in the first fluid to the interstitial fluid itself. While this relationship is, on the one hand, secondary to the consideration of flow between the barrier between first and second fluids making up a tissue site, it is critical to the health and well being of the patient. A preferred method of the present invention is optimized in order to not only reduce overall swelling, but also, to simultaneously maximize cell survival.

Intraventricular microdialysis, as described herein, will often involve transcranial placement of a ventriculostomy catheter, which is standard care in TBI patients. TBI patients have a high incidence of severe cerebral edema, so the relatively minor risks of ventricular catheter placement is acceptable. In patients who have suffered stroke, however, intracranial instrumentation is not the standard of care. There is a lower incidence of severe cerebral edema in stroke patients, so placement of ventricular catheters in these patients is less likely to be useful given contemporary treatment approaches. While the therapeutic benefits of ventricular microdialysis may tip the scale to favor placement of ventricular catheters in all stroke patients, a less invasive approach to be used early in stroke patients may have equal therapeutic and monitoring benefits.

The present method and system can be used for spinal applications as well. It is known that placement of a needle into the spinal canal in the lumbar level is a safe, relatively non-invasive procedure that is done in clinics and hospitals. The lower lumbar vertebral levels are safe because the spinal cord ends at the first lumbar vertebrae, with only nerve fibers (called the cauda equina) filling the spinal canal below that level. CSF circulates from the ventricles out into the spinal canal and back to the subarachnoid space. As in other tissues and systems, the diffusion of large osmoles in a fluid filled space is slower than diffusion of water.

Spinal microdialysis can be performed in an analogous manner to that described herein with regard to ventricular microdialysis, but with a less invasive procedure employing skills known to most medical practitioners. A catheter that includes a semipermeable microcatheter can be placed in the subarachnoid space in the lumbar spinal cord, and be advanced upward within the spinal canal. Like ventricular microdialysis, a negative hydrostatic pressure can then be drawn on the lumen of the microdialysis fiber. This will pull fluid and salts from the CSF space, leaving larger molecules behind. Because water diffuses faster than large molecules, removal of water from the spinal canal will result in a diffusion gradient of water towards the microdialysis fiber. Larger molecules will tend to stay in the ventricles and central spaces because large molecules diffuse slower, and also because there is no diffusion gradient towards the microdialysis fiber. This, in turn, produces osmotic gradients to pull tissue edema from the cerebral tissue, even with placement of the fiber in the spinal canal. Due to the natural flow of CSF, spinal microdialysis may produce more cortical edema reduction than periventricular edema reduction. The CSF flowing downstream from the spinal canal into the subarachnoid space adjacent to the cortical tissue will have slightly higher osmotic pull than the ventricles, which are upstream from the spinal canal. As such, ventricular and spinal microdialysis may be, done simultaneously to maximize both periventricular and cortical edema reduction.

This approach can also be applied to the treatment of spinal cord injury, because the osmotic gradients exit throughout the CSF. Edematous spinal cord tissue will also lose interstitial fluid due to the osmotic gradients, resulting in less spinal cord edema.

Care should be taken in performing spinal microdialysis to avoid the risk of herniation within the cerebral tissue. In the face of increased intracranial pressure, it is known that herniation can occur during conventional spinal tap because fluid is withdrawn rapidly after the needle is inserted, thereby loweing the pressure of CSF in the spinal canal. With spinal microdialysis, there will be no open needle drainage of CSF and only slow removal of CSF. Tissue fluid moves into the CSF space due to osmotic gradients at approximately the same rate that fluid would be removed from the CSF, resulting in little net volume change.

An apparatus of the present invention can be used to recover and/or deliver fluid or its components by any suitable means, including by recovery only (e.g., an initial net decrease in volume of the fluid contacting the conduit), or by delivery only (e.g., an initial net increase in volume to the fluid). In certain embodiments, an apparatus can employ combined recovery and delivery, which can be achieved in a sequential or simultaneous fashion, with either no change or an initial net change (increase or decrease) in volume. Delivery and/or recovery can be achieved without a net change in the volume of fluid contacting the conduit, e.g., by the use of conduits in which the void space has been primed (filled with suitable fluid), such that flow into or from the conduit can be achieved immediately and without a net change in volume. Recovery and/or delivery, in turn, can involve either the bulk fluid bathing the delivery/recovery conduit, or one or more fluid components (e.g., solvent only or impermeant solutes only, as by microdialysis).

Optionally, the system can be used to affect the osmolarity of one or more fluids without either the actual delivery or recovery of fluid, that is, without involving an initial change in the volume of either fluid. Such an approach is useful in view of the fact that it is typically the absolute and relative numbers of osmoles, given that their particular size, charge or molecular makeup is similar, that determines the relative osmolarity of two solutions. For instance, a catheter of this invention can be used to deliver one or more agents that affect the osmoles already present, such as, diffusible agents that are adapted to alter the effective impermeant solute concentration by decreasing the effective number of impermeant solutes (e.g., aggregating existing osmoles by forming a colloid, precipitate, complex or flocculent), or by increasing the effective number of impermeant solutes (e.g., by chemical, mechanical, elecrochemical (e.g., laser) or thermal means, for instance, to disperse or cleave existing osmoles in a manner that increases their overall number).

An apparatus of the invention, in a preferred embodiment, includes the use of one or more catheters adapted to be positioned in fluid communication with the second fluid in a tissue site exhibiting edema brought about by accumulation of a corresponding first fluid. The catheters can be provided in any suitable form, e.g., in the form of a single lumen or fiber, or as a plurality of lumen or fibers, or any combination thereof.

A preferred apparatus includes the use of a plurality of semipermeable microcatheters, e.g., dual hollow fibers (generally one each, in/out flow), a bundle of multiple hollow fibers, as coaxial fibers, or in a loop configuration. Optionally, the apparatus can include other components, including components used within or amongst conduits/fibers (i.e., positioned in tissue site). Such components include those adapted for use in delivering or positioning the conduit to a tissue site. Examples of such components include conventional ventriculostomy catheters, introducers, guide wires (e.g., either separate from or within a bundle of semipermeable microcatheters), and additional intregral and/or separately provided lumen or tubes, with associated connectors and controls.

The apparatus can also include one or more components adapted for use in a manner that is ancillary to the conduits/fibers themselves, e.g., adapters to permit concomitant use of both apparatus and other devices (e.g., catheters). The apparatus is preferably provided in the form of a kit that includes such optional components, together with directions for use.

The invention will be further described with reference to the Drawing, wherein the following general terminology will be used, and the various embodiments will be described with reference to a preferred embodiment in which an apparatus is delivered to a ventricle of the brain in the course of TBI.

"One-way" will mean that fluid is moved only one way, which could be out of the ventricle, or into the ventricle.

"Two-way" will mean that fluid is moved both into and out of the ventricle at the same time or sequentially. Typically, the fluid removed from the ventricle is discarded (not returned).

"Recirculating" will refer to fluid that is circulated within the system, going both in and out of the ventricles. In contrast to two-way, fluid is returned to the ventricle, and recirculating embodiments will typically include mechanisms for controlling and actuating recirculation.

"External dialyzer" will refer to an exchange portion of the system that is adapted to be external to the patient, and a separate part of the system. Since such a dialyzer is not part of the catheter, it can be reused after sterilization, and/or its membranes replaced.

"Intralumenal" will refer to a catheter that is adapted to be placed inside an existing ventricular drainage catheter.

"Intraventricular" will refer to a catheter adapted to be used without the need for a separate ventricular drainage catheter, although optionally with other components such as an introducer, for example, by the Seldinger technique. The membrane can be anywhere along the catheter including its proximal and distal portions, and including those portions adapted to be positioned within outside the ventricle itself.

"Multiple" will refer to embodiments in which the catheter includes a combination of semipermeable membrane exchange locations, e.g., an external dialyzer in combination with an intraventricular catheter having a semipermeable membrane. By contrast, in certain other embodiments, no semipermeable membrane will be used at all, including those embodiments in which either infusion or withdrawal alone are accomplished, e.g., as shown in FIGS. 11 (in optional embodiments thereof) and 21.

The various combinations described herein can be used in further combinations, e.g., incorporating a releasable high-molecular weight substance such as albumin as a constituent, or in the form of a high-concentration solution or as a slurry coating.

The embodiments share a number of features, e.g., those that employ one or more semipermeable membranes will typically be used to indirectly control the osmotic constituency of the CSF. Unless the membrane is in intimate contact with the ventricular fluid, these embodiments generally rely entirely on intraventricular diffusion rates. The membrane can present a barrier to biological or particulate contamination. Embodiments shown in certain FIGS. (e.g., 36 and 38) will not provide intimate contact with the fluid, but intraventricular diffusion will be enhanced by the recirculation mechanism employed.

Various embodiments, including those that employ a recirculating design, will typically also include associated mechanisms to control and actuate circulation of fluid. These options include external pumps, microinfusion pumps, miniosmotic pumps, air pistons empowered by negative pressure or Venturi valves, water columns, wheel tumblers having a friction pad to control velocity, the deformation of viscous or gelatinous materials, shutter valves that open and close at differential pressures, electromagnetic switches, computer controlled servomotors, negative pressure flow turbines, and deforming bobbin seals. Actuators include tubing in which the lumen expands or contracts with pressure variation, in combination with one-way valves (e.g., slit valves or flapper valves). The tubing can be part of the housing, dedicated tubing, or semipermeable tubing. With a system of one way valves, arterial pulsations may be sufficient to produce recirculation.

Embodiments without semipermeable membranes (e.g., FIGS. 21 and 41) will not be limited by intraventricular diffusion rates. Such embodiments are less preferred, however, in view of the potentially greater risk of infection, if used without a barrier to contamination.

Embodiments having either two-way or recirculating fluid flow offer the potential for modifying the temperature of tissue coming in contact with the dialysate or the CSF, which in turn, can be used to mitigate the effects of cerebral hypoxia or damage by chemical radicals. Such embodiments can also include built-in pumping mechanisms, whereby periodic cyclic variations in trans-fiber pressure or transmural pressure can be used to disrupt and remove a local, high-concentration layer.

These and other embodiments of this invention can be made and used by employing materials and techniques within the skill of those in the related art, given the present description. For instance, the various combinations of semipermeable microcatheters and tubing described herein can be made using techniques such as those presently applied in the manufacture of hemodialysis apparatuses, including cartridges, as well as hollow membrane fiber cartridges.

Figure 18:
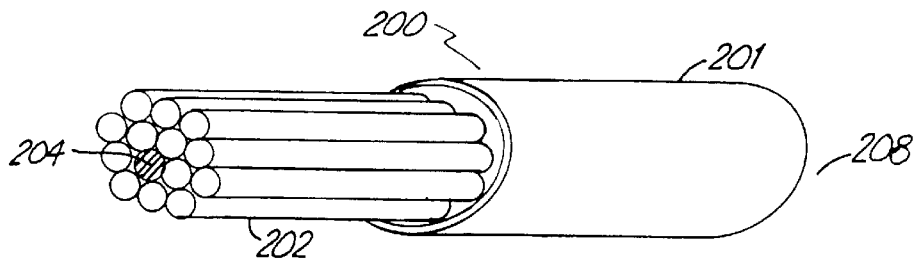
Figure 19:
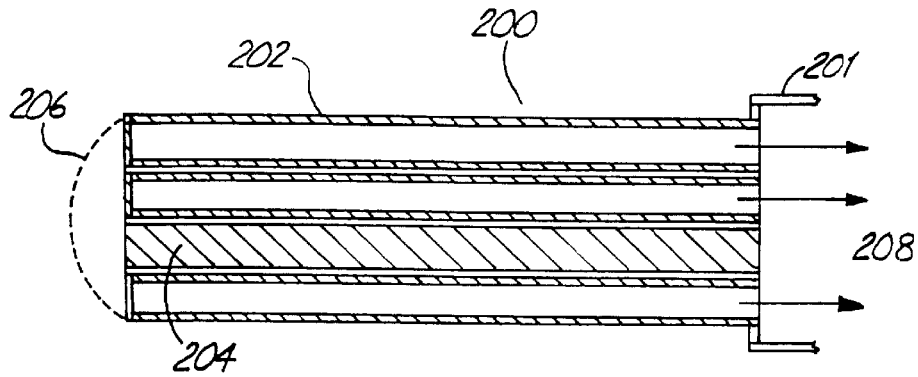
Figure 20A:
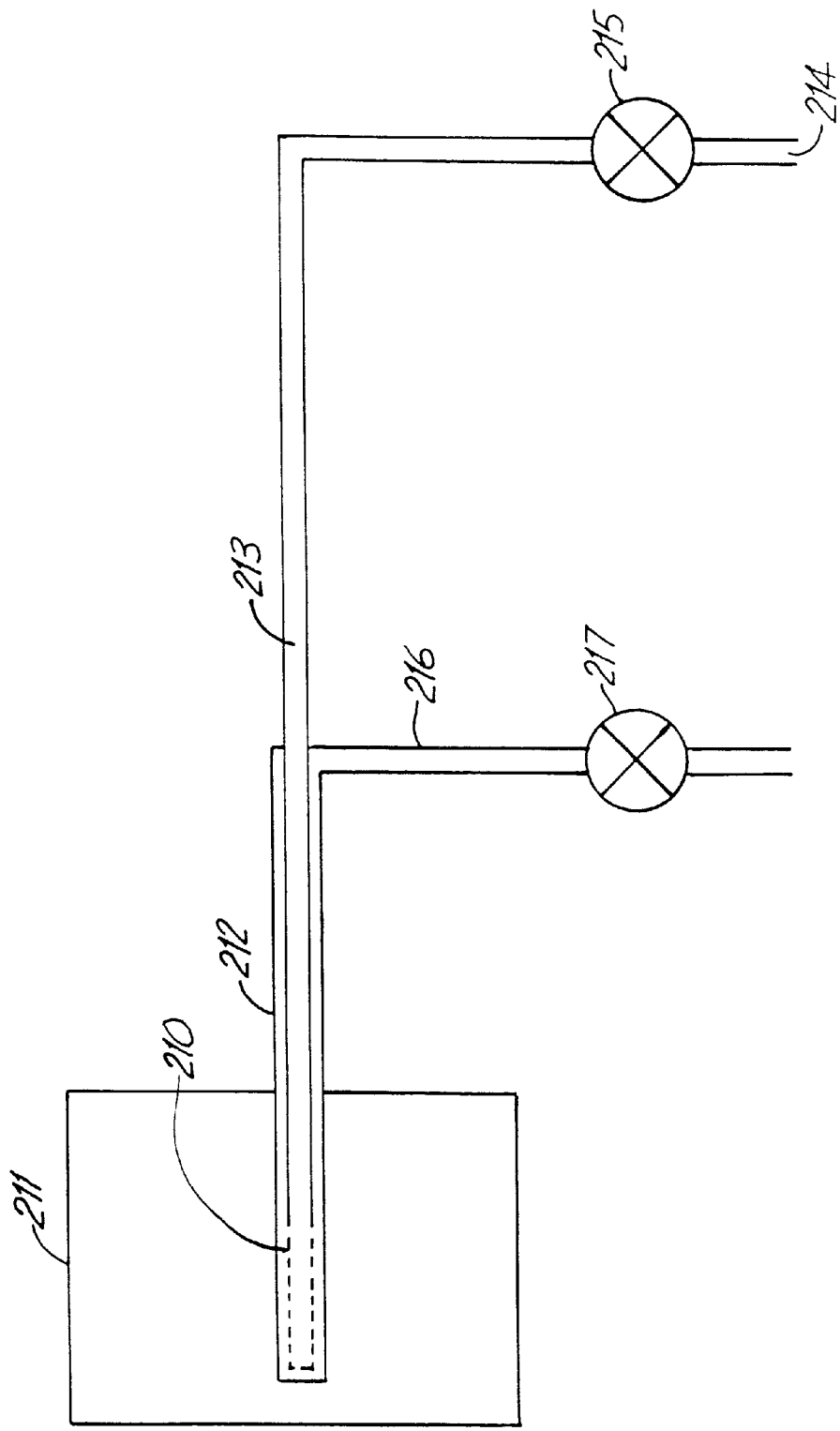
FIGS. 20a and 20b shows alternative circuit diagrams for using the apparatus to perform site specific microdialysis according to a method of the present invention.
Figure 20B:
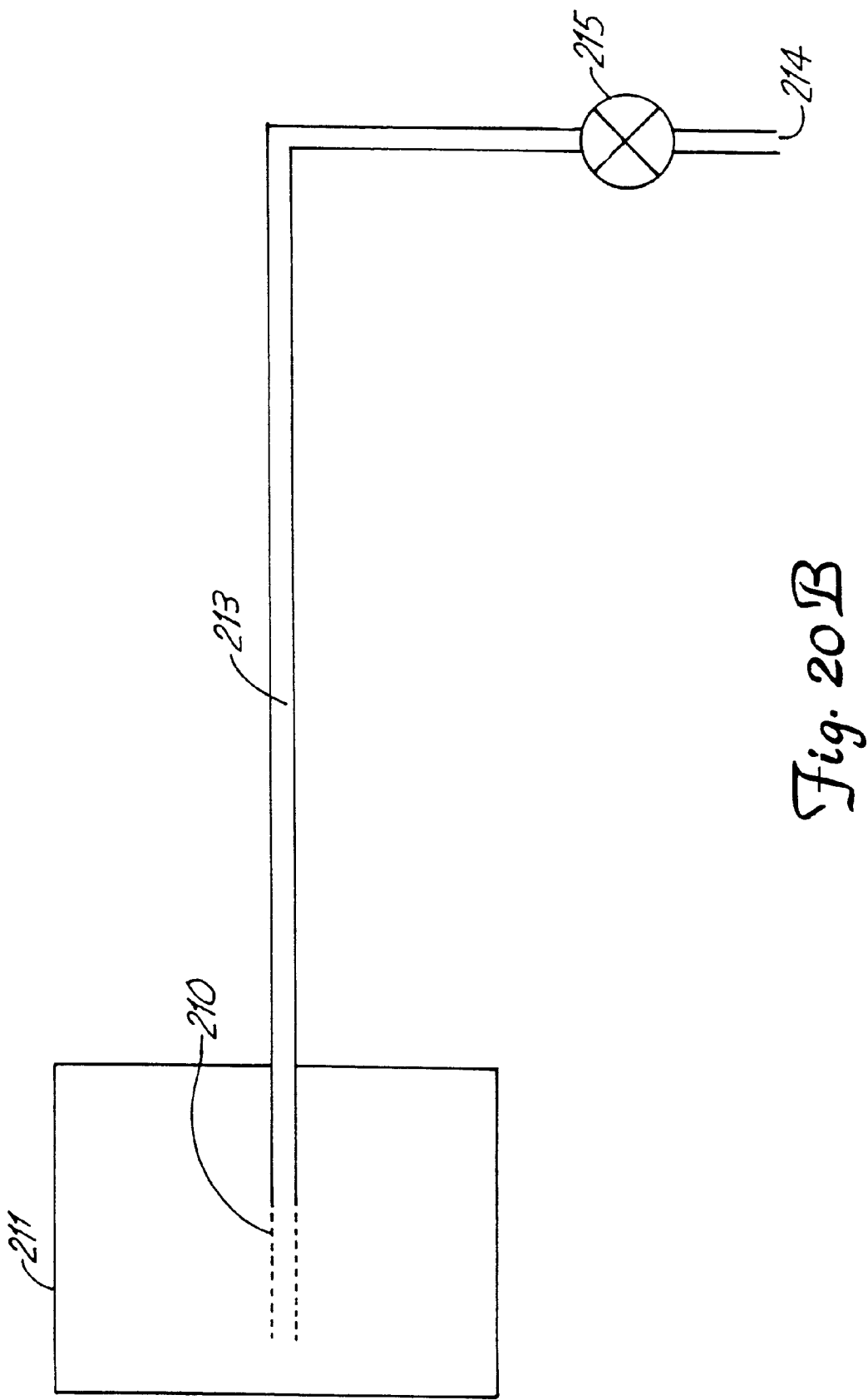

FIGS. 18 and 19 show perspective and cross-sectional views, respectively, of a preferred apparatus of the present invention, while FIGS. 20a and 20b shows alternative circuit diagrams for using the apparatus to perform site specific microdialysis according to a method of the present invention. In one embodiment, the catheter 200 is adapted to be used alone, or optionally, to be positioned within a conventional ventriculostomy drainage catheter (not shown). Toward its proximal end, the catheter provides a portion of proximal shaft tubing 201 from which emanates a distal bundle of microdialysis fibers 202. The bundle of fibers can be bound together at or near their distal ends, e.g., by the use of adhesive tip 206 or a thin, non-occlusive circumferential or coiled sheath (not shown). The semipermeable microcatheters are adapted to be connected, via the proximal shaft tubing, to a proximal source of negative hydrostatic pressure. At or near its proximal portion, the proximal shaft provides an solvent outflow port 208 for the removal of solvent recovered by the semipermeable microcatheters. At their proximal ends, the semipermeable microcatheters extend a sufficient distance (not shown), into the proximal shaft tubing, to permit them to be securely retained therein in the course of their intended use. Preferably, for instance, a bundle of semipermeable microcatheters is retained by positioning the fibers within the distal orifice of the tubing and applying an amount of a suitable flowable adhesive material, in a manner that permits the adhesive to wick into the orifice, surrounding the semipermeable microcatheters and forming, when cured, an impermeable distal plug to retain them therein.

As shown, the fiber bundle itself contains a small diameter, stainless steel delivery guide wire 204, and the individual fibers are maintained or bundled together at their distal ends by the use of a terminal adhesive plug 206. In use, the catheter can be positioned within a perforated ventriculostomy catheter and into a ventricle in the course of TBI. With negative pressure applied to the proximal portion of the catheter, water and permeant solutes (e.g., salts and low molecular weight solutes) can be removed from ventricle, through the walls of the microdialysis fibers, in a manner that leaves behind impermeant solutes (e.g., high-molecular weight solutes). The dialysate can be discarded, and extraction need not be continuous. Flow rate can be varied to indirectly control ventricular volume.

This embodiment indirectly controls the osmolarity of the fluid bathing the tissues. Unless the semipermeable membranes (making up the walls of the microdialysis fibers) are in close proximity to the perforations of the ventriculostomy drainage catheter, use of the apparatus is a function of diffusion rates within the lumen of the ventriculostomy drainage catheter. Similarly, unless the membranes are in close proximity to the tissue itself, their function is affected by the diffusion rates within the ventricular space. Alternatively, the one-way intraventricular microdialysis catheter can itself be provided with sufficient structural integrity to permit it to be positioned without the use of a standard ventriculostomy drainage catheter. Optionally, such a catheter can be used in combination with an introducer or other means to facilitate its placement and use.

FIG. 20a provides a circuit diagram showing a proposed use of the apparatus of FIGS. 18 and 19 within a conventional ventriculostomy catheter. The distal portion 210 of a catheter assembly, in the form of a dialyzying membrane, is shown within the intra-ventricular space 211 and positioned within the ventriculostomy catheter 212. A one-way circuit includes a solvent outflow path 213 that serves to remove solvent from the ventricular space, and out of the body via the solvent outflow port 214, which can be controlled by means of flow control valve 215 (e.g., a vacuum regulator). The venriculostomy catheter itself provides an optional fluid inflow/outflow path 216 and control 217.

FIG. 20b provides a circuit diagram showing the use of an apparatus according to FIGS. 18 and 19 in an intraventricular, as opposed to intralumenal, fashion without the need for a ventriculostomy catheter. The dialyzing membrane 210 is again positioned within the intraventricular space 211, and flowably connected to a solvent outflow path 213 with associate solvent outflow port 214 and controls 215.

Figure 23:
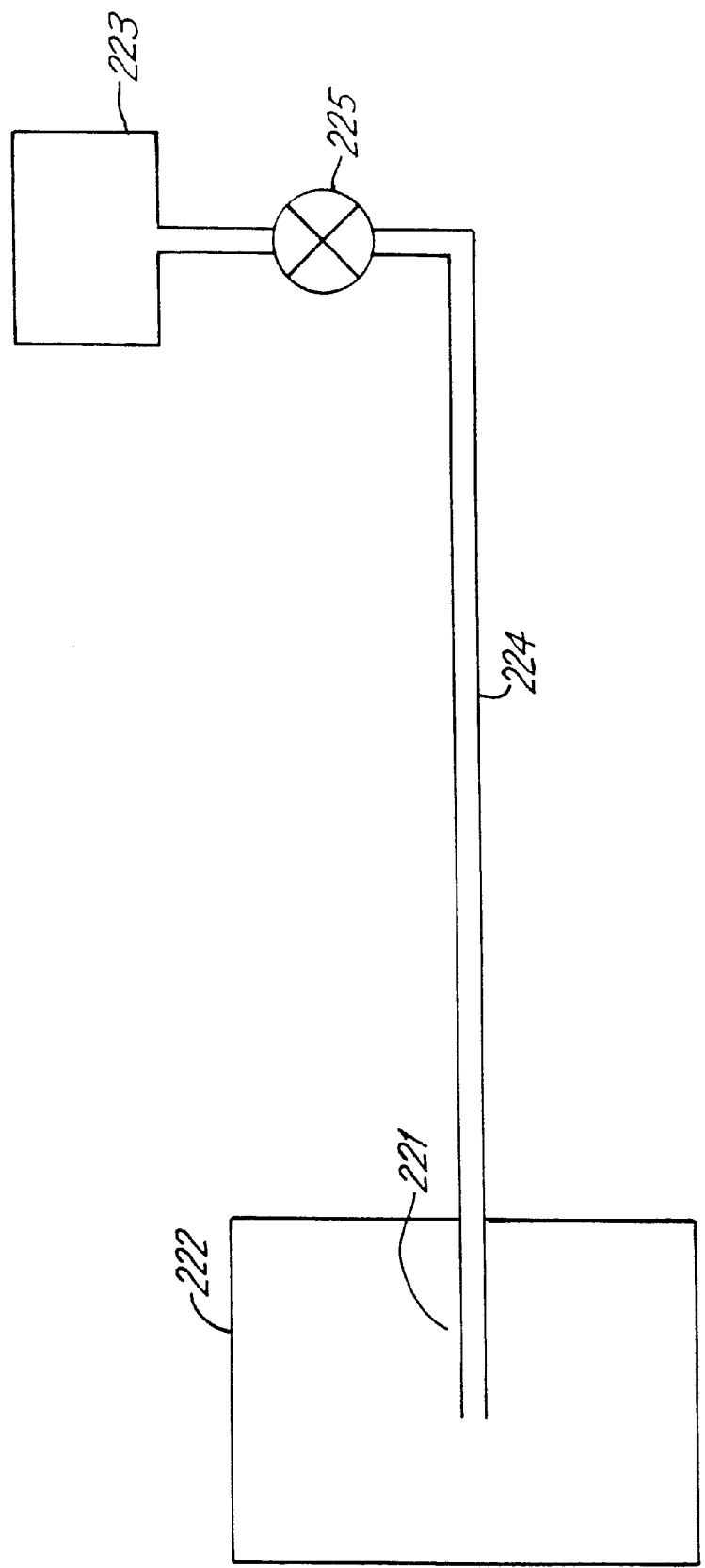
FIG. 23 shows a circuit diagram for use of the apparatus for performing intraventricular infusion by the delivery of solutions (e.g., hyperosmotic) into the ventricles under positive hydrostatic pressure.
Figure 29:
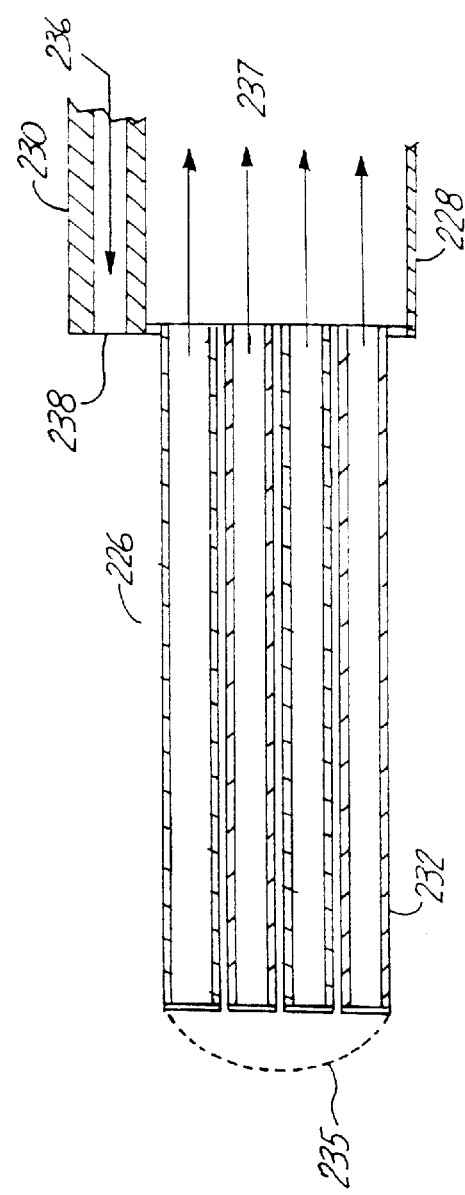

FIGS. 21 and 22 show perspective and cross-sectional views, respectively, of an alternative preferred apparatus, while FIG. 23 shows a circuit diagram for use of the apparatus for performing intraventricular infusion by the delivery of a solution (e.g., hyperosmotic) infused into the ventricles under positive hydrostatic pressure. FIGS. 21 and 22 shows an apparatus 218 for use in intraventricular infusion, wherein a hyper-osmotic solution is infused into the ventricles with positive hydrostatic pressure. The apparatus includes catheter shaft tubing 219 having one or more apertures (also known as sideports) 220 positioned in a distal portion adapted to be placed within the ventricle. Any suitable catheter can be used, including standard ventriculostomy catheters. Flow need not be continuous and the infusion rate can be varied to directly control ventricular volume. This embodiment will allow the osmolarity of the ventricle to be controlled directly, without reliance on naturally occurring ventricular osmols. This embodiment has the advantage of directly controlling the osmolarity and volume of the fluid in contact with the tissue, and it can optionally be used to control cerebral temperature.

FIG. 23 provides a circuit diagram for the use of an apparatus according to FIGS. 21 and 22. In use, the distal end 221 of the apparatus is positioned within the intraventricular space 222, and hyperosmotic fluid from source 223 is delivered via fluid inflow path 224, and controlled by flow control valve 225.

Figure 30A:
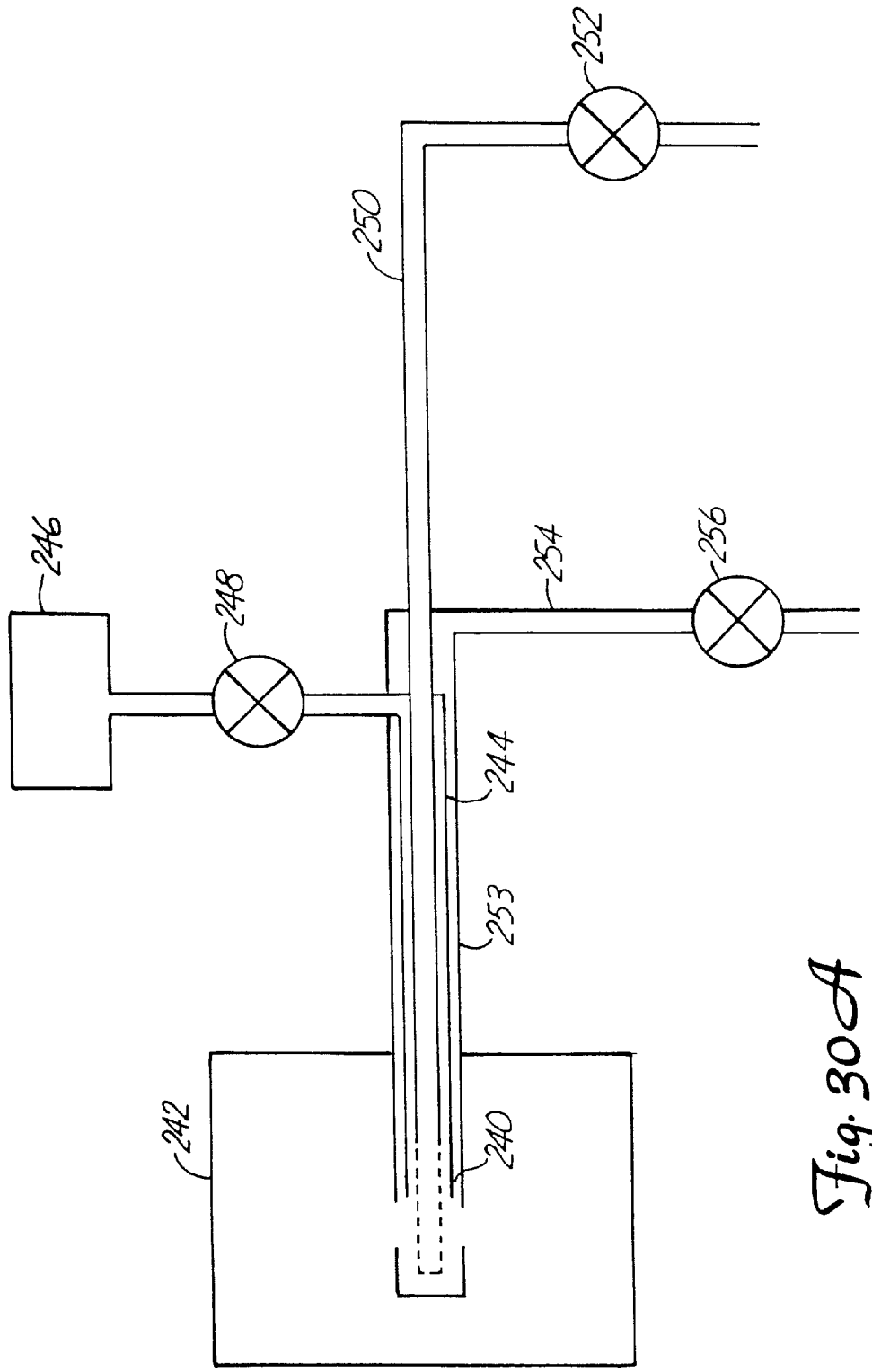
FIGS. 30a and 30b show circuit diagrams use of the apparatus in performing two-way microdialysis.
Figure 30B:
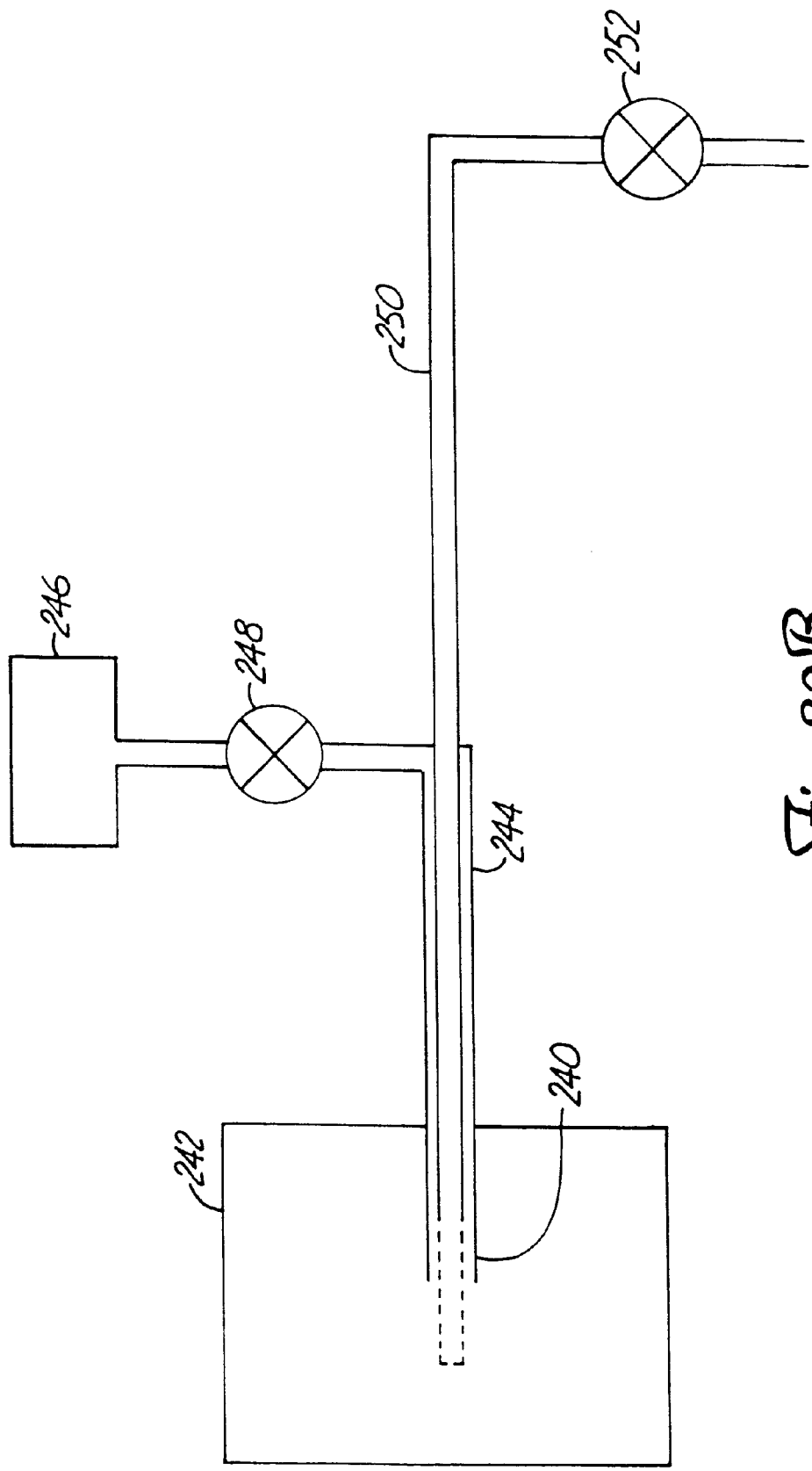

FIGS. 24 and 25, 26 and 27, and 28 and 29 show paired perspective and cross-sectional views, respectively, of another preferred apparatus, while FIGS. 30a and 30b show circuit diagrams use of the apparatus in performing two-way microdialysis. There can be seen an apparatus 226 for performing two-way intralumenal microdialysis. The apparatus includes proximal shaft tubing 228, as well as a second lumen 230 (e.g., as an inner shaft if FIGS. 24–27, and along the surface of the shaft tubing in FIGS. 28–29), in combination with one or more semipermeable membranes 232. The semipermeable membrane(s) can be provided either in the form of a single outer semipermeable membrane, as in FIGS. 24 and 25, thereby forming a coaxial dual fiber assembly with the inner shaft 230. Alternatively, the semipermeable membranes can be provided in the form of a bundle of semipermeable microcatheters (FIGS. 26/27 and 28/29).

Figure 28:
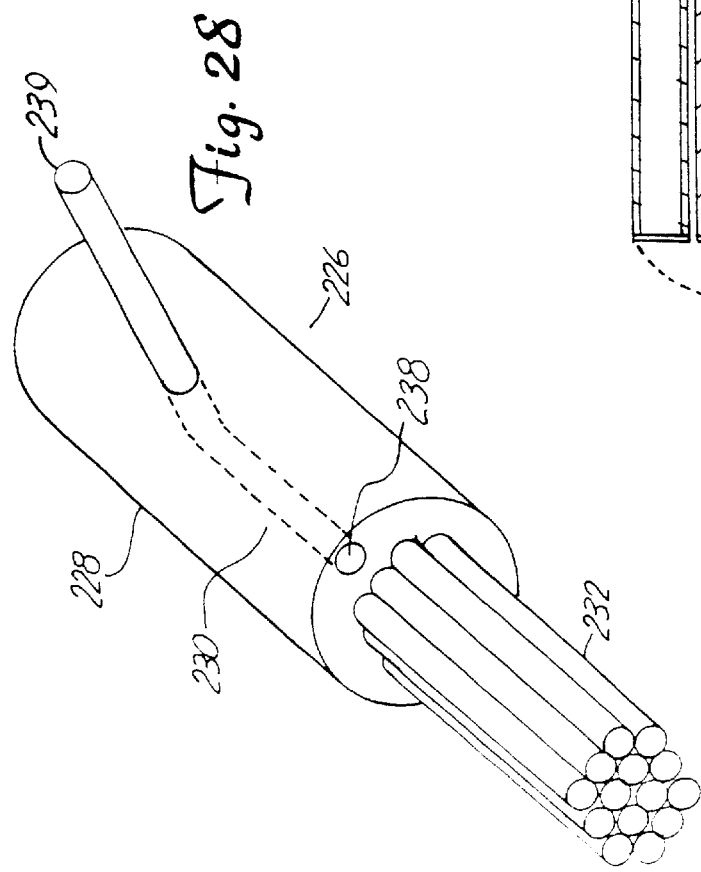

FIG. 26 shows an embodiment in which the second lumen 230 extends the distance of the semipermeable microcatheters, and exits the distal adhesive plug 235, while FIG. 28 shows an embodiment in which the shaft extends alongside the wall of proximal tubing, terminating in an orifice 238 at or near the distal end of proximal tubing 228. The second lumen can itself be either impermeable or semipermeable (for dialysis) and terminates proximally in an infusion port 239 provided by a portion shown as exiting the wall of the proximal shaft tubing. The direction of insfusion is indicated by arrow 236 while the direction of removal is indicated by arrows 237.

These embodiments provide a combination of features shown in FIGS. 18/19 and 21/22 above, and can be placed within an existing ventriculostomy drainage catheter (not shown). The apparatus is typical of embodiments in which a hyper-osmotic solution (containing molecular species to which the catheter membrane itself is impermeant) is infused through the inner shaft and directly into the ventricle under positive hydrostatic pressure. The semipermeable microcatheters allow water and permeant solutes to be removed from the ventricle while leaving behind impermeant solutes. The dialysate can be discarded, and flow need not be continuous. The infusion rate can be varied independently from dialysis rate to indirectly control ventricular volume. This embodiment allows the osmolarity of the ventricle to be controlled directly, without relying on naturally occurring ventricular osmoles. This embodiment has the advantage of directly controlling the osmolarity and volume of the fluid in contact with the tissue. The embodiment is less likely to be limited by the diffusion rates within the lumen of the ventriculostomy drainage catheter (as compared to FIG. 18) since the simultaneous infusion/removal processes will improve mixing within the lumen of the catheter and within the ventricle itself. This embodiment permits control of dialysate, and thus, cerebral temperature. The embodiment also permits the apparatus to be used to monitor pressure or sample CSF instead of continuously infusing liquid.

In an optional embodiment the apparatus is adapted for use without being placed within a standard ventriculostomy drainage catheter. A hyper-osmotic solution composed of impermeant solutes (species to which the catheter membrane are impermeant) is infused into the ventricle by dual or coaxial catheters using positive hydrostatic pressure.

FIGS. 30a and 30b both show a circuit diagram for a preferred use of embodiments as shown in FIGS. 24–29, in which the distal portion 240 of the apparatus is positioned within the intraventricular space 242 and flowably connected to both an infusion flow path 244 for the flow of a hyperosmotic fluid 246, and controlled by an infusion flow control valve 248. The distal portion 240 is also operably connected to a solvent outflow path 250 leading to a solvent outflow port, and controlled by a flow control valve 254 (e.g., vacuum regulator). FIG. 30a goes on to show the optional use of the catheter within a conventional ventriculostomy catheter 253, having its own flow path 254 and flow control valve 256.

Figure 35:
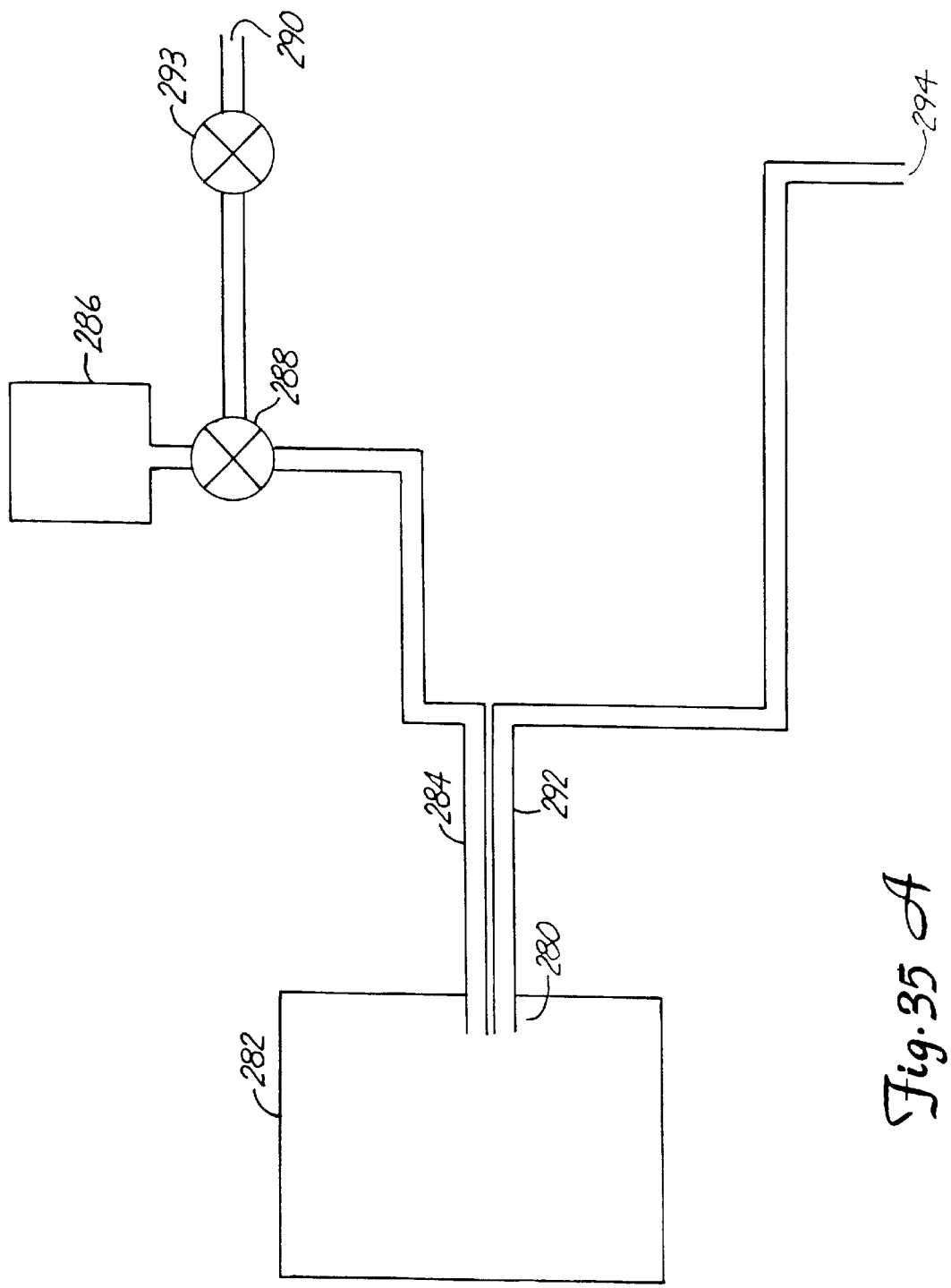
FIGS. 35a and 35b show circuit diagrams for internal or external use, respectively, of an apparatus in the form of an intraventricular infusion/withdrawal device.
Figure 35B:
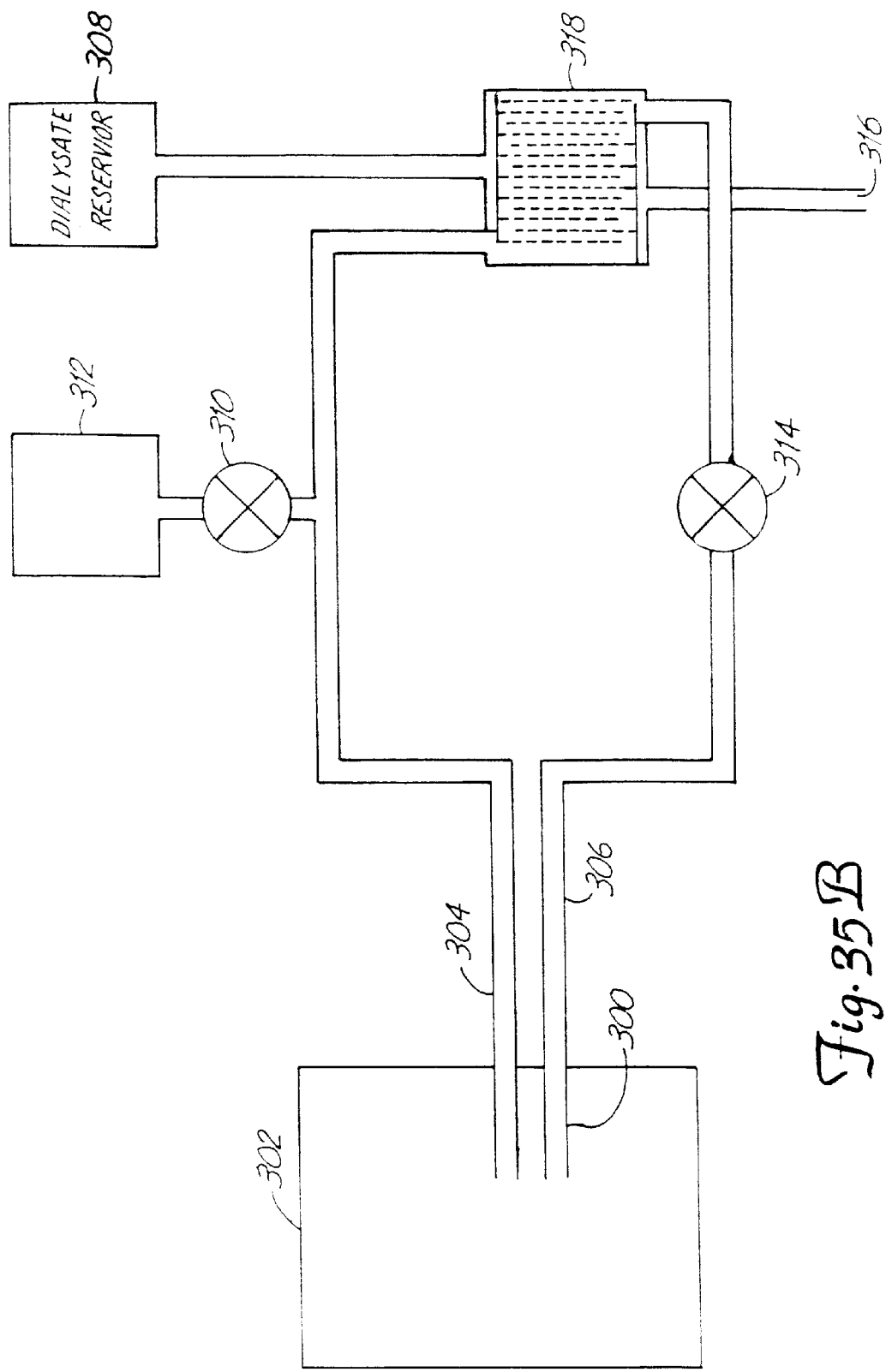

FIGS. 31 through 34 show paired perspective and cross-sectional views, respectively, of another preferred apparatus, while FIGS. 35a and 35b show circuit diagrams for internal or external use, respectively, of an apparatus 260 in the form of an intraventricular infusion/withdrawal device. Although there is no semipermeable membrane included in the apparatus itself, there is nevertheless a dialysate formed either as the result of water flowing from a remote (first) fluid to the second fluid bathing the apparatus, and/or as the result of an externally placed dialyzing cartridge. The apparatus 260 includes outer shaft tubing 262, and an inner shaft 264 terminating proximally in an infusion port 266. FIGS. 31/32 provide for the infusion of solutions via one or more sideport 268 in the wall of the outer shaft tubing, while FIGS. 33/34 provide for the infusion of solutions via one or more infusion lumen 270 terminating in orifices 272 at the distal end of the catheter assembly. The distal end of the embodiment of FIGS. 31/32, in contrast is provided in the form of an impermeable end cap 274 enclosing all but the orifice for the dialysis outflow path.

The apparatus of FIGS. 31–34 can be used to perform intraventricular infusion/withdrawal, in that it combines infusion with the withdrawal of fluid. Exogenous hyperosmotic media is infused into the ventricle (through side ports 268 in FIGS. 31/32 or through delivery lumen 270 in FIGS. 33/34) where it bathes the tissues, causing water to pass from the remote (first) fluid to the second fluid. The resultant diluted second fluid is removed from the ventricle and discarded. The flow is preferably continuous, allowing minor differentials in inward and outward flow to control ventricular volume, although flow can be tidal. This embodiment has the advantage of directly controlling the osmolarity of the fluid in contact with the tissue. This system would afford control of dialysate, and thus, cerebral temperature.

FIG. 35a shows a circuit diagram for the use of this embodiment in an internal fashion. The distal portion 280 of an apparatus is positioned within the intra-ventricular space 282, and flowably connected to a fluid inflow path 284 that includes a source of hyperosmotic fluid 286, and an associated fluid makeup valve 288, with an optional suction/sampling port 290 and associated control valve 293. The distal portion 280 is also flowably connected to a fluid outflow path 292 leading to a dialysate outlflow port 294.

FIG. 35b shows a circuit diagram for the use of this embodiment in an external fashion. The distal portion 300 of the catheter is positioned within the intra-ventricular space 302, and flowably connected to both a fluid return (inflow) path 304 and a fluid outflow path 306. The fluid inflow path includes dialysis chamber 318 and a fluid makeup valve 310 with an optional make-up reservoir 312. The fluid outflow path 306 includes a flow control valve and pump 314, and ultimately returns via a dialysate outflow port 316. Key to this circuit is the placement of a dialysing cartridge 318 for use in the manner described below.

In use, the distal catheter (e.g., in the form of the coaxial catheter of FIGS. 31/32) extracts bulk fluid from the ventricle. The fluid is passed through external dialysing cartridge 318 which extracts water (thereby concentrating high-molecular weight materials) by the use one or membranes separating the bulk fluid from a corresponding volume of hyperosmotic fluid 308. The dialysate (now higher in impermeant solutes) is returned to the ventricle, to be distributed spatially through orifices in the catheter tip sufficiently removed from the bulk fluid collection point(s). Flow is continuous, with minor differentials in inward and outward flow to control ventricular volume. This system can exert control (albeit with a time lag) on the concentration of the fluid which is in contact with the tissue. It cannot increase the concentration of species which are not present. It is not limited by diffusion rates within the ventricular space. This system would afford control of dialysate, and thus, cerebral temperature. Since the dialyzing fluid is endogenous in nature, it will typically be necessary to maintain a sterile barrier for the duration of dialysis which as the reflow system provides a structure for contaminant introduction and growth.

Figure 40:
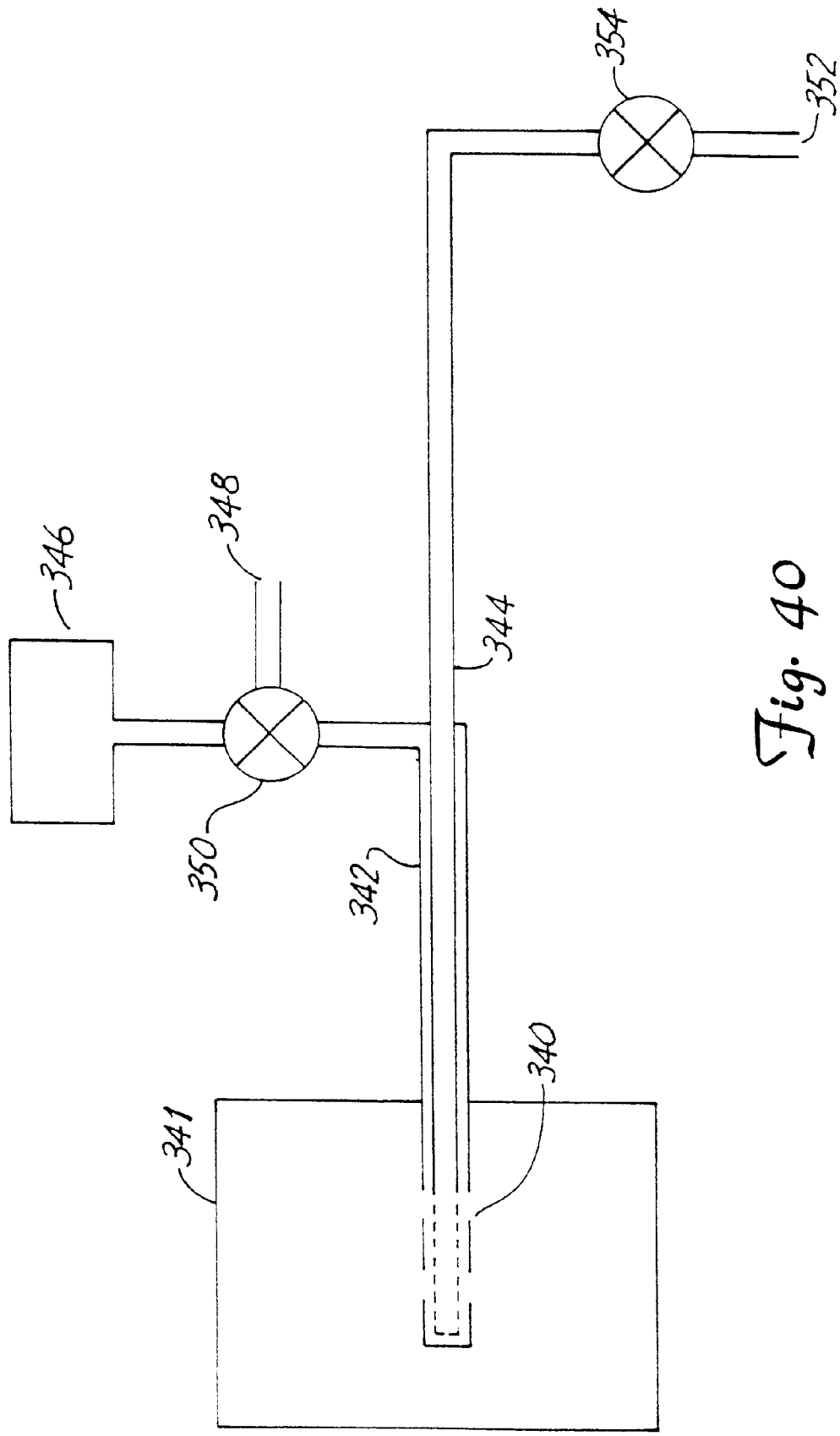
FIG. 40 shows a circuit diagram, of an embodiment which employs a principle of recirculating intraventricular microdialysis.

FIGS. 36 and 37, and 38 and 39 show paired perspective and cross-sectional views, respectively, of an alternative preferred apparatuses, while FIG. 40 shows a circuit diagram, of an embodiment which employs a principle of recirculating intraventricular microdialysis. Included in the apparatus 320 are a proximal shaft tubing portion 322 that provides a solvent outflow port 323 at its proximal end, and having included therein a plurality of semipermeable microcatheters 324 and an inner lumen 326 flowably connected to infusion port 328. As seen in the cross sectional view, the distal end of the apparatus provides an impermeable end cap 330 through which only the inner lumen is open. As seen in FIG. 37, the proximal tubing shaft 322 is extended distally in order to contain the semipermeable microcatheter assembly, but is provided with one or more fluid (e.g., CSF) inlet ports 332 and corresponding fluid outlet ports 334. The embodiment of FIGS. 38/39 show an analogous apparatus in which the inlet ports are located a considerable distance proximally, and within the proximal tubing shaft itself.

The apparatus can be used to provide "recirculating" intraventricular microdialysis in that it provides the ability to circulate the fluid within the catheter in order to improve mixing of the solution and impermeant solutes with the ventricular space. The inner lumen 326 is a dedicated fluid lumen that can be used for infusion and/or pressure monitoring. A hyper-osmotic solution can be infused into the ventricle through lumen 326 with positive hydrostatic pressure. In this embodiment inlet and outlet ports 332 and 334, respectively, permit the surrounding fluid (e.g, CSF) to circulate within the shaft tubing but outside the hollow fibers. In this manner impermeant solutes (i.e., those unable to pass into the semipermeable microcatheters) can be redistributed into the ventricular fluid. The dialysate is discarded and flow need not be continuous. Infusion rate can be varied independently from dialysis rate to indirectly control ventricular volume. This embodiment will allow the osmolarity of the ventricle to be controlled directly, without having to rely on naturally occurring ventricular osmoles. This embodiment has the advantage of directly controlling the osmolarity and volume of the fluid in contact with the tissue. There is improved mixing within the ventricle due to convective flow of the infusion. This system affords control of dialysate, and thus, cerebral temperature. Since the hyperosmotic fluid will come in contact with the tissue, sterility of the fluid is an additional concern.

FIG. 40 provides a circuit diagram showing the use of an apparatus as shown in FIGS. 37 and 38. In use, the distal portion 340 of the apparatus is positioned within the intraventricular space and flowably connected to both an infusion path 342 and solvent outflow path 344. The infusion path 342, in turn, includes an optional make-up or hyperosmotic fluid source 346 and an optional sample/monitoring port 348, together with an infusion flow control valve 350. The solvent outflow path 344 provides a solvent outflow port 352 and associated flow control valve 354.

Figure 43:
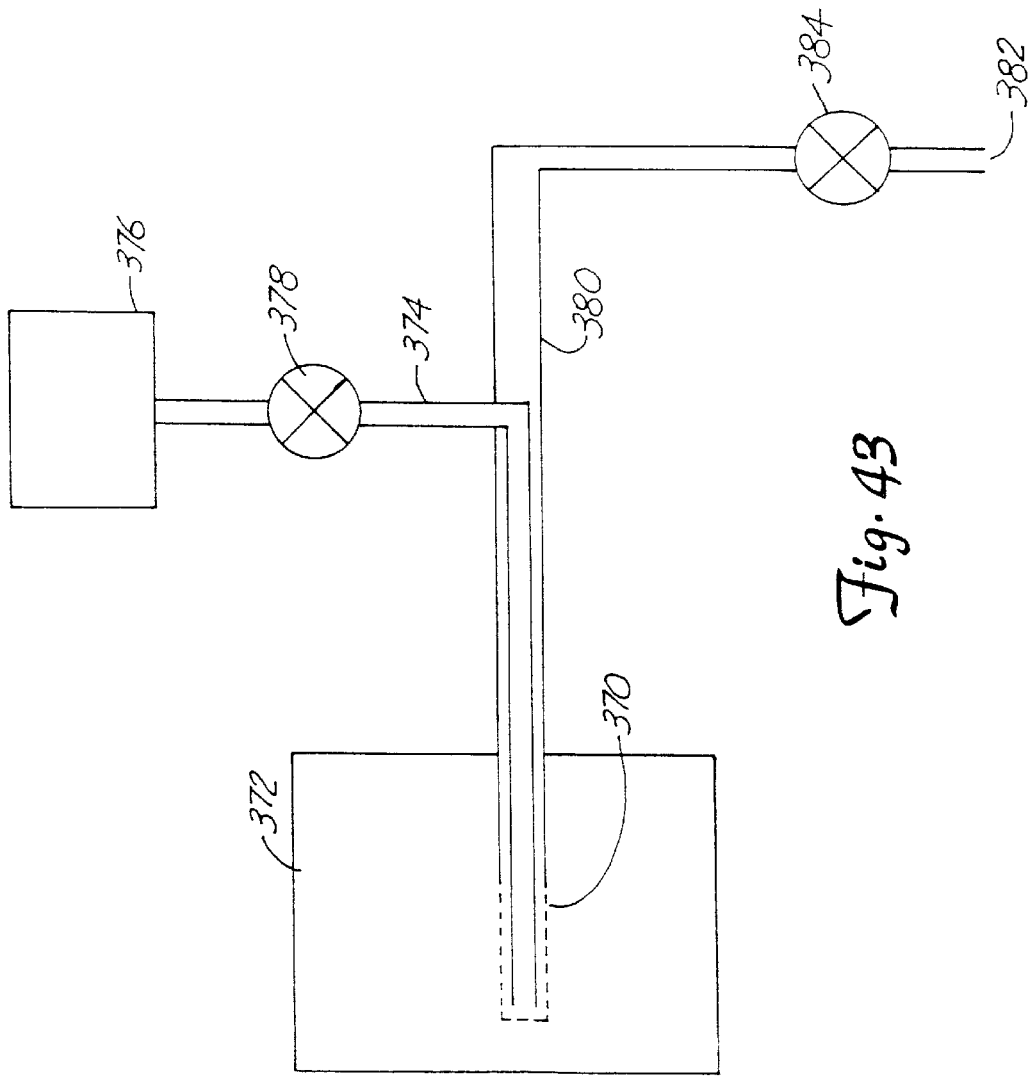
FIG. 43 shows a corresponding circuit diagram for its use.

FIGS. 41 and 42 show perspective and cross-sectional views, respectively, of another preferred apparatus, while FIG. 43 shows a corresponding circuit diagram for its use. The apparatus is provided ill the form of a "hyperosmolar loop" adapted to deliver hyper-osmotic solution through a coaxial catheter under positive pressure, and to recover water by osmosis, leaving impermeant solutes. The apparatus 358 includes proximal shaft tubing 360 together with a single semipermeable membrane 362. Contained within the membrane is an impermeable inner shaft 364 that terminates proximally in a perfusion port 366. The semipermeable membrane is itself sealed by means of terminal adhesive end cap 368. FIG. 43 shows a circuit diagram for the use of such an apparatus in which the distal tip 370 is positioned within the intraventricular space 372 and flowably connected to the fluid inflow line 374 leading to a source of hyperosmotic fluid 376 and controlled by flow control valve 378. The apparatus is also flowably connected via fluid outflow path 380 to dialysate outflow port 382 by means of optional flow control valve 384.

In use, a hyper-osmotic solution composed of species to which the catheter membrane is impermeant is passed through the coaxial catheter with positive hydrostatic pressure. The semipermeable membrane allow water to be removed from the ventricle by osmosis while leaving behind high-molecular weight materials. The dialysate is again discarded and flow need not be continuous. Flow rate can be varied to indirectly control ventricular volume. The catheter can be placed within an existing ventriculostomy catheter (intralumenal use) or it can itself be provided in an intraventricular catheter embodiment. As compared to certain other embodiments, this embodiment indirectly controls the osmolarity of the fluid in contact with the tissue. Unless the membranes are in close proximity to the tissue, this embodiment is affected by diffusion rates within the ventricle. The embodiment affords control of dialysate, and thus, cerebral temperature. The embodiment also permits the apparatus to be used to monitor pressure or sample CSF instead of continuously infusing liquid.

Figure 44:
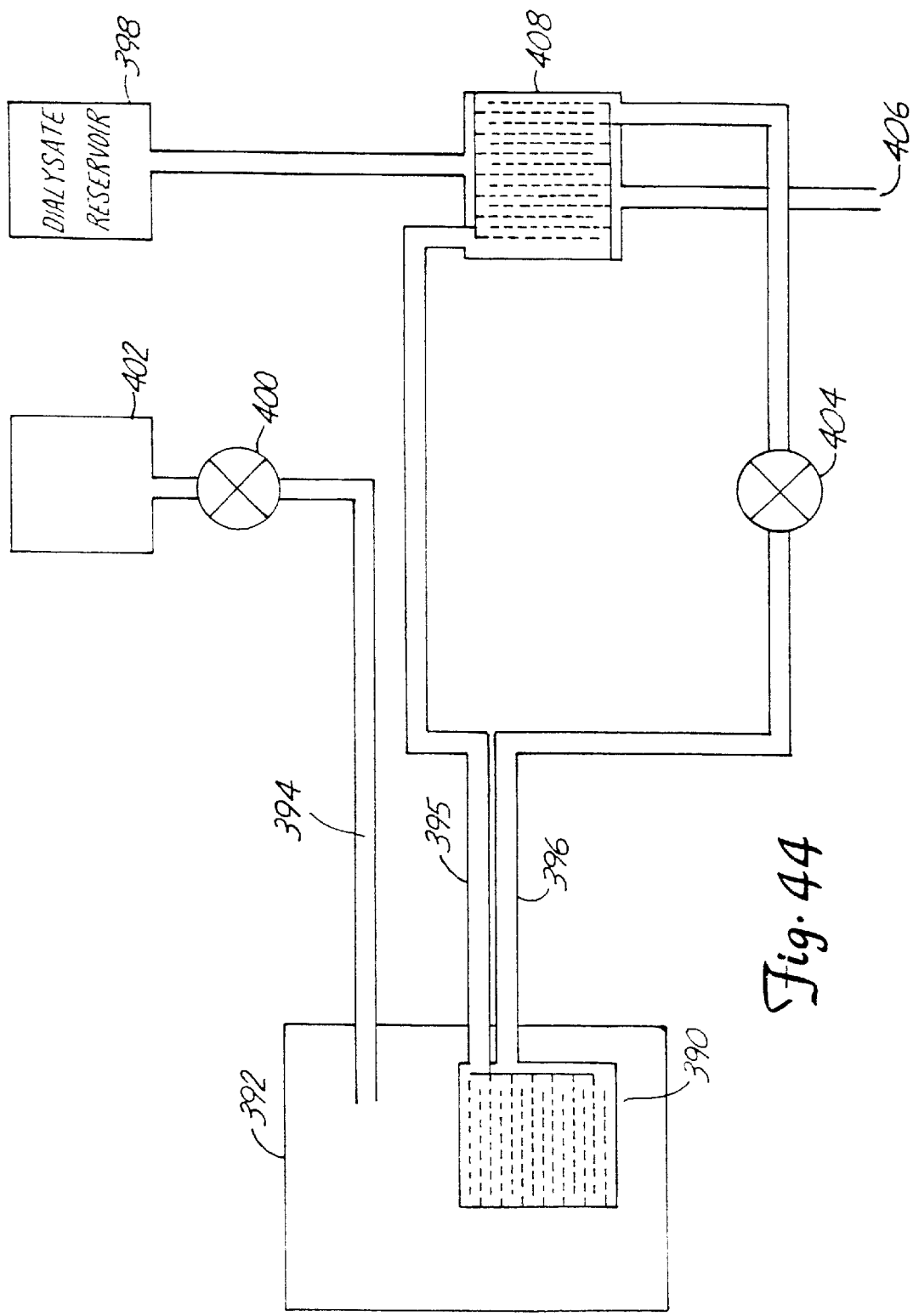
FIG. 44 shows a circuit diagram showing the use of an apparatus as shown in FIGS. 41/42 in combination with an external dialyzer circuit of the type shown in FIG. 35b.

FIG. 44 shows a circuit diagram showing the optional use of an apparatus as shown in FIGS. 41/42 in combination with an external dialyzer circuit of the type shown in FIG. 35b. The distal portion 390 of the catheter (shown in expanded view as the dialyzing unit) is positioned within the intra-ventricular space 392, and flowably connected to both a fluid outflow path 396 and a fluid return path 395. An optional fluid inflow path 394 is provided to the intraventricular space 392 as well, including an optional make-up reservoir 402 and associated fluid makeup valve 400. The fluid outflow path, in turn, leads to a flow control valve 404 leading to external dialyzing cartridge 408, and in turn, to fluid return path 395. The dialyzing cartridge also provides a path for dialysate outflow 406. This embodiment provides, in effect, a circuit analogous to that described with respect to FIG. 35b above, in combination with a intraventricular dialyzing apparatus as shown in FIGS. 41/42.

Figure 45A:
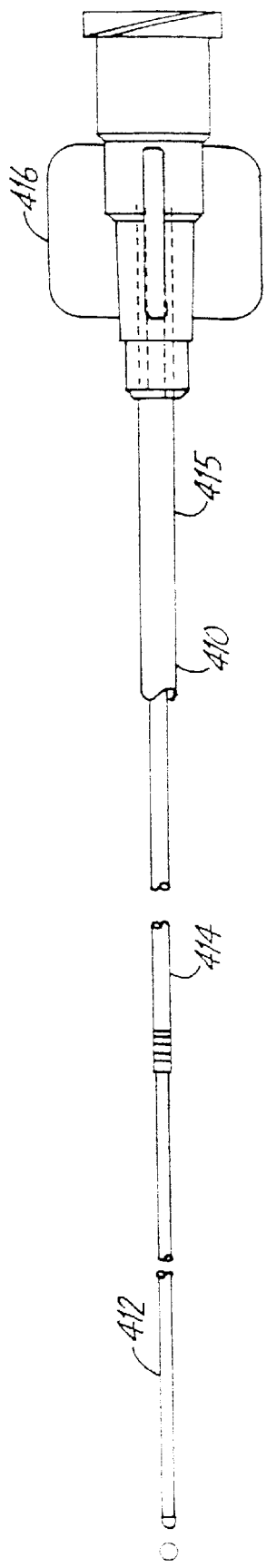
FIGS. 45(a–c) shows various views of a preferred microcatheter of the invention.
Figure 45B:
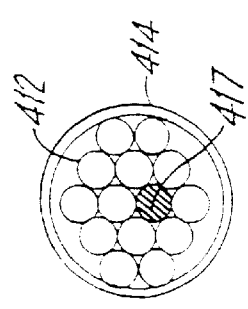
Figure 45C:
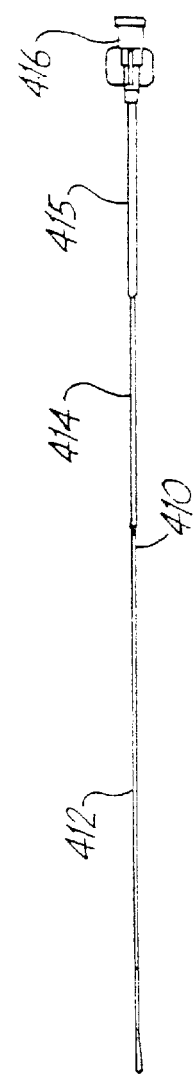

FIGS. 45(a–c) shows various views of a preferred microcatheter of the invention. FIGS. 45a and 45c show a microcathether apparatus 410 having a distal bundle of semipermeable membranes 412, and proximally, a portion of proximal shaft tubing 414, which itself terminates proximally in a portion of more rigid strain relief tubing 415. The most proximal portion shown is in the form of a luer lock hub 416. FIG. 45b shows an end view of the assembly, including the proximal portion 414 and the semipermeable membrane bundle 412. From this perspective it can be seen that the bundle optionally includes a half-hard wire 417 to facilitate its placement with the intraventricular space or intraluminally within a ventriculostomy catheter body.

FIGS. 46(a–e) shows various views of a system that includes a conventional ventriculostomy catheter in combination with the microcatheter of FIG. 45. FIG. 46a shows a conventional ventriculostomy catheter 420 within which is positioned a microcatheter apparatus of the present invention 410 and to which is attached a Y-adaptor 423 for use in alternating between the use of the catheters for their intended purposes. FIGS. 46b–46c shows an optional stylet 424 for use in positioning the microcatheter within the ventriculostomy body. The stylet includes a semi-rigid body portion 425, terminating distally in a hemi-spherical tip, and terminating proximally in a Dripping portion 426. As can be seen by the paired perspectives of the stylet 424 in FIG. 46d and microcatheter 410 in FIG. 46e, the stylet is dimensioned and adapted to be inserted into the proximal tubing portion of the microcatheter and to extend up to the proximal end of the bundled microcatheters, without penetrating them.

Figure 47:
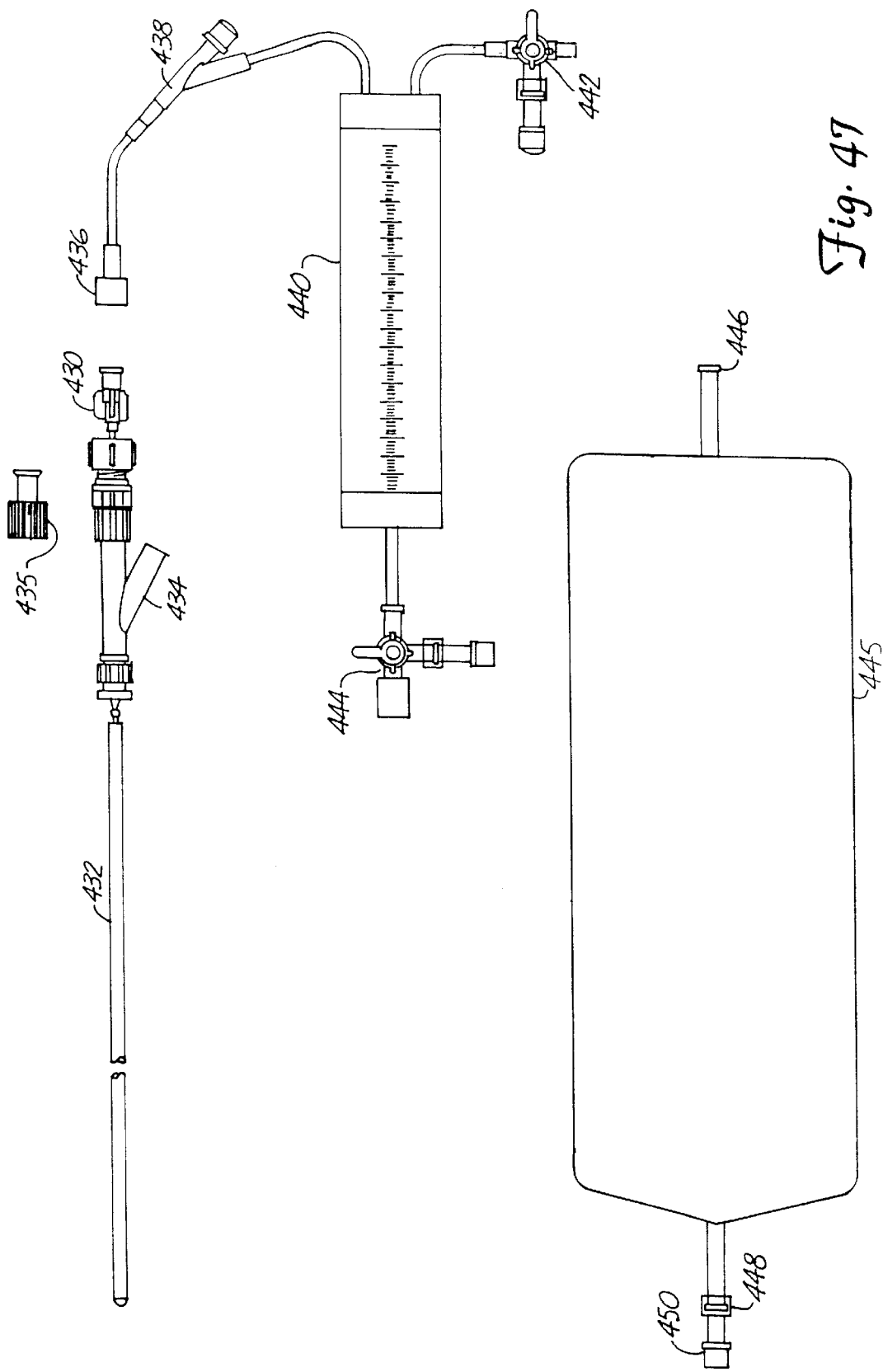
FIG. 47 shows an exploded view of the system of FIG. 46 in combination with a drip chamber and collection bag.

FIG. 47 shows an exploded view of a system that includes a microdialysis catheter 430 positioned within a ventricular drainage catheter 432 by means of Y-adapter 434, shown having a removal cap 435. To the luer hub located at the proximal end of the microcatheter is attached a second Y-adapter 438, by means of its corresponding luer adapter 436. The second Y-adapter, in turn, is flowably connected to a drip chamber 440 for use in collecting the dialysate fluid. The drip chamber is itself flowably connected by means of a 4-way stopcock 442 to a vacuum regulator (not shown) and through a second port, to another 4-way stopcock 444, for use in connecting the assembly to a collection bag 445 via a corresponding luer attachment hub 446. Finally, the collection bag 445 can be accessed by means of luer attachment 448 to a sterile port 450.

FIGS. 48(a and b) show cross-sectional and perspective views, respectively, of the system of FIG. 46 including a Y-adapter and including a preferred embodiment in which the microdialysis cathether 454 is positioned through Y-adapter 460 and within the ventriculostomy catheter 456 by means of a Touhy-Borst adaptor 458. As seen in FIG. 48a, this adapter provides a path having beveled edges 462 that facilitates the proper positioning and seating of the microcatheter body within the ventriculostomy catheter body.

Delivery/recovery mechanisms, including pump reservoirs suitable for use in an apparatus in the present invention can take any suitable form, including those used externally from the body and those implanted within it. See, for example, "Primer: High-technology i.v. infusion devices", J. S. Kwan, Amer. J. Hosp. Pharm. 46:320–335,(1989), the disclosure of which is incorporated herein by reference. Such infusion devices can be classified according to a number of criteria, including the use of pressure, the mechanism of operation peristaltic systems, syringe pumps, cassette systems, elastomeric reservoir, the frequency of delivery (e.g., continuous, intermittent multiple rate programmable, and those responsive to physiologic conditions or status), and whether they are intended for institutional or ambulatory settings.

An implantable apparatus of this invention, including pump component, can be implanted in any suitable manner, including intravenous, intra-arterial, epidural, subcutaneous, and intraperitoneal routes. Such an apparatus is effectively self-powered to deliver fluid in a desired manner (e.g., rate) over a desired period of time. When attached to a microcatheter, such pumps can be used for infusion or targeted delivery to any organ or tissue, including bone. Such pumps can be in the form of a continuous infusion pump that provides predictable delivery at controlled rate, and can be adapted to permit discontinuous or intermittent delivery. An example of a suitable pump is the pump system available under the tradename ALZET® from Alza Corporation. Such pumps operate by virtue of an osmotic pressure difference between a compartment within the pump (referred to as the "salt sleeve") and the tissue environment into which the pump is implanted.

The high osmolality of the salt sleeve causes water to flux into the pump through an outer, semipermeable membrane. As the water enters, it compresses the reservoir, displacing the solution from the reservoir at a controlled, predetermined rate. The rate of solution delivery is controlled by the rate at which water enters the semipermeable membrane and compresses the reservoir. The volume rate delivery of such a pump can be fixed during manufacture. Accordingly, the rate of delivery of any therapeutic or other agent that contained within the reservoir can be adjusted by varying its concentration in that solution.

Such pumps include, from the interior outwardly, a reservoir having a delivery portal and being surrounded by an impermeable reservoir wall, which in turn is surrounded by an osmotic agent and in turn a semipermeable membrane to the aqueous environment. In their intended application, a protein solution is provided in the reservoir to be gradually released through the delivery portal by the pressure of the solution containing osmotic agent as it takes up liquid and swells. Optionally, such pumps can include the use of accessory components, such as infusion kits (catheters for attachment to the delivery portal) to target the delivery to particular locations remote from the pump itself.

The apparatus of this invention can be provided in the form of one or more kits, including a kit in which an apparatus is provided in combination with (e.g., prefilled with) one or more solutions (e.g., of the types described herein) in the pump reservoir, and a kit in which one or more apparatuses are provided together (e.g., the monitoring and therapeutic apparatuses described with respect to compartment syndrome), optionally in combination with a delivery sheath and/or an assembly for removing interstitial fluid (e.g., as shown in FIG. 8). In each such kit, the relative amounts of materials and/or dimensions of components can be predetermined and related for application to a particular site or condition.

Suitable materials for use as hollow fibers of the present invention provide an optimal combination of such properties as mass transfer properties, biocompatability, surface-to-volume ratio, processability, hydrophobicity/hydrophilicity, strength, transport rate, and porosity. Examples of suitable hollow fibers are described, for instance, I. Cabasso, "Hollow-Fiber Membranes", pp 598–599 in *Kirk Othmer Concise Encyclopedia of Chemical Technology*.

The dimensions of a hollow fiber will depend largely on the intended use of the apparatus. In a number of preferred embodiments, a hollow fiber will be provided in the form of a capillary having an outer diameter of less than about one centimeter, and preferably less than about three millimeter, and whose outer, tissue contacting, wall functions as a semipermeable membrane. These fibers can be used singly or can be grouped into bundles, e.g. containing several hundred or several thousand. In most cases, a hollow fiber will be used as a cylindrical membrane in a manner that permits selective exchange of materials across its walls. In some cases, however, the fiber will optionally (or also) be used as a 'container' to effect the controlled release of materials from the fiber, or as a 'reactor' to chemically modify a permeant as it diffuses through a chemically activated wall.

Hollow fibers of this invention can therefore be characterized as either being 'open', in which gas or liquid permeates across the fiber wall, while flow of the lumen medium is not restricted, or as being "loaded" such that the lumen is itself filled with an immobilized solid or liquid.

Microcatheters can be prepared in any suitable manner, e.g., by microperforating an otherwise intact capillary or by spinning hollow fiber membranes from natural or synthetic polymers. Such fibers can be formed having any desired characteristics, e.g., isotropic (dense or porous) and anisotropic (assymetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like. Other examples of suitable materials include microdialysis fibers such as those identified in the following table:

| Types | Manufacturer | Catalog No. | Interior Diameter (um) | Wall Thickness (um) | Ultrafiltration Rate (mL/min) /Surface Area (sq. meter) |
|---|---|---|---|---|---|
| Cuprophan | Baxter Haemodialysis Products | unknown | 200 | 8 | unknown |
| Hemophan FoCus 160-H | Baxter Haemodialysis Products | unknown | 200 | 8 | unknown |
| Spectra/Por Regenerated Cellulose | Spectrum 23022 La Cadena Drive, Suite #100 Laguna Hills, Ca. 92653 | #132-200 through 132-313 membrane types vary according to m.w., volume, pH and chemical compatibility | 200 | 10–20 | 25-15 |
| Cellulose Triacetate CT-190 | Baxter Haemodialysis Products | CT-190 series #5M1546 CT-110-190 also available | 200 | unknown | unknown |
| Cellulose Acetate CA-170 | Baxter Haemodialysis Products | CA-170 series #5M-1735 CA-150-CA-170 series also available | unknown | unknown | unknown |
| Polysulfone Hemoflow F-60A High Flux | Fresenius | F60 series #0500136A F3-6, 8, 40-80 series also available | 200 | 40 | 40/1.3 |
| Polyacrylonitrile (PAN) | Gambro-Health | | unknown | unknown | unknown |

The method and apparatus of this invention can be applied to a number of clinical conditions, including: 1) conditions such as reperfusion injury or osteoradionecrosis, where the microcirculation is disrupted and thus the delivery of blood-borne agents is impaired, 2) conditions where tissue levels are inadequate because there is a systemic toxicity of agents such as antibiotics or antimetabolytes, and 3) conditions in which large, poorly diffusible molecules (antibodies, growth factors, enzymes, and genetic vectors) must be delivered to the interstitium.

In turn, the apparatus of this invention can be used for a variety of applications, including edema therapy, e.g., by hydrostatic or osmolar forces, in sites such as skin flap survival, compartment syndrome, cerebral edema, stroke and ischemic heart disease. Similarly, the apparatus can be used for interstitial therapy, e.g., by diffusional or hydrostatic forces, in bone microdialysis for osteoporosis, to deliver agents directly to bone, for autologous transdialysis, for interpositional bone grafts, in normal adjacent bone to dialyze growth factors, for growth factors that diffuse out in graft, and for skin flaps or grafts. In yet another embodiment, the apparatus can be used for bone marrow chemoprotection, e.g., by placing the catheter into bone marrow, to increase perfusion pressure during intravenous infusion, or to perfuse with cell culture media The method and apparatus of the present invention allows interstitial delivery and/or removal of solvent and/or solute in finite tissue spaces, without reliance on an intact microcirculatory system. Specific immediate applications include the treatment of compartment syndrome and cerebral edema, prevention of tissue necrosis of skin flaps and grafts, and infusion of large molecules (immunoglobulins or genetic vectors), antibiotics, growth factors, and chemotherapeutic agents to a specific site. Other uses include site specific treatment of osteoporosis (i.e., femoral neck), protection of bone marrow spaces during infusion of chemotherapy, and development and implantation of large three dimensional bone grafts based on a hydroxyapatite scaffolding.

Yet other uses include tissue engineering of bone, cartilage, and soft tissue implants. An engineered block as described herein, for a can be fabricated in a form that can be attached to a prosthetic implant and the combination implanted into the body. For instance, a block can be engineered as a bone replacement and attached to an other prosthetic component and the combination implanted with the engineered portion serving as the interface between the implant and the body.

A number of other conditions that rely on circulation can benefit as well from application of the present method and apparatus, including solid tumor cancer treatment, heart disease, and liver failure. With regard to cancer, the ability to treat solid tumors by chemotherapy poses at least two-challenges. The first challenge arises by virtue of the poor circulation that exists in older, more central areas of many tumors, which in turn means that agents administered systematically will not penetrate well or kill all tumor cells. Second, are problems having to do with the inherent toxicity of many, or most, chemotherapeutic agents. Although such agents are generally intended to cause cellular injury, their effect is desired only on tumor cells and not in healthy host tissues. Both of these problems can be exacerbated by poorly perfused central tumor cells, which will not effectively take up the chemotherapy. This, in turn, requires an increased dose and greater collateral cellular damage. The method and apparatus of this invention can be used to provide site-specific delivery of chemotherapeutic agents, including for agents having particular toxicity. Preferably, an apparatus for treating cancer will be in a dual catheter arrangement as described herein, with the conduit and active portion of the microexchange catheters customized to the location and size of the tumor.

In the treatment of heart disease there has been considerable interest recently in laser revascularization of the myocardium in patients having coronary artery disease. The laser addresses microcirculatory impairment. A large part of the success of the procedure has to do with draining extracellular fluid. We have shown in ischemic tissue of skin flaps, interstitial osmolarity increases along with the edema, so a solute load on the interstitial space is an important part of ischemic tissue reperfusion. Microdialysis catheters have been able to remove a hypertonic effluent from skin flaps, thereby not only reducing edema, but reducing solute load of the interstitial space. Microcatheters of an apparatus of this invention can be placed with minimal exposure or morbidity into the myocardium, producing the same benefits of the laser treatment but with even lower cost and morbidity. A preferred microcatheter apparatus of this invention, for use in treating the heart, is similar to that described above with respect to cerebral edema (both for fluid removal after ischemia), provided that the heart apparatus would preferably employ a small pliable connection tubing such as silicon to prevent tissue damage while the heart is beating.

Finally, liver failure is not a common problem but is a lethal condition. Treatment options are limited. Liver transplantation is a morbid operation and donors are limited. There are commercial entities pursuing the development of bioartificial livers, which have been shown to be technically feasible, but are limited to extracorporeal use. The method and apparatus of the present invention, however, can be used to create an implantable artificial liver. The technical challenge to this endeavor is having sufficient vascularity of the implant to allow meaningful perfusion of hepatocytes. It is conceivable that microdialysis fibers, angiogenic growth factors, and actual vascular anastomoses to cultured vessels will make an implantable liver possible. A preferred apparatus for treating the liver will be in the form of a three-dimensional apparatus as described above in the context of tissue engineering, preferably also including the use of resorbable scaffoldling, such as resorbable hydroxyapatite. Other forms of organogenesis, such as the growth of islet cells for diabetics, will be made possible as well.

The invention will be further described with reference to the following non-limiting Examples.

EXAMPLES

Example 1

Rat Model

Cerebral edema is induced in rats, and thereafter reduced by the use of microdialysis fibers implanted directly into injured brain tissue. As an initial experimental phase, a hyperosmolar solution of albumin is infused into the ventricles of the rat after experimental brain injury has been induced. Conventional methods (e.g., Onal et al.) are used to induce the injury, with the following exceptions: a contusion injury is used and infusion is performed over a longer period to see if the benefits of infusion can be prolonged. Twelve hours after experimental TBI is induced, an infusion catheter is placed into the lateral ventricle. Thereafter a 20% (w/v) solution of albumin in saline is infused at 0.5 ul/hour for a period of six hours. Brain water content is determined at 24 hours.

In a subsequent phase, the effect of intraventricular microdialysis on brain water content is determined. Some impermeant solutes are already present in the ventricles (and the concentration of large molecules may increase after trauma). The osmolarity of the ventricular fluid is increased by either infusing additional impermeant solutes into the ventricle, or by removing solvent component from the ventricle with a microdialysis catheter which will leave behind natural active osmoles.

Twelve hours after experimental TBI is induced, a semipermeable fiber is placed into the lateral ventricle using stereotaxic instruments and published coordinates. Two rates of dialysate recovery are tested, and treatment continues for six or 18 hours. Treatment in the six hour groups is done with the animals lightly anesthetized. Treatment for the 18-hour group is done with the animal awake using a swivel system to allow animal movement. At the end of the treatment period, ventricular fluid is sampled for determination of osmolarity. Brain water content is determined at 24, 36, and 48 hours, depending on treatment limb.

In a further phase, brain edema caused by TBI is treated with combined intraventricular infusion and microdialysis. Such an approach is preferred in situations where there is not enough id naturally occurring active osmols in the CSF to significantly reduce brain edema. The third approach is performed in the manner set forth in the second phase described above, and effectively combines phase one and two treatments in an attempt to maximize duration and magnitude of treatment.

Control animals are studied as well, having similar injury, and probe placement, but no treatment administered with the probes. Sham injury controls are used to evaluate the effects of placement of the probe uninjured cerebral tissue. Sham operated controls have probes implanted into the ventricle, but they do not experience craniectomy or TBI. The rat model further confirms that the present method and system can be used to reduce brain edema after TBI.

Example 2

Osmolarity of Human Traumatic CSF

A study was performed using banked human CSF. Osmolarity was determined in control patients (no head trauma), and three patients who suffered closed head injury. Normal osmolarity of CSF in the controls was 305 mosmols/L. As seen in Table I below, the TBI patients had an increase in CSF osmolarity in the first 3 days, with an even greater increase in the next three days.

TABLE I

CSF Osmolarity in Human Head Trauma Patients

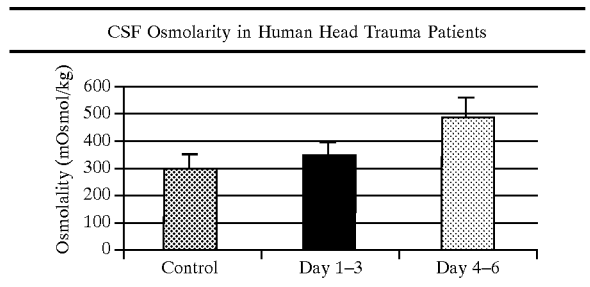

These findings of a delayed increase in CSF osmolarity are consistent the osmotic fluid shift premise described herein. Although CSF from trauma patients has apparently not been examined for changes in osmolarity before, and it is difficult to make conclusions based on this small number, it nevertheless appears that CSF osmolarity does increase after head trauma. This finding, together with findings in the literature that CSF osmolarity increases after a cryogenic injury in rats, and that brain tissue osmolarity increases within hours after ischemia provides support for the concept of direct ventricular osmotic treatment by intraventricular microdialysis.

In Vitro Dialysis Rates in Human Traumatic CSF

Multiple semipermeable microcatheter catheter systems (using various dialysis fiber types with a wide range of molecular weight cut-offs) have been fabricated and have undergone extensive testing in various fluid solutions (ranging from saline to artificial CSF) to assess their abilities to extract fluid and/or alter ionic compositions. These catheters were evaluated using human traumatic CSF, as an environment most likely to predict catheter performances in vivo. Banked (frozen, then thawed) and fresh CSF from TBI patients was tested in vitro with candidate catheters using various solutions. The catheters tested had different semipermeable membranes, which affect the size of the molecules left behind in the CSF and also affect the rate of fluid recovered (in general, the smaller the pore size the slower the fluid recovery). Provided in TABLE 2 below are the fluid recovery rates of several catheter embodiments when tested at a negative 180 mmHg pressure while submerged in CSF bath. The data shows that the polysulfone catheter has the highest fluid recovery rate, while also being able to exclude albumin (69,000 daltons). The final column shows the estimated fluid recovery rate for a catheter composed of 11 semipermeable fibers that are 20 cm long.

TABLE 2

| Membrane | Molecular Wt. Cut Off | Fiber Fluid Recovery | Catheter Fluid Recovery |
| --- | --- | --- | --- |
| Cuprophan | 10,000 daltons | 0.45 uL/min/cm | 0.54 mL/hr |
| Polyacrylonitrile (P.A.N.) | 50,000 daltons | 1.86 uL/min/cm | 2.23 mL/hr |
| Polysulfone (P.S.) | 68,000 daltons | 7.29 uL/min/cm | 8.75 mL/hr |

Catheter Osmolarity Study

Since the microcatheters prepared with P.A.N. or P.S. membranes showed the greatest catheter fluid recovery, these fiber designs were evaluated in vitro to determine if they could be used to alter CSF osmolarity. The catheters were placed in a bath of human traumatic CSF over an eighteen hour period at negative 90 mm Hg pressure. In TABLE 3 below it can be seen that, compared to CSF osmolarity before activation of negation pressure, the osmolarity of the CSF bath increased after eighteen hours of fluid removal with either P.A.N. or P.S. membranes.

TABLE 3

| Membrane | Before | After |
| --- | --- | --- |
| P.A.N. | 308 mOsmol/kg | 309 mOsmol/kg |
| P.S. | 313 mOsmol/kg | 315 mOsmol/kg |

This small increase in mosmols is significant due to the relationship of osmolarity and hydrostatic pressure. According to vant Hoff's law, one mosmol is equivalent to 25 cm water hydrostatic pressure.

Clinical Function and Safety

A study is performed to test the functionality and safety of a microcatheter assembly. Subject candidates are chosen having a ventriculostomy in place and having normal or only a mild elevation in ICP ($\leq 15$ mm Hg). In these selected patients, microdialysis fibers are placed into the ventriculostomy catheter while fluid recovery rates and intracranial pressure are monitored. The study lasts for four hours.

While a reduction of brain tissue edema is the ultimate therapeutic goal, fours hours is probably not long enough to achieve this effect. Also, methods to quantify reduction of tissue edema, such as diffusion scanning MRI, are difficult to obtain in multiple-injury TBI patients without risk. Therefore brain edema is not an outcome measure of this study.

This study demonstrates that such catheters can: 1) be safely placed within pre-existing ventriculostomy catheters (without interfering with ICP monitoring or reducing capability of ventriculostomies to provide passive drainage), and 2) be used to collect sequential samples of CSF and provide equivalent (100% recovery) values for CSF constituents whose molecular weights are below the cut-off range of the dialysis fibers used in the catheter assembly (e.g., electrolytes, glucose, lactate).

Also, osmolarity is tested in the CSF pre- and post-treatment, and in the effluent from the catheter assembly. Measured ventricular CSF osmolarity may increase only slightly with treatment. Measured osmolarity includes large, impermeable, osmotically active molecules and smaller permeable molecules (such as salts). The small molecules are in much higher concentration and are removed with water by the microdialysis fiber. Therefore, the salt concentration will typically change very little with treatment. As long as large, osmotically active agents are left behind in the ventricle, there is an osmotic gradient to move fluid from the tissue into the ventricle.

In certain embodiments, the present system relies on considerations having to do with which osmoles are "active" (impermeable to the ependyma). Examples of likely impermeant solutes include immunoglobulins, albumin, glycerol, proteins, amino acids, and neurotransmitters. Albumin is most likely to be an important osmole, and is well suited to be quantified for study.

Specific aims of the study include:
1. To demonstrate that the prototype intraventricular microdialysis catheter can be placed safely.
   a. Intraventricular pressure can still be monitored with the catheter in place.
   b. Cerebrospinal fluid can still be removed for sampling with the catheter in place.
   c. Presence and use of the catheter will not result in an increase in infections.
2. To demonstrate that intraventricular microdialysis catheter will remove fluid.
   a. Fluid removed rate is quantified.
   b. Dialysate can be collected while simultaneously monitoring ICP.
   c. The dialysate and ventriculostomy catheter effluent is analyzed for osmolarity and molecular/chemical contents.

Catheters with PS 68 membranes and necessary equipment is sterilized prior to use.
Patient Inclusion Criteria
1. Patients admitted to the study will be between 18–75 years of age.
2. Primary injury is to head and brain. This will include patients with first-time closed head injury.
3. Patients to be entered into the study must have had a ventriculostomy performed as standard medical care and monitoring.
4. Data must be available on the extent and location of the primary injury and on positioning of the ventriculostomy as determined by CT scan.
5. The ICP measured via the ventriculostomy will be no lower than 10 mm Hg and no higher than 15 mm Hg at the time of study entry.
6. Ventriculostomy drainage must average at least 2.5 ml/hour within the four hours prior to the study.
7. Glasgow Coma Scale must be between 4 and 8, and at least one pupil is reactive.
8. Informed consent from the patient's family must be given for participation in the study.
9. The attending neurosurgeon will give permission for treatment.

Exclusion Criteria
1. GCS of 3 or both pupils fixed/dilated.
2. ICP greater than 20 mm Hg at any time since ventriculostomy placement.
3. Patients with prior brain injury.
4. CT or CSF drainage shows evidence of intraventricular hemorrhage.

Standard protocols and records are employed throughout the study period to determine important clinical characteristics and profiles for each patient. This will include information on age, sex, admission (pre-sedation, or post-resuscitation if appropriate) GCS, etiology of the injury, all medical interventions and treatments, and morphological aspects of the injury as determined by CT scan.

Information from the standard ICU flowsheet is transferred to a study data sheet to establish a 4 hour baseline information on each patients condition. Recorded measures include the hourly readings of mean arterial blood pressure (MAP), heart rate, core temperature, ICP, cerebral perfusion pressure (CPP) and GCS and the volume of CSF drainage during the past 4 hours (per orders specified by the attending neurosurgeon).

Immediately preceding catheter insertion a CSF sample is obtained and utilized to obtain measures of: glucose, lactate, osmolarity, cell count, protein, and electrolytes. A portion of this sample is sent to the clinical lab for culture testing. At this same time the MAP, heart rate, ICP and CPP is recorded on the experimental data sheet.

Under sterile technique, a "Y" adapter is connected to the ventriculostomy catheter hub. The proximal port of the "Y" adapter is connected to the CSF drainage and pressure monitoring apparatus. The side port of the "Y" adapter is opened under sterile conditions and the microdialysis catheter is placed within the ventriculostomy catheter and slowly advanced. Once the catheter is advanced completely, the hub is resealed. The ventriculostomy drain remains closed to atmosphere, and pressure readings from the ventriculostomy catheter are continued. The microdialysis catheter is then put in place to suction at −180 mm Hg. Immediately after insertion/placement of the intraventricular catheter the MAP, heart rate, ICP and CPP are again recorded on the experimental data sheet.

ICP is monitored continuously during the study. The ventriculostomy catheter is closed to drainage but open to the pressure transducer. MAP, heart rate, ICP and CPP is recorded every 15 minutes during the ensuing 4 hour treatment period. The GCS evaluations, taken by the ICU nurse, as well as core temperature, are recorded hourly. Dialysate collection rate is monitored during this time. If recovery rates of CSF dialysate fall below 500 ul per minute for more than 30 minutes the test is stopped and the microdialysis catheter is removed.

The study continues for 4 hours. Immediately prior to withdrawal of the IVMD catheter, the ventriculostomy catheter is put to drainage and 1.2 ml of fluid (approximately 0.8 ml of dead space to be discarded and 0.4 ml of intraventriculostomy catheter volume to be analyzed) is collected passively. This CSF, recovered from within the ventriculostomy catheter (but outside the microdialysis fibers), contains concentrated CSF osmols and is used for analysis of glucose, lactate, osmolarity, cell count, electrolyte, and protein composition. The IVMD catheter is then be removed. A second CSF sample of 1 ml, more reflective of ventricular CSF, is obtained immediately after withdrawal of the IVMD catheter and used to obtain post-treatment measures of: glucose, lactate, osmolarity, protein, and electrolytes. A portion of this sample is sent to the clinical lab for bacterial culture.

If any reductions in ICP are noted, the IVMD pressure is adjusted to ensure that ICP does not drop below 8–10 mm Hg. The CPP is closely monitored and if the CPP drops below 60 or exceeds 80 the catheter is removed. If ICP is above 16 mm Hg, the ICP catheter is immediately opened to enable CSF drainage, the catheter is promptly removed and the experiment terminated.

| ICP Levels | Action |
| --- | --- |
| <8 mm Hg | Adjust IVMD pressure to atmosphere |
| <10 mm Hg | Reduce magnitude of negative pressure on IVMD catheter |
| >10, ≦16 mm Hg | Collect ventriculostomy catheter drainage after four hours |
| ≧17 mm Hg | Open ventriculostomy catheter, remove microdialysis catheter, terminate study |

Data sets are recorded just prior to and just after IVMD removal. The "Y" adapter is capped and left in position after the study so there is less chance of bacterial contamination by interruption of the system. The standard ICU flowsheets are used to collect data on post-treatment physiological parameters of each patient, including measures of MAP, heart rate, core temperature, ICP, CPP, GCS and the volume of CSF drainage during the 4 hour period immediately following cessation of the experimental protocol.

The day after application of this treatment protocol the final CSF sample is obtained and sent to the clinical lab for culture testing. The chart is reviewed for CSF cultures (that might have been ordered by the attending neurosurgeon) at seven days after the testing to be certain there were no infections. The patient chart is reviewed six months after treatment to ascertain long term outcome: if six months outcome cannot be determined from the chart review, patient and/or family members well be contacted by telephone to ascertain the Glascow Outcome Scale (GOS)—a five point rating of deficit ranging from good recovery to death, and the Rancho Los Amigos Cognitive Outcome Scale—an eight point assessment ranging from comatose/vegetative, to normal purposeful responses.

The extracted fluid is collected and the total volume is analyzed for glucose, lactate, osmolarity, protein, and electrolytes after collection is completed. A paired t-test is used for before and after measures. The ventriculostomy catheter effluent is tested for hemoglobin and red blood cell counts. Albumin is the priority for protein assay. Osmolarity is compared pre and post dialysis using paired t test. Cultures are reviewed to be sure there is no increased incidence of infection.

The present study demonstrates that:
1. The prototype intraventricular microdialysis catheter can be placed safely.
   a. Intraventricular pressure can still be monitored with the catheter in place.
   b. Cerebrospinal fluid can still be removed for sampling with the catheter in place.
   c. Presence and use of the catheter will not result in an increase in infections.
2. That the intraventricular microdialysis catheter will remove fluid.
   a. Fluid removed rate is quantified.
   b. Dialysate can be collected while simultaneously monitoring ICP.
   c. The dialysate and ventriculostomy catheter effluent are analyzed for osmolarity and molecular/chemical contents.

Example 3

Spinal Microdialysis

The method and system of the present invention are used to perform spinal microdialysis using the following materials:

1. A 3 inch needle, 18–20 gauge, similar to contemporary spinal tap needles. This is placed between the third and fourth lumbar vertebral space. The distal 2 mm of the needle is unique in that it has a memory to bend 50–70 degrees when the obturator of the needle is removed.
2. The obturator of the needle is straight, rigid, and has a lumen.
3. The patient assumes a lateral decubitus position with knees drawn up. The L3-4 interspace is palpated and marked after sterile scrub of the skin.
4. The spinal needle with obturator in place is advanced until a slight decrease in resistance is felt as the needle tip pierces the posterior spinal ligament and enters the spinal canal CSF space.
5. Once CSF is confirmed to drip from the lumen of the obturator, the obturator is held stationary and the needle is advanced another 2–3 mm. This allows the tip of the needle to then point toward the brain.
6. The obturator is withdrawn and the microdialysis fiber is advance through the spinal needle. The microdialysis fiber will travel towards the brain in the subarachnoid space of the spinal canal. The fiber can be advanced as far as possible, from a few millimeters to 20 or more centimeters. The farther it is advanced, the more surface area for exchange. However, care must be taken not to force advancement to avoid damage to the spinal cord, vessels, or nerve roots.
7. The needle can be withdrawn from the tissue, leaving the microdialysis catheter in place. The needle can be secured externally during microdialysis.
8. Once positioned, negative hydrostatic pressure is applied to the microdialysis fiber with an apparatus similar to that for ventricular microdialysis.
9. The proximal tubing, any unused (unadvanced) microdialysis fiber, and the needle is covered with a sterile dressing, similar to central venous lines.

Other optional embodiments include the use of a larger introduction needle, using coaxial or double lumen catheters. Multiple fibers can be placed, with a combination of infusion ports along with the microdialysis fiber to simultaneously infuse an agent while doing microdialysis. Other monitor ports or sensors can be added as well. The apparatus can be placed in the lumbar area with least risk, but it can also be placed higher in the spinal canal.

What is claimed is:

1. A system for performing site specific therapy of a tissue site, the system comprising one or more catheters, each comprising one or more semipermeable membranes in the form of hollow fibers adapted to be positioned within the tissue site, and a delivery/recovery mechanism for employing the catheter(s) to control the movement of bulk fluids within tissue portions in a manner that achieves a therapeutic effect, wherein the delivery/recovery mechanism comprises a source of negative hydrostatic pressure adapted to recover bulk fluids and/or water and permeant solutes through the semipermeable membranes and from the tissue site, and wherein the hollow fibers each provide a combination of strength, transport rate, and porosity suitable to provide improved fiber fluid recovery as compared to a conventional hollow fiber formed of regenerated cellulose membranes when evaluated in a test system comprising the fibers submerged in a physiologic fluid solution and subjected to negative 180 mm Hg.

2. A system according to claim 1 wherein the one or more catheters are selected from the group consisting of a single catheter comprising a single semipermeable membrane, a single catheter comprising a plurality of semipermeable membranes, a plurality of catheters each comprising a single semipermeable membrane, and a plurality of catheters, each comprising a plurality of semipermeable membranes.

3. An system according to claim 2 wherein one or more catheters comprise a plurality of semipermeable membranes provided in a bundle together with a guide wire.

4. A system according to claim 2 further comprising a component selected from ventriculostomy catheters, introducers, and guide wires.

5. A system according to claim 1 wherein the semipermeable membranes are each provided in the form of hollow fibers having an outer diameter of about 3 mm or less, and are prepared from materials selected from the group consisting of polyacrylonitrile and polysulfone.

6. A system according to claim 5 wherein the fibers are prepared from polyacrylonitrile and provide a molecular weight cut off of at least 50,000 daltons.

7. A system according to claim 5 wherein the hollow fibers are prepared from polysulfone and provide a molecular weight cut off of at least 60,000 daltons.

8. A system according to claim 1 wherein the system is adapted for use in the therapy of cerebral edema or compartment syndrome.

9. A system according to claim 1 wherein the semipermeable membranes are each provided in the form of hollow fibers having an outer diameter of about 3 mm or less.

10. A system according to claim 1 wherein the hollow fibers are prepared from materials selected from the group consisting of polyacrylonitrile and polysulfone.

11. A system according to claim 1 wherein the hollow fibers are prepared from polyacrylonitrile and provide a molecular weight cut off of at least 50,000 daltons.

12. A system according to claim 1 wherein the hollow fibers are prepared from polysulfone and provide a molecular weight cut off of at least 60,000 daltons.

13. A system according to claim 1 wherein the hollow fibers are prepared from polyacrylonitrile and provide fiber fluid recovery of at least 1.86 uL/min/cm.

14. A system according to claim 1 wherein the hollow fibers are prepared from polysulfone and provide a fiber fluid recovery of at least 7.29 uL/min/cm.

15. A method for performing site specific therapy of a tissue site, the method comprising the steps of a) providing a system comprising one or more catheters, each comprising one or more semipermeable membranes in the form of hollow fibers, and each adapted to be positioned within the tissue sites and a delivery/recovery mechanism for employing the catheter(s) to control the movement of bulk fluids and/or active fluid components, within tissue portions, b) positioning the catheter(s) within the tissue site, and c) operating the mechanism in order to control the movement of bulk fluids and/or active fluid components, wherein the delivery/recovery mechanism comprises a source of negative hydrostatic pressure adapted to recover bulk fluids and/or water and permeant solutes through the semipermeable membranes and from the tissue site, wherein the hollow fibers each provide a combination of strength, transport rate, and porosity suitable to provide improved fiber fluid recovery as compared to a conventional hollow fiber formed of regenerated cellulose membrane when evaluated in a test system comprising the fibers submerged in a physiologic fluid solution and subjected to negative 180 mm Hg.

16. A method according to claim 15 wherein the semipermeable membranes are each provided in the form of hollow fibers having an outer diameter of about 3 mm or less, and are prepared from materials selected from the group consisting of polyacrylonitrile and polysulfone.

17. A method according to claim 16 wherein the fibers are prepared from polyacrylonitrile and provide a molecular weight cut off of at least 50,000 daltons.

18. A method according to claim 16 wherein the hollow fibers are prepared from polysulfone and provide a molecular weight cut off of at least 60,000 daltons.

19. A method according to claim 15 wherein the system is adapted for use in the therapy of cerebral edema or compartment syndrome.

20. A method according to claim 15 wherein the semipermeable membranes are each provided in the form of hollow fibers having an outer diameter of about 3 mm or less.

21. A method according to claim 15 wherein the hollow fibers are prepared from materials selected from the group consisting of polyacrylonitrile and polysulfone.

22. A method according to claim 15 wherein the hollow fibers are prepared from polyacrylonitrile and provide a molecular weight cut off of at least 50,000 daltons.

23. A method according to t claim 15 wherein the hollow fibers are prepared from polysulfone and provide a molecular weight cut off of at least 60,000 daltons.

24. A method according to claim 15 wherein the hollow fibers are prepared from polyacrylonitrile and provide fiber fluid recovery of at least 1.86 uL/min/cm.

25. A method according to claim 15 wherein the hollow fibers are prepared from polysulfone and provide a fiber fluid recovery of at least 7.29 uL/min/cm.

26. A method for performing site specific therapy of a tissue site, the method comprising the steps of:
  a) providing a system comprising one or more catheters, each comprising one or more semipermeable membranes in the form of hollow fibers, and each adapted to be positioned within the tissue site and a delivery/recovery mechanism for employing the catheter(s) to control the movement of bulk fluids and/or water and permeant solutes within tissue site, wherein the system is adapted for use in the therapy of compartment syndrome or cerebral edema,
  b) positioning the catheter(s) within the tissue site exhibiting compartment syndrome or cerebral edema, and
  c) operating the mechanism in order to control the movement of bulk fluids and/or water and permeant solutes, wherein
    the delivery/recovery mechanism comprises a source of negative hydrostatic pressure adapted to recover bulk fluids and/or water and permeant solutes from within the tissue site.

27. A method according to claim 26 wherein the semipermeable membranes are each provided in the form of hollow fibers having an outer diameter of about 3 mm or less, and are prepared from materials selected from the group consisting of polyacrylonitrile and polysulfone.

28. A method according to claim 27 wherein the fibers are prepared from polyacrylonitrile and provide a molecular weight cut off of at least 50,000 daltons.

29. A method according to claim 27 wherein the hollow fibers are prepared from polysulfone and provide a molecular weight cut off of at least 60,000 daltons.

30. A method according to claim 28 wherein the rate of fluid removal can be altered by making adjustments to the negative pressure applied to the combined system.

31. A method according to claim 26 wherein the catheters are used for the recovery of bulk fluid from the parenchyma.

32. A method according to claim 26 wherein the system is adapted for use in the therapy of cerebral edema or compartment syndrome.

33. A method according to claim 26 wherein the semipermeable membranes are each provided in the form of hollow fibers having an outer diameter of about 3 mm or less.

34. A method according to claim 26 wherein the hollow fibers are prepared from materials selected from the group consisting of polyacrylonitrile and polysulfone.

35. A method according to claim 26 wherein the hollow fibers are prepared from polyacrylonitrile and provide a molecular weight cut off of at least 50,000 daltons.

36. A method according to claim 26 wherein the hollow fibers are prepared from polysulfone and provide a molecular weight cut off of at least 60,000 daltons.

37. A method according to claim 26 wherein the hollow fibers are prepared from polyacrylonitrile and provide fiber fluid recovery of at least 1.86 uL/min/cm.

38. A method according to claim 26 wherein the hollow fibers are prepared from polysulfone and provide a fiber fluid recovery of at least 7.29 uL/min/cm.

39. A method for performing site specific therapy in order to treat cerebral edema, the method comprising the steps of:
  a) providing a system comprising one or more catheters, in the form of a plurality of semipermeable membranes adapted to be positioned within the brain parenchyma and a delivery/recovery mechanism for employing the hollow fibers to control the movement of bulk fluids and/or water and permeant solutes within the parenchyma,
  b) positioning the hollow fibers within the parenchyma, and
  c) operating the mechanism by applying a source of negative hydrostatic pressure to recover bulk fluids and/or water and permeant solutes through the hollow fibers and from within the tissue site in a manner that achieves a therapeutic effect.

40. A method according to claim 39 wherein the semipermeable membranes are each provided in the form of hollow fibers having an outer diameter of about 3 mm or less, and are prepared from materials selected from the group consisting of polyacrylonitrile and polysulfone.

41. A method according to claim 40 wherein the fibers are prepared from polyacrylonitrile and provide a molecular weight cut off of at least 50,000 daltons.

42. A method according to claim 40 wherein the hollow fibers are prepared from polysulfone and provide a molecular weight cut off of at least 60,000 daltons.

43. A method according to claim 39 wherein the hollow fibers are provided in a bundle together with a guide wire.

44. A method according to claim 39 wherein the semipermeable membranes are selected from dual hollow fibers, a bundle of multiple hollow fibers, coaxial fibers, and fibers provided in a loop configuration.

45. A method according to claim 39 wherein the system is adapted for use in the therapy of cerebral edema or compartment syndrome.

46. A method according to claim 39 wherein the semipermeable membranes are each provided in the form of hollow fibers having an outer diameter of about 3 mm or less.

47. A method according to claim 39 wherein the hollow fibers are prepared from materials selected from the group consisting of polyacrylonitrile and polysulfone.

48. A method according to claim 39 wherein the hollow fibers are prepared from polyacrylonitrile and provide a molecular weight cut off of at least 50,000 daltons.

49. A method according to claim 39 wherein the hollow fibers are prepared from polysulfone and provide a molecular weight cut off of at least 60,000 daltons.

50. A method according to claim 39 wherein the hollow fibers are prepared from polyacrylonitrile and provide fiber fluid recovery of at least 1.86 uL/min/cm.

51. A method according to claim 39 wherein the hollow fibers are prepared from polysulfone and provide a fiber fluid recovery of at least 7.29 uL/min/cm.

* * * * *